US010501448B2

(12) United States Patent
Chen et al.

(10) Patent No.: US 10,501,448 B2
(45) Date of Patent: Dec. 10, 2019

(54) AZIRIDINATED TRIGLYCERIDES AND POLYMERS FORMED THEREFROM

(71) Applicant: Iowa State University Research Foundation, Inc., Ames, IA (US)

(72) Inventors: Ruqi Chen, Shanghai (CN); Jason Shih-Hao Chen, Ames, IA (US); Chaoqun Zhang, Sheldahl, IA (US); Michael Richard Kessler, Pullman, WA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/042,565

(22) Filed: Jul. 23, 2018

(65) Prior Publication Data

US 2018/0327393 A1 Nov. 15, 2018

Related U.S. Application Data

(62) Division of application No. 15/085,345, filed on Mar. 30, 2016, now Pat. No. 10,077,257.

(60) Provisional application No. 62/143,497, filed on Apr. 6, 2015.

(51) Int. Cl.
*C07D 405/12* (2006.01)
*C08G 63/685* (2006.01)
*C08G 73/02* (2006.01)

(52) U.S. Cl.
CPC ....... *C07D 405/12* (2013.01); *C08G 63/6852* (2013.01); *C08G 73/02* (2013.01)

(58) Field of Classification Search
CPC .......................... C07D 405/12; C08G 63/6858
See application file for complete search history.

(56) References Cited

U.S. PATENT DOCUMENTS

| | | | |
|---|---|---|---|
| 4,013,688 A | 3/1977 | Babcock et al. | |
| 4,039,414 A * | 8/1977 | McGinniss | C09D 5/4407 204/478 |
| 4,383,051 A | 5/1983 | Meyborg et al. | |
| 4,559,351 A | 12/1985 | Stoss et al. | |
| 9,688,794 B2 | 6/2017 | Chen et al. | |
| 10,077,257 B2 | 9/2018 | Chen et al. | |
| 10,280,241 B2 | 5/2019 | Chen et al. | |
| 2001/0023276 A1 * | 9/2001 | Schoenfeld | C08G 59/027 525/107 |
| 2015/0274861 A1 | 10/2015 | Chen et al. | |
| 2015/0274880 A1 | 10/2015 | Chen et al. | |
| 2016/0289218 A1 | 10/2016 | Chen et al. | |
| 2017/0226243 A1 | 8/2017 | Chen et al. | |

FOREIGN PATENT DOCUMENTS

| | | |
|---|---|---|
| CN | 1384109 A | 12/2002 |
| DE | 102007006442 A1 | 8/2008 |
| EA | 000565 B1 | 12/1999 |
| EP | 0114270 A1 | 8/1984 |
| GB | 985614 | 3/1965 |
| JP | 2002265419 A | 9/2002 |
| KR | 20130070970 A | 6/2013 |
| WO | WO-9636639 A1 | 11/1996 |
| WO | WO-9702307 A1 | 1/1997 |
| WO | WO-0108677 A1 | 2/2001 |
| WO | WO-2004098538 A2 | 11/2004 |
| WO | WO-2010138842 A1 | 12/2010 |
| WO | WO-2013066461 A2 | 5/2013 |
| WO | WO-2014062625 A1 | 4/2014 |
| WO | WO-2014062631 A1 | 4/2014 |

OTHER PUBLICATIONS

"U.S. Appl. No. 14/434,719, Notice of Allowability dated Apr. 4, 2017", 5 pgs.
"U.S. Appl. No. 14/434,719, Notice of Allowance dated Mar. 23, 2017", 11 pgs.
"U.S. Appl. No. 14/434,719, Response filed Oct. 11, 2016 to Restriction Requirement dated Aug. 25, 2016", 13 pgs.
"U.S. Appl. No. 14/434,719, Restriction Requirement dated Aug. 25, 2016", 8 pgs.
"U.S. Appl. No. 15/085,345, Non Final Office Action dated Nov. 27, 2017", 9 pgs.
"U.S. Appl. No. 15/085,345, Notice of Allowance dated May 30, 2018", 12 pgs.
"U.S. Appl. No. 15/085,345, Response filed Feb. 27, 2018 to Non Final Office Action dated Nov. 27, 2017", 13 pgs.
"U.S. Appl. No. 15/085,345, Response filed Sep. 25, 2017 to Restriction Requirement dated Jul. 27, 2017", 10 pgs.
"U.S. Appl. No. 15/085,345, Restriction Requirement dated Jul. 27, 2017", 9 pgs.
"U.S. Appl. No. 15/581,229, Notice of Allowance dated Nov. 24, 2017", 9 pgs.
"U.S. Appl. No. 15/581,229, Preliminary Amendment filed May 1, 2017", 12 pgs.
"U.S. Appl. No. 15/881,117, Preliminary Amendment filedJan. 29, 2018", 14 pgs.
"Application Serial No. Preliminary Amendment filed Apr. 9, 2015", 13 pgs.
"International Application Serial No. PCT/US2013/064960, International Preliminary Report on Patentability dated Apr. 30, 2015", 12 pgs.
"International Application Serial No. PCT/US2013/064960, International Search Report dated Feb. 4, 2014", 8 pgs.
"International Application Serial No. PCT/US2013/064960, Written Opinion dated Feb. 4, 2014", 10 pgs.

(Continued)

*Primary Examiner* — Gregory Listvoyb
(74) *Attorney, Agent, or Firm* — Schwegman Lundberg & Woessner, P.A.

(57) ABSTRACT

Various embodiments disclosed relate to aziridinated triglycerides and polymers formed therefrom. In various embodiments, the present invention provides an aziridinated triglyceride having the structure described herein. In various embodiments, the present invention provides a method of making the aziridinated triglyceride, a method of crosslinking the aziridinated triglyceride to form a polymer, the polymer formed from the aziridinated triglyceride, a triglyceride with at least one pendent unsaturated group that can be used to form the aziridinated triglyceride, and a method of making the triglyceride having at least one pendent unsaturated group.

20 Claims, 7 Drawing Sheets

(56) References Cited

OTHER PUBLICATIONS

"International Application Serial No. PCT/US2013/064972, International Preliminary Report on Patentability dated Apr. 30, 2015", 10 pgs.

"International Application Serial No. PCT/US2013/064972, International Search Report dated Feb. 4, 2014", 5 pgs.

"International Application Serial No. PCT/US2013/064972, Written Opinion dated Feb. 4, 2014", 8 pgs.

Bachmann, Frank, et al., "Synthesis of Novel Polyurethanes and Polyureas by Polyaddition Reactions of Dianhydrohexitol Configurated Diisocyanates", Macromol. Chem. Phys., vol. 202, No. 17, (Jan. 1, 2001), 3410-3419.

Barros, Thalita G, et al., "Novel Peptide Mimetics Based on N-protected Amino Acids Derived from Isomannide as Potential Inhibitors of NS3 Serine Protease of Hepatitis C Virus", Letters in Organic Chemistry, vol. 9, No. 4, (Feb. 1, 2012), 239-249.

Beldi, M., et al., "Characterization of cyclic and non-cyclic poly(ether-urethane)s bio-based sugar dials by a combination of MAIDI-TOF and NMR", European Polymer Journal, 43, (2007), 3415-3433.

Chen, "Bio-based polymeric materials from vegetable oils", PhD thesis, Iowa State University, (Oct. 2014).

Chen, Po-Cheng, et al., "New Crosslinked Polymer from a Rapid Polymerization of Acrylic Acid with Triaziridine-Containing Compounds", Journal of Applied Polymer Science, vol. 104, (2007), 809-815.

Cocker, J. D, et al., "Action of some steroids on the central nervous system of the mouse. I. Synthetic methods", Journal of Medicinal Chemistry 8(4), (1965).

Feng, Xianhong, et al., "Overview of advances in sugar-based polymers", Polymers for Advanced Technologies, vol. 22, No. 1, (Jan. 10, 2011), 139-150.

Garaleh, Mazen, et al., "(Co-)Polyesters Derived from Isosorbide and 1,4-Cyclohexane Dicarboxylic Acid and Succinic Acid", Macromol. Chem. Phys., 211, (2010), 1206-1214.

Gohil, R. M., "Properties and Strain Hardening Character of Polyethylene Terephthalate Containing Isosorbide", Polymer Engineering and Science, (2009), 544-553.

Hojabri, Leila, et al., "Fatty Acid-Derived Diisocyanate and Biobased Polyurethane Produced from Vegetable Oil: Synthesis, Polymerization, and Characterization", Biomacromolecules, 10, (1009), 884-891.

Hojabri, Leila, et al., "Novel Long Chain Unsaturated Diisocyanate from Fatty Acid: Synthesis, Characterization, and Application in Bio-Based Polyurethane", Journal of Polymer Part A: Polymer Chemistry, 48, (2010), 3302-3310.

Imm, Sebastian, et al., "Improved Ruthenium-Catalyzed Amination of Alcohols with Ammonia: Synthesis of Diamines and Amino Esters", Angew. Chem. Int. Ed., 50, (2011), 7599-7603.

Lee, Chi-Han, et al., "Synthesis, Characterization, and Properties of Polyurethanes Containing 1,4:3,6-Dianhydro-D-sorbitol", Journal of Polymer Science: Part A: Polymer Chemistry, 47, (2009), 6025-6031.

Li, Ruilin, et al., "Synthesis and antifertility activities of A-nor-steroidai compounds", Yiyao Gongye, 17(9), (1987).

Ligadas, et al., "Renewable polymeric materials from vegetable oils: a perspective", Material stoday, vol. 16, issue 9, (Sep. 2013), 337-343.

Marin, Romina, et al., "Carbohydrate-Based Poly(ester-urethane)s: A Comparative Study Regarding Cyclic Alditols Extenders and Polymerization Procedures", Journal of Applied Polymer Science, 114, (2009), 3723-3736.

Min, Zhen Li, et al., "Asymmetric synthesis of 3-butylphthalide using isomannide and isosorbide as chiral auxiliaries", Chinese Chemical Letters, vol. 18, No. 11, (Nov. 5, 2007), 1361-1363.

Nakamura, Yoshinobu, et al., "Effects of the Compatibility of a Polyacrylic Block Copolymer/Tackifier Blend on the Phase Structure and Tack of a Pressure-Sensitive Adhesive", Journal of Applied Polymer Science, vol. 123, No. 5, (Mar. 5, 2012), 2883-2893.

Rose, Marcus, et al., "Isosorbide as a Renewable Platform chemical for Versatile Applications-Quo Vadis?", ChemSusChem, 5, (2012), 167-176.

Sabiong, Rafaei, et al., "Incorporation of Isosorbide into Poly(butyiene terephthalate) via Solid-State Polymerization", Macromolecules, American Chemical Society, vol. 9, (Nov. 10, 2008), 3090-3097.

Scalia, Santo, et al., "HPLC determination of ursodeoxycholic acid disuccinate in tablet formulations", (1991), 2 pgs.

Schoenfeld, Uwe, "Polymer Material", patsnap, EA000565B1; Publication No.=EA000565B1; Application No.=EA980004AAssignee, Abstract Only; Assignee Name—Preform Raumgliederungssysteme Gmbh, DE.; International Patent IPC(1-7): C08G59/42 C08L63/08 C08G59/34; Priority Data: 19524514 Jul. 1995 DE; 9601243 05 Jul. 1996.

Stemmelen, M., et al., "A Fully Biobased Epoxy Resin from Vegetable Oils: From the Synthesis of the Precursors by Thiol-ene Reaction to the Study of the Final Material", accepted Mar. 14, 2011; DOI: 10. 1002/pola.24674; Published online Apr. 8, 2011 in Wiley Online Library (wileyonlinelibrary.com)., wileyonlinelibrary.com/journal/jpola, (Apr. 8, 2011), 2434-2444.

Thiem, Joachim, et al., "Synthesis and properties of polyurethanes derived from diaminodianhydroalditols", Makromol. Chem., 187, (1986), 2775-2785.

Varkey, Elizabeth Chirackal, et al., "Isosorbide based chiral polyurethanes: optical and thermal studies", Journal of Materials Science, vol. 45, No. 7, (Jan. 13, 2010), 1912-1920.

Xia, et al., "Castor-Oil-Based Waterborne Polyurethane Dispersions Cured with an Aziridine-Based Crosslinker", Macromol. Mater. Eng., (Apr. 2011), 703-709.

Zenner, Michael D, et al., "Polyurethanes from Isosorbide-Based Diisocyanates", ChemSusChem, 6, (2013), 1182-1185.

"U.S. Appl. No. 15/881,117, Notice of Allowability dated Mar. 14, 2019", 2 pgs.

"U.S. Appl. No. 15/881,117, Notice of Allowance dated Feb. 20, 2019", 9 pgs.

* cited by examiner

AZIRIDINATED TRIGLYCERIDES AND POLYMERS FORMED THEREFROM

CROSS-REFERENCE TO RELATED APPLICATION

This application is a divisional of U.S. patent application Ser. No. 15/085,345, filed Mar. 30, 2016, which application claims the benefit of priority to U.S. Provisional Patent Application Ser. No. 62/143,497, filed Apr. 6, 2015, the disclosures of which are incorporated herein in their entirety by reference.

BACKGROUND

The development of new materials such as polymeric materials from renewable resources is gaining considerable attention. Biorenewability is directed toward a sustainable raw material supply where the raw material is renewed from plants or other biological matter, generally through agriculture. Biorenewable polymers are pursued as environmentally friendly replacements for commodity plastics from petrochemical starting materials. The goal is to use low cost readily available starting materials from biorenewable resources such that biorenewable polymers can be competitive with current petroleum-derived materials in the marketplace.

SUMMARY OF THE INVENTION

In various embodiments, the present invention provides an aziridinated triglyceride having the structure:

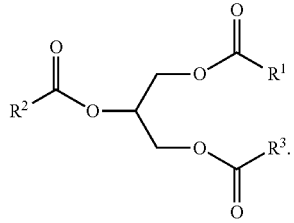

The variables $R^1$, $R^2$, and $R^3$ are each independently a substituted or unsubstituted ($C_1$-$C_{50}$)hydrocarbyl optionally interrupted or terminated by at least one -AZ— group having the structure:

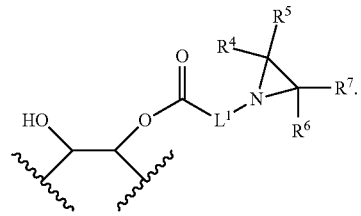

At each occurrence, $L^1$ is independently a substituted or unsubstituted ($C_2$-$C_{50}$)hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ are independently chosen from —H and substituted or unsubstituted ($C_1$-$C_{10}$)hydrocarbyl interrupted or terminated with 0, 1, 2, or 3 groups independently chosen from —O—, —S—, and substituted or unsubstituted —NH—. The aziridinated triglyceride includes at least one of the -AZ— groups.

In various embodiments, the present invention provides a method of making the aziridinated triglyceride. The method includes combining an epoxidized triglyceride with a substituted or unsubstituted ($C_3$-$C_{50}$)carboxylic acid including at least one aliphatic unsaturated carbon-carbon bond (e.g., double bond). The method includes treating the ($C_3$-$C_{50}$) carboxylic acid-treated product with an aziridine having the structure:

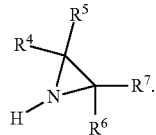

At each occurrence, $R^4$, $R^5$, $R^6$, and $R^7$ are independently chosen from —H and substituted or unsubstituted ($C_1$-$C_{10}$) hydrocarbyl interrupted or terminated with 0, 1, 2, or 3 groups independently chosen from —O—, —S—, and substituted or unsubstituted —NH—. Treatment of the of the ($C_3$-$C_{50}$)carboxylic acid-treated product with the aziridine gives the aziridinated triglyceride.

In various embodiments, the present invention provides a method of crosslinking the aziridinated triglyceride. The method includes contacting the aziridinated triglyceride with a crosslinker, to form a crosslinked triglyceride (e.g., a polymer).

In various embodiments, the present invention provides a polymer formed from a reaction of the aziridinated triglyceride and a crosslinker such as a polycarboxylic acid.

In various embodiments, the present invention provides a polymer having the structure:

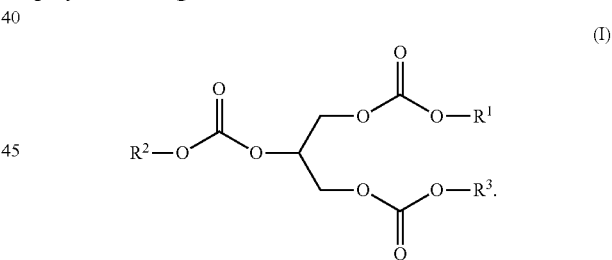

(I)

The variables $R^1$, $R^2$, and $R^3$ are each independently a substituted or unsubstituted ($C_1$-$C_{50}$)hydrocarbyl optionally interrupted or terminated by the A end of at least one -AZP— group having the structure:

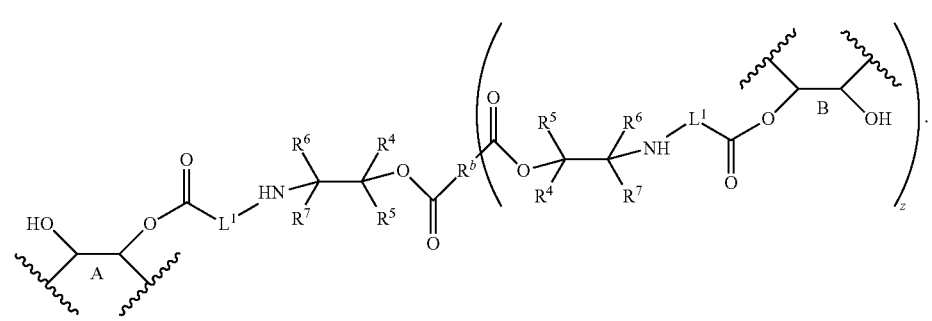

At each occurrence. $L^1$ is independently a substituted or unsubstituted $(C_2-C_{50})$hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ are independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. The variable $R^b$ is a substituted or unsubstituted $(C_1-C_{50})$hydrocarbyl having a valence of $z+1$, wherein $R^b$ is interrupted or terminated by 0, 1, 2, or 3 groups independently chosen from —O—, —S—, substituted or unsubstituted —NH—, and —(O—$(C_2-C_3)$alkylene)$_n$- wherein n is about 1 to about 10,000 and wherein the $(C_2-C_3)$alkylene is substituted or unsubstituted. The variable z is about 1 to about 1,000. The triglyceride I includes at least one of the -AZP— groups. Each B end of the -AZP— group is independently interrupting or terminating $R^1$, $R^2$, or $R^3$ of the same or different triglyceride I, wherein at least one B end of at least one -AZP— group in the triglyceride I interrupts or terminates $R^1$, $R^2$, or $R^3$ of a different triglyceride I.

In various embodiments, the present invention provides a triglyceride having at least one pendent unsaturated group, the triglyceride having the structure:

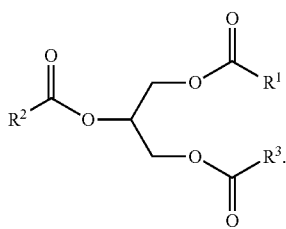

The variables $R^1$, $R^2$, and $R^3$ are each independently a substituted or unsubstituted $(C_1-C_{50})$hydrocarbyl optionally interrupted or terminated by at least one -A- group having the structure:

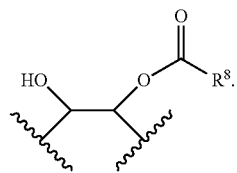

At each occurrence, $R^8$ is independently a substituted or unsubstituted $(C_2-C_{50})$hydrocarbyl including at least one aliphatic carbon-carbon unsaturated bond and is interrupted or terminated with 0, 1, 2, or 3 groups independently chosen from —O—, —S—, and substituted or unsubstituted —NH—. The triglyceride includes at least one of the -A- groups.

In various embodiments, the present invention provides a method of making the triglyceride having at least one pendent unsaturated group. The method includes combining an epoxidized triglyceride with a substituted or unsubstituted $(C_3-C_{50})$carboxylic acid including at least one aliphatic unsaturated carbon-carbon bond to give the triglyceride having at least one pendent unsaturated group.

Various embodiments of the present invention provide certain advantages over other multiaziridine compounds and polymers derived from the same, at least some of which are unexpected. Unlike most multiaziridine-based compounds which are derived from petroleum-based non bio-renewable materials, in various embodiments, the aziridinated triglyceride and the polymer made therefrom can be synthesized from natural bio-renewable sources such as soybean oil or other natural oils. In various embodiments, the aziridinated triglyceride can be crosslinked using bio-based polyacids, giving a polymer with a higher degree of bio-renewable content than other polymers, including other polymers derived from multiaziridine-based compounds. In various embodiments, the aziridinated triglyceride can be crosslinked with polyacids rapidly at convenient mild temperatures such as room temperature. In various embodiments, the aziridinated triglyceride can be crosslinked with polyacids without the use of external reagents.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
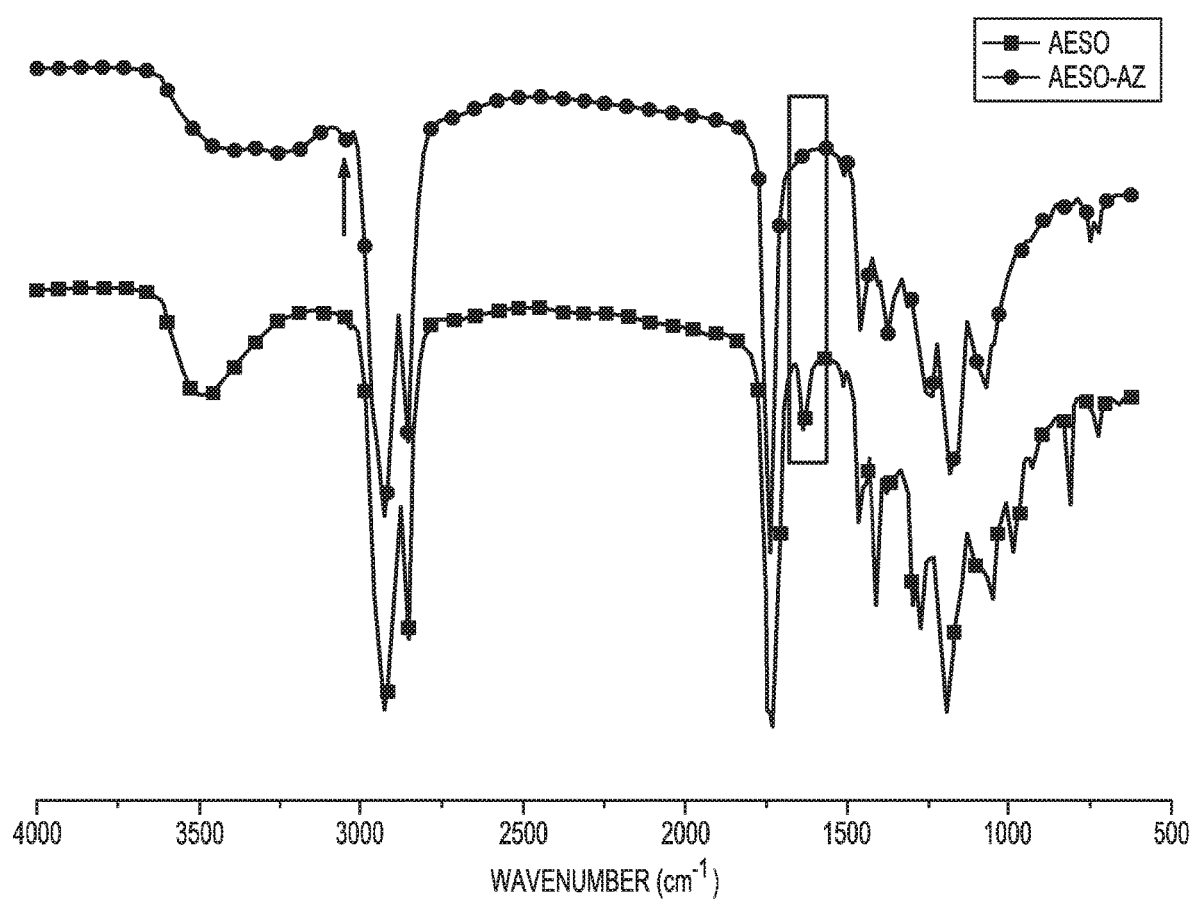
FIG. 1 illustrates FTIR spectra of acrylated epoxidized soybean oil (AESO) and aziridinated acrylated epoxidized soybean oil (ASEO-AZ), in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy. N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O). S(O), methylenedioxy, ethylenedioxy. N(R)$_2$. SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$. N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl heterocyclyl heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "monovalent" as used herein refers to a substituent connecting via a single bond to a substituted molecule. When a substituent is monovalent, such as, for example, F or CL it is bonded to the atom it is substituting by a single bond.

The term "hydrocarbon" or "hydrocarbyl" as used herein refers to a molecule or functional group, respectively, that includes carbon and hydrogen atoms. The term can also refer to molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "number-average molecular weight" ($M_n$) as used herein refers to the ordinary arithmetic mean of the molecular weight of individual molecules in a sample. It is defined as the total weight of all molecules in a sample divided by the total number of molecules in the sample. Experimentally, $M_n$ is determined by analyzing a sample divided into molecular weight fractions of species i having $n_i$ molecules of molecular weight $M_i$ through the formula $M_n=\Sigma M_i n_i/\Sigma n_i$. The $M_n$ can be measured by a variety of well-known methods including gel permeation chromatography, spectroscopic end group analysis, and osmometry. If unspecified, molecular weights of polymers given herein are number-average molecular weights.

The term "oligomer" as used herein refers to a molecule having an intermediate relative molecular mass, the structure of which essentially includes a small plurality of units derived, actually or conceptually, from molecules of lower relative molecular mass. A molecule having an intermediate relative mass can be a molecule that has properties that vary with the removal of one or a few of the units. The variation in the properties that results from the removal of the one of more units can be a significant variation.

The term "room temperature" as used herein refers to a temperature of about 15° C. to 28° C.

As used herein, the term "polymer" refers to a molecule having at least one repeating unit and can include copolymers.

The polymers described herein can terminate in any suitable way. In some embodiments, the polymers can terminate with an end group that is independently chosen from a suitable polymerization initiator, —H, —OH, a substituted or unsubstituted $(C_1-C_{20})$hydrocarbyl (e.g., $(C_1-C_{10})$alkyl or $(C_6-C_{20})$aryl) interrupted with 0, 1, 2, or 3 groups independently chosen from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

Aziridinated Triglyceride.

In various embodiments, the present invention provides an aziridinated triglyceride having the structure:

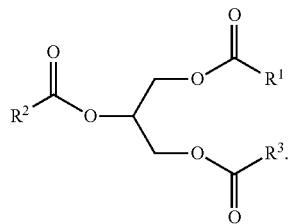

The variables $R^1$, $R^2$, and $R^3$ can each independently be a substituted or unsubstituted $(C_1-C_{50})$hydrocarbyl optionally interrupted or terminated by at least one -AZ— group having the structure:

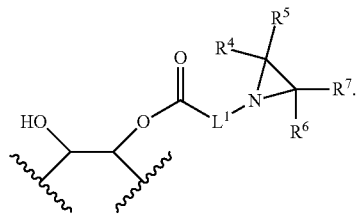

At each occurrence, $L^1$ can be independently a substituted or unsubstituted $(C_2-C_{50})$hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ can be independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. The aziridinated triglyceride can include at least one of the -AZ— groups.

The variables $R^1$, $R^2$, and $R^3$ can be each independently a substituted or unsubstituted $(C_1-C_{50})$hydrocarbyl optionally interrupted or terminated by at least one -AZ— group. The variables $R^1$, $R^2$, and $R^3$ can each be independently a substituted or unsubstituted $(C_{10}-C_{50})$hydrocarbyl optionally interrupted or terminated by at least one -AZ— group. The variables $R^1$, $R^2$, and $R^3$ can each be independently a substituted or unsubstituted $(C_1-C_{50})$alkane optionally interrupted or terminated with at least one of the -AZ— groups. The variables $R^1$, $R^2$, and $R^3$ can each be independently a $(C_1-C_{50})$alkane optionally interrupted or terminated with at least one of the -AZ— groups, substituted with 0, 1, 2, 3, 4, or 5 epoxy groups, and otherwise unsubstituted. The variables $R^1$, $R^2$, and $R^3$ can each be independently an unsubstituted $(C_1-C_{50})$alkane optionally interrupted or terminated with at least one of the -AZ— groups.

At each occurrence, $L^1$ can be independently a substituted or unsubstituted $(C_2-C_{50})$hydrocarbyl interrupted or terminated with 0, 1, 2, or 3 groups independently chosen from —O—, —S—, and substituted or unsubstituted —NH—. At each occurrence, $L^1$ can be independently an unsubstituted $(C_2-C_{50})$alkanylene. At each occurrence, $L^1$ can be independently an unsubstituted $(C_2-C_{10})$alkanylene. At each occurrence, $L^1$ can be independently an unsubstituted $(C_2-C_{10})$alkanylene.

At each occurrence, $R^4$, $R^5$, $R^6$, and $R^7$ can be independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ can be independently chosen from —H and unsubstituted $(C_1-C_{10})$hydrocarbyl. At each occurrence, $R^5$, $R^6$, and $R^7$ can be —H. At each occurrence, $R^5$, $R^6$, and $R^7$ can be —H, and $R^4$ can be unsubstituted $(C_1-C_{10})$ hydrocarbyl. At each occurrence, $R^5$, $R^6$, and $R^7$ can be —H, and $R^4$ can be unsubstituted $(C_1-C_5)$alkyl. At each occurrence, $R^5$, $R^6$, and $R^7$ can be —H, and $R^4$ can be methyl.

The aziridinated triglyceride can include at least one of the -AZ— groups. The aziridinated triglyceride can include one of the -AZ— groups (e.g., a monoaziridinated triglyceride). The aziridinated triglyceride can include two or more of the -AZ— groups (e.g., a multiaziridinated triglyceride). The at least one -AZ— group can interrupt or terminate (e.g., begin, such as -AZ— $R^1$, or end, such as —R'-AZ— H) $R^1$, $R^2$, or $R^3$. The aziridinated triglyceride can include any suitable number of the -AZ— groups interrupting or terminating $R^1$, $R^2$, or $R^3$, such as about 1, 2, 3, 4, 5, 6, 7, 8, 9, or about 10 or more. In some embodiments, one or more of $R^1$, $R^2$, and $R^3$ have two or more -AZ— groups. In some embodiments, none of $R^1$, $R^2$, or $R^3$ have more than one -AZ— group each.

In some embodiments, -AZ— can have the structure:

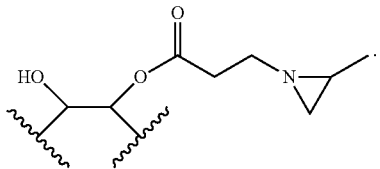 [SMILES: *C(O)C(*)OC(=O)CCN1CC1C]

The aziridinated triglyceride can be derived from a triglyceride (e.g., an oil), such as any triglyceride starting material described herein. The triglyceride starting material can include unsaturated groups. The triglyceride starting material including unsaturated groups can be epoxidized, such that at least some of the unsaturated groups are converted to epoxide groups. The epoxidized product can be treated with a substituted or unsubstituted $(C_3-C_{50})$carboxylic acid including at least one aliphatic unsaturated carbon-carbon bond to provide a triglyceride that includes at least one pendant group that includes at least one aliphatic unsaturated carbon-carbon bond. The at least one aliphatic unsaturated carbon-carbon bond can be an α,β-unsaturated aliphatic double bond conjugated with a carbonyl group, such that the double bond is a suitable Michael-acceptor for subsequent reaction with an aziridine. The $(C_3-C_{50})$carboxylic acid-treated product can be treated with an aziridine having the structure:

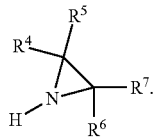

The variables $R^4$, $R^5$, $R^6$, and $R^7$ are as defined herein.

In various embodiments, the aziridinated triglyceride can have the structure:

Triglyceride Starting Materials.

The aziridinated triglyceride can be derived from one or more triglycerides such as one or more oils, such as via epoxidation, treatment with an a substituted or unsubstituted $(C_3-C_{50})$carboxylic acid including at least one aliphatic unsaturated carbon-carbon bond, and treating with an aziridine. The triglyceride starting material can be any suitable one or more triglycerides that include at least one unsaturated carbon-carbon bond (e.g., double bond) suitable for epoxidation. For example, the triglyceride can be açaí oil, almond oil, amaranth oil, apple seed oil, apricot oil, argan oil, avocado oil, babassu oil, beech nut oil, ben oil, bitter gourd oil (from the seeds of *Momordica charantia*), black seed oil, blackcurrant seed oil (from the seeds of *Ribes nigrum*), borage seed oil (from the seeds of *Borago officinalis*), borneo tallow nut oil, bottle gourd oil (from the seeds of the *Lagenaria siceraria*), buffalo gourd oil (from the seeds of the *Cucurbita foetidissima*), butternut squash seed oil (from the seeds of *Cucurbita moschata*), camelina sativa oil, cape chestnut oil (yangu oil), carob pod oil, cashew oil, cocklebur oil, cocoa butter, coconut oil, cohune oil, coriander seed oil, corn oil, cottonseed oil, date seed oil, dika oil, egusi seed oil (from the seeds of *Cucumeropsis mannii naudin*), evening primrose oil (from the seeds of *Oenothera biennis*), flaxseed oil (from the seeds of *Linum usitatissimum*), grape seed oil, grapefruit seed oil, hazelnut oil, hemp oil, kapok seed oil, kenaf seed oil (from the seeds of *Hibiscus cannabinus*), *lallemantia* oil (from the seeds of *Lallemantia iberica*), linseed oil, macadamia oil, mafura oil (from the seeds of *Trichilia emetic*), marula oil (from the kernel of *Sclerocarya birrea*), meadowfoam seed oil, mongongo nut oil (manketti oil), mustard oil, niger seed oil, okra seed oil olive oil, orange oil, palm oil, *papaya* seed oil, peanut oil, pecan oil, pequi oil (from the seeds of *Caryocar brasiliense*), *perilla* seed oil, persimmon seed oil (from the seeds of *Diospyros virginiana*), pili nut oil (from the seeds of *Canarium ovatum*), pistachio oil, pomegranate seed oil, poppyseed oil, prune kernel oil, pumpkin seed oil, *quinoa* oil, ramtil oil (from *Guizotia abyssinica*, the *Niger* pea), rapeseed oil, rice bran oil, royle oil (from the seeds of *Prinsepia utilis*), safflower oil, sapote oil, seje oil (from the seeds of *Jessenia bataua*), sesame oil, shea butter, soybean oil, sunflower oil, taramira oil, tea seed oil (*Camellia* oil), thistle oil, tigernut oil (or nut-sedge oil), tobacco seed oil, tomato seed oil, walnut oil, watermelon seed oil, wheat germ oil, agarwood oil, allspice oil, almond oil, anise oil, basil oil, bay leaf oil, benzoin oil, bergamot oil, buchu oil, camphor oil, *cannabis* oil *cassia* oil, cedar oil celery oil, chamomile oil, cinnamon oil, clary sage oil, clove oil, copaiba oil, cumin oil, *eucalyptus* oil, frankincense oil, galangal oil, geranium oil, ginger oil, grapefruit oil, guava oil, hops oil, hyssop oil, jasmine oil, juniper oil, lavender oil, lemon grass oil, lemon oil, lemongrass oil, lime oil, manuka oil, mandarin orange, marjoram oil, *melaleuca* oil, myrrh oil, nutmeg

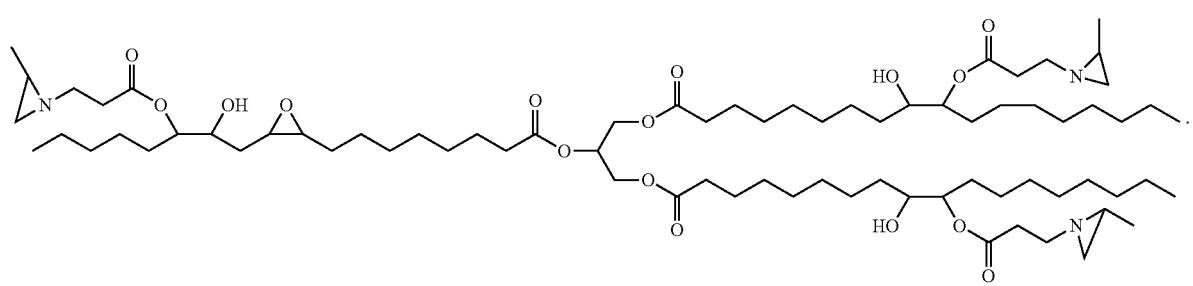 [SMILES: CCCCCCCCC(OC(=O)CCN1CC1C)C(O)CCCCCCCC(=O)OCC(COC(=O)CCCCCCCC(O)C(CCCCCCCC)OC(=O)CCN1CC1C)OC(=O)CCCCCCCC1OC1CC(O)C(CCCCC)OC(=O)CCN1CC1C]

oil, orange oil, oregano oil, patchouli oil, peppermint oil, pine oil, rose oil, rosehip oil, rosemary oil, rosewood oil, sage oil, sandalwood oil, *sassafras* oil, spearmint oil, tangerine oil, tea tree oil, thyme oil, *tsuga* oil, valerian oil, vanilla oil, wintergreen oil, ylang-ylang oil, one or more fractions thereof (e.g., one or more components of the oil), or a combination thereof. In various embodiments, the triglyceride can be soybean oil.

Method of Making an Aziridinated Triglyceride.

In various embodiments, the present invention provides a method of making an aziridinated triglyceride, such as any aziridinated triglyceride described herein. The method can be any suitable method of making the aziridinated triglyceride. In some embodiments, the method includes combining an epoxidized triglyceride with a substituted or unsubstituted $(C_3-C_{50})$carboxylic acid including at least one aliphatic unsaturated carbon-carbon bond, such as including at least one α,β-unsaturated aliphatic double bond conjugated with a carbonyl group, such that the double bond is a suitable Michael-acceptor for subsequent reaction with an aziridine. The method can include treating the $(C_3-C_{50})$carboxylic acid-treated product with an aziridine having the structure:

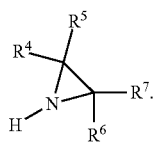

Treatment of the $(C_3-C_{50})$carboxylic acid-treated product with an aziridine gives the aziridinated triglyceride. At each occurrence, $R^4$, $R^5$, $R^6$, and $R^7$ can be independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ can be independently chosen from —H and unsubstituted $(C_1-C_{10})$hydrocarbyl. At each occurrence, $R^5$, $R^6$, and $R^7$ can be —H. At each occurrence, $R^5$, $R^6$, and $R^7$ can be —H, and $R^4$ can be unsubstituted $(C_1-C_{10})$hydrocarbyl. At each occurrence, $R^5$, $R^6$, and $R^7$ can be —H, and $R^4$ can be unsubstituted $(C_1-C_5)$alkyl. At each occurrence, $R^5$, $R^6$, and $R^7$ can be —H, and $R^4$ can be methyl.

Method of Crosslinking an Aziridinated Triglyceride.

In various embodiments, the present invention provides a method of crosslinking an aziridinated triglyceride, such as any aziridinated triglyceride described herein. The method can include contacting the aziridinated triglyceride with one or more crosslinkers, to form a crosslinked triglyceride. The crosslinker can be any suitable crosslinker than can crosslinking two or more molecules of the aziridinated triglyceride, such as via reaction with the aziridine groups.

In some embodiments, the crosslinker is a polycarboxylic acid. The polycarboxylic acid can be any suitable polycarboxylic acid. In some embodiments, the polycarboxylic acid is at least one of a HOC(O)—$R^a$—C(O)OH wherein $R^a$ is a substituted or unsubstituted $(C_1-C_{50})$hydrocarbylene interrupted or terminated by 0, 1, 2, or 3 groups independently chosen from —O—, —S—, substituted or unsubstituted —NH—, and —(O—$(C_2-C_3)$alkylene)$_n$- wherein n is about 1 to about 10,000 (e.g., about 1, 2, 3, 4, 5, 6, 7, 8, 9, 10, 11, 12, 14, 16, 18, 20, 25, 30, 35, 40, 45, 50, 60, 70, 80, 90, 100, 200, 500, 1,000, 2,000, 5.000, or about 10,000 or more) and wherein the $(C_2-C_3)$alkylene is substituted or unsubstituted (e.g., poly(ethyleneoxide) or poly(propyleneoxide), oxalic acid, maleic acid, succinic acid, methylsuccinic acid, malonic acid, adipic acid, glutaric acid, fumaric acid, dihydroxyfumaric acid, malic acid, mesaconic acid, itaconic acid, phthalic acid, isophthalic acid, terephthalic acid, 1,2-, 1,3-, or 1,4-cyclohexane dicarboxylic acid, 1,2,3-cyclohexane tricarboxylic acid, 1,2,4-cyclohexane tricarboxylic acid, 1,3,5-cyclohexane tricarboxylic acid, 1,2- or 1,3-cyclopentane dicarboxylic acid, citric acid, tartaric acid, dihydroxyterephthalic acid, 1,2,3-, 1,2,4-, or 1,2,5-benzene tricarboxylic acid, tricarballylic acid, 1,2,4,5-benzene tetracarboxylic acid, norbornene tetracarboxylic acid, 3,3', 4,4'-benzophenone tetracarboxylic acid, 1,2,3,4,5,6-benzene hexacarboxylic acid, aspartic acid, polyacrylic acid, and glutamic acid. In various embodiments, the polycarboxylic acid is succinic acid, citric acid, an isosorbide-based diacid, or a combination thereof.

In some embodiments, the polycarboxylic acid has the structure:

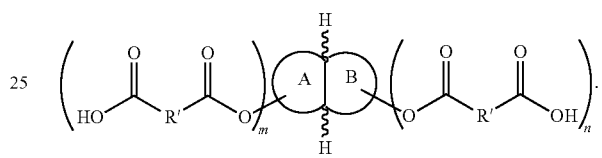

Fused rings A and B can be each independently chosen from substituted or unsubstituted $(C_5-C_{10})$cycloalkyl and $(C_2-C_{10})$heterocyclyl. The variables m and n can each be independently about 1 to about 8. At each occurrence R' can be independently chosen from substituted or unsubstituted $(C_2-C_{10})$hydrocarbylene.

At each occurrence R' can be independently chosen from substituted or unsubstituted $(C_2-C_{10})$hydrocarbylene. At each occurrence R' can be independently unsubstituted. At each occurrence R' can be independently chosen from $(C_1-C_5)$alkylene, $(C_5-C_{10})$aryl, and $(C_2-C_5)$alkenylene. At each occurrence R' can be independently chosen from —CH$_2$—CH$_2$—, —CH$_2$—CH$_2$—CH$_2$—, o-phenylene, and —CH=CH—.

The variables m and n can each be independently about 1 to about 8, such as about 1, 2, 3, 4, 5, 6, 7, or about 8. In some embodiments, m can have the same value as n. The variables m and n can both be 1.

Fused rings A and B can be each independently chosen from substituted or unsubstituted $(C_5-C_{10})$cycloalkyl and $(C_2-C_{10})$heterocyclyl. Rings A and B are unsubstituted with the exception of the one or more ester substituents —OC(O)—R'—C(O)OH. The variables m and n can each be 1, and one of the ester substituents including R' can be alpha to at least one carbon atom shared by rings A and B. Rings A and B can be the same size. Rings A and B can be 5-membered rings. At least one of rings A and B can include at least one oxygen atom. Each of rings A and B can be a tetrahydrofuran ring, wherein each carbon atom shared by rings A and B has an oxygen atom alpha thereto. In some embodiments, each of the ester substituents —OC(O)—R'—C(O)OH are alpha to a different carbon atom shared by each of rings A and B. Rings A and B can form a ring system chosen from isosorbide, isomannide, and isoidide. Rings A and B can be unsubstituted, other than the ester substituents, —OC(O)—R'—C(O)OH.

In various embodiments, the polycarboxylic acid can have the structure:

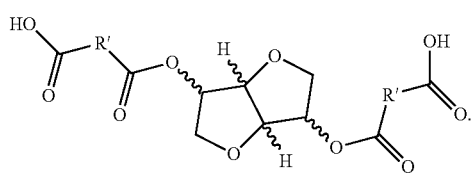
In various embodiments, the polycarboxylic acid is chosen from:
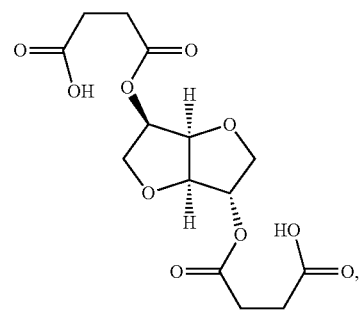
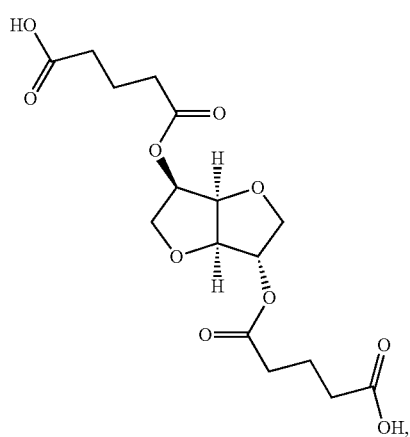
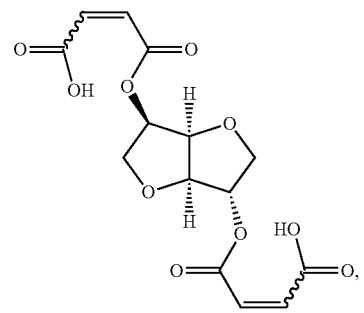
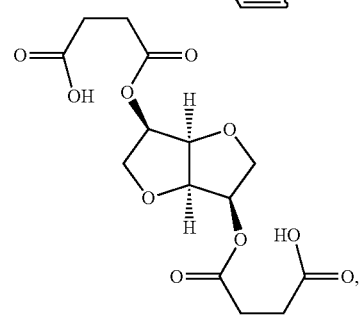
-continued
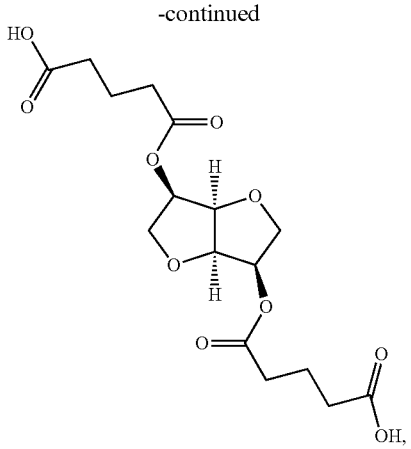
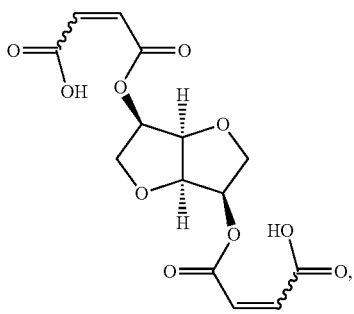
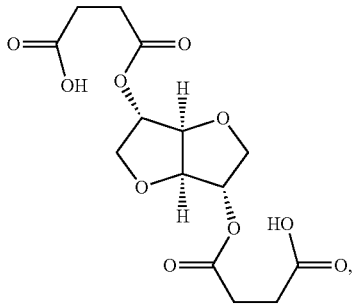
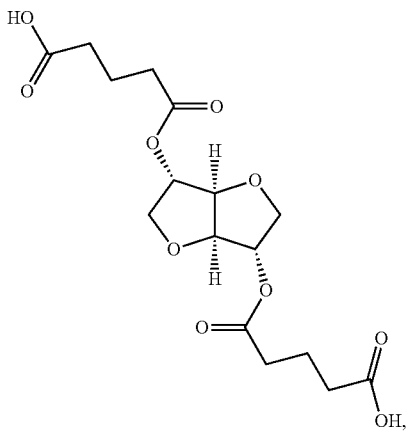

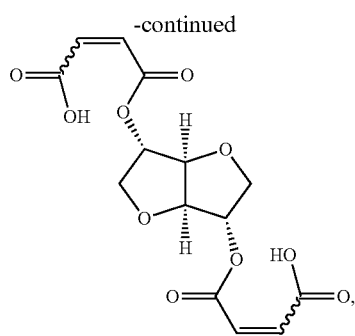
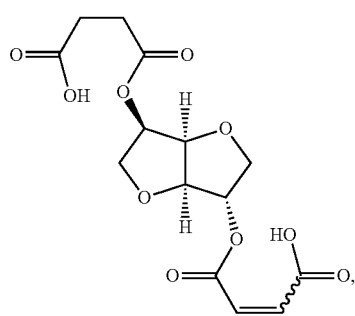
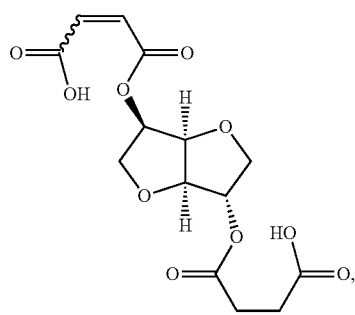
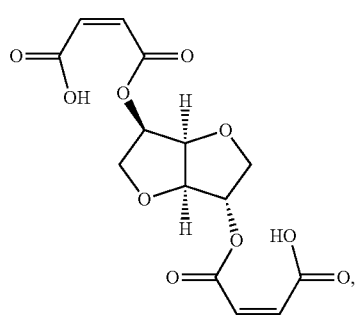
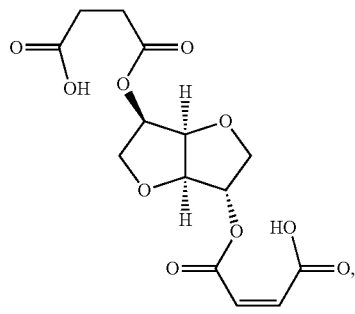
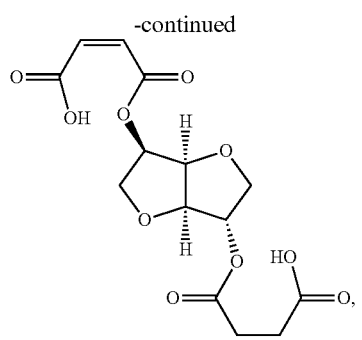
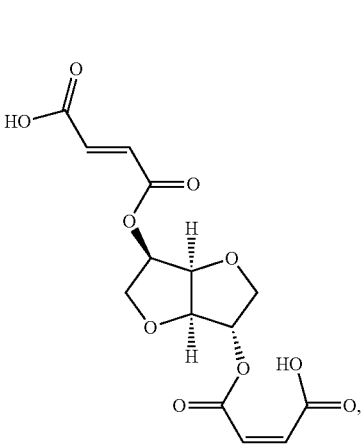
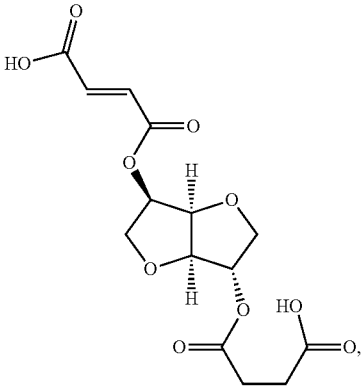
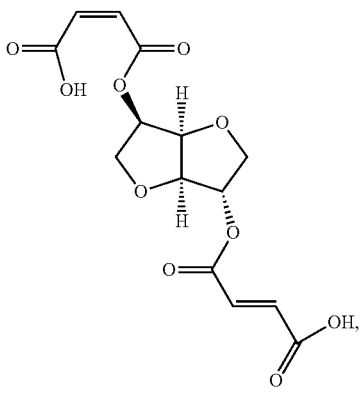

19
-continued
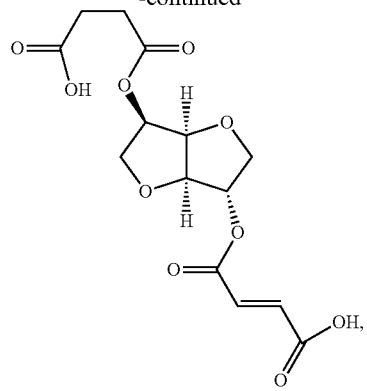
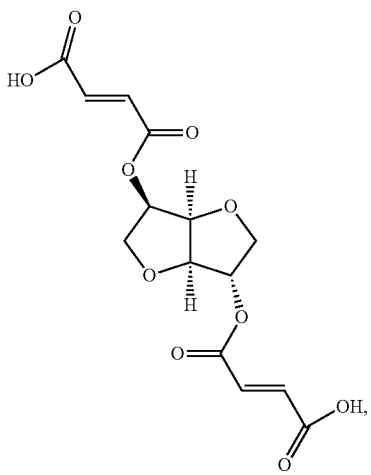
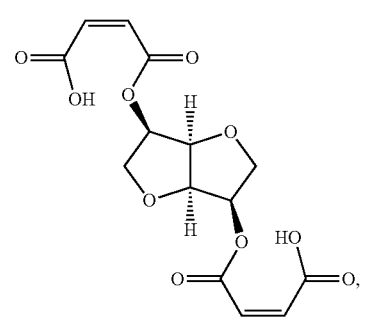
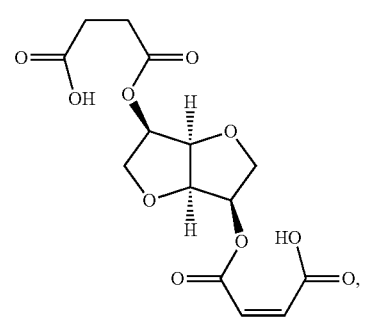
20
-continued
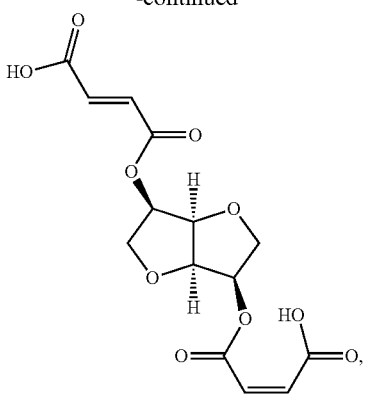
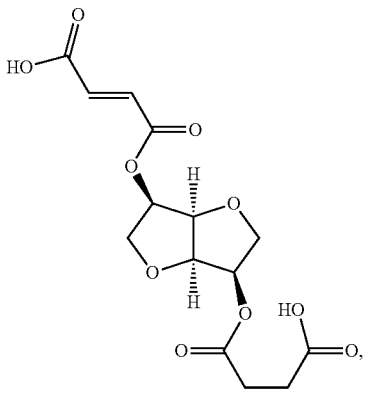
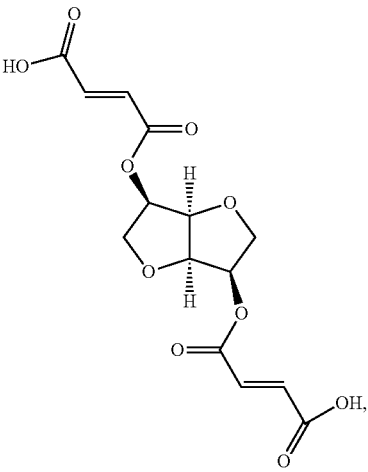
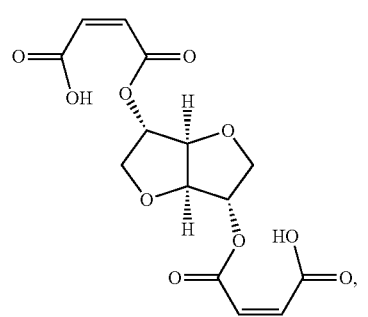

-continued

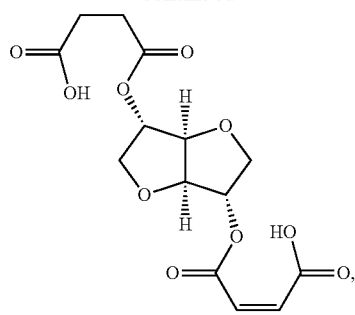

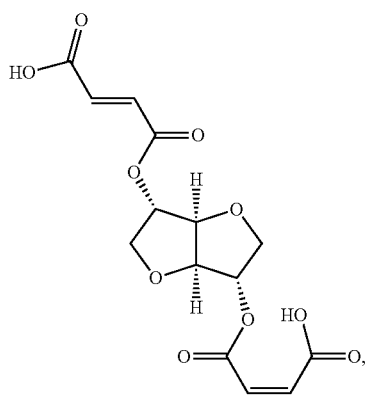

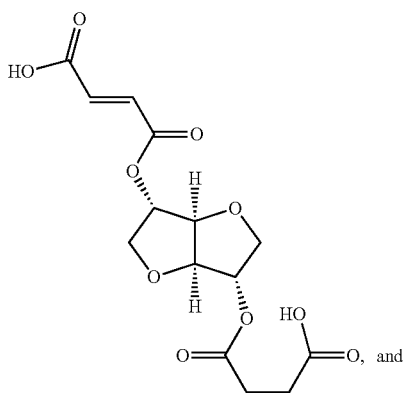

-continued

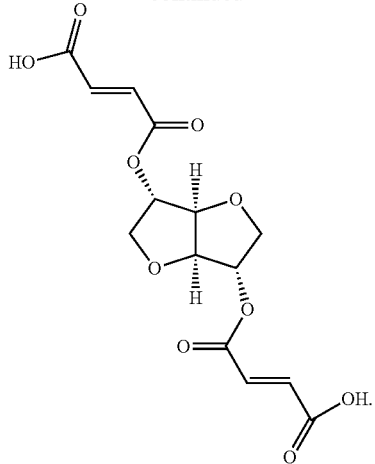

Polymer.

In various embodiments, the present invention provides a polymer. The polymer can be any suitable polymer that can be formed by crosslinking one or more embodiments of the aziridinated triglyceride described herein, such as via one or more polycarboxylic acids.

In various embodiments, the polymer has the structure:

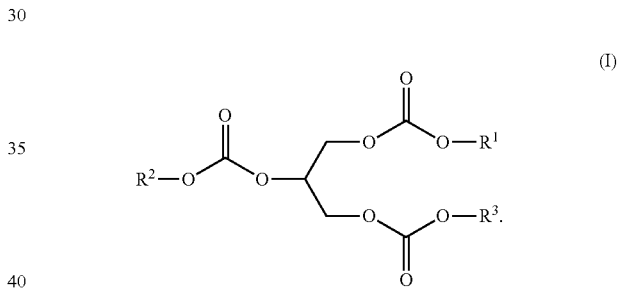

(I)

The variables $R^1$, $R^2$, and $R^3$ correspond to $R^1$, $R^2$, and $R^3$ in the aziridinated triglyceride described herein, but are interrupted or terminated with -AZP— instead of -AZ—. The variables $R^1$, $R^2$, and $R^3$ can each be independently a substituted or unsubstituted $(C_1-C_{50})$hydrocarbyl optionally interrupted or terminated by the A end of at least one -AZP— group having the structure:

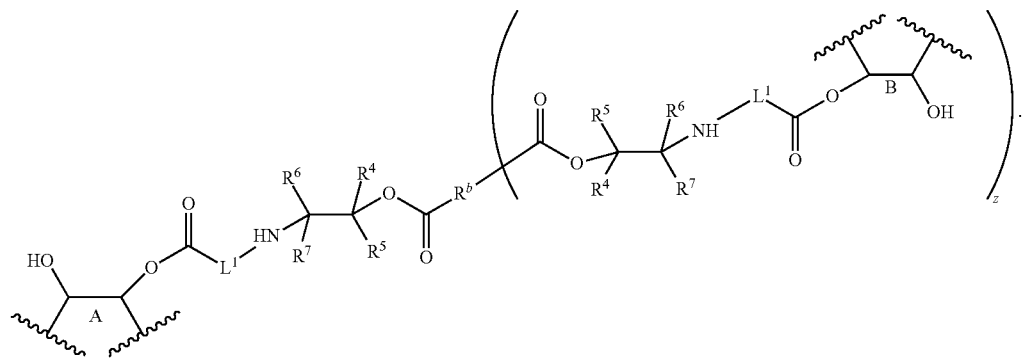

The variable $L^1$ can be independently a substituted or unsubstituted $(C_2-C_{50})$hydrocarbyl interrupted or terminated with 0, 1, 2, or 3 groups independently chosen from —O—, —S—, and substituted or unsubstituted —NH—. The variables $R^4$, $R^5$, $R^6$, and $R^7$ can be independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. The variable $R^b$ can be a substituted or unsubstituted $(C_1-C_{50})$hydrocarbyl having a valence of z+1, wherein $R^b$ can be interrupted or terminated by 0, 1, 2, or 3 groups independently chosen from —O—, —S—, substituted or unsubstituted —NH—, and —(O—$(C_2-C_3)$alkylene)$_n$- wherein n is about 1 to about 10,000 (e.g., about 1, 2, 3, 4, 5, 6, 7, 8, 9, 10, 11, 12, 14, 16, 18, 20, 25, 30, 35, 40, 45, 50, 60, 70, 80, 90, 100, 200, 500, 1,000, 2,000, 5,000, or about 10,000 or more) and wherein the $(C_2-C_3)$alkylene is substituted or unsubstituted (e.g., poly(ethyleneoxide) or poly(propyleneoxide). The variable z can be about 1 to about 1,000 (e.g., about 1, 2, 3, 4, 5, 6, 7, 8, 9, 10, 11, 12, 14, 16, 18, 20, 25, 30, 35, 40, 45, 50, 60, 70, 80, 90, 100, 200, 500, or about 1,000 or more). The triglyceride I can include at least one of the -AZP— groups. Each B end of the -AZP— group can independently interrupting or terminating $R^1$, $R^2$, or $R^3$ of the same or different triglyceride I, wherein at least one B end of at least one -AZP— group in the triglyceride I interrupts or terminates $R^1$, $R^2$, or $R^3$ of a different triglyceride I.

The polymer can be any suitable size and molecular weight, and can have any suitable degree of polymerization. In some embodiments, the polymer has about 2 to about 100,000,000 triglycerides of structure I, or about 2, 3, 4, 5, 6, 8, 10, 12, 14, 16, 18, 20, 25, 30, 35, 40, 45, 50, 60, 70, 80, 90, 100, 150, 200, 250, 500, 1,000, 1,500, 2,000, 2,500, 5,000, 10,000, 15,000, 20,000, 25,000, 50,000, 75,000, 100,000, 150,000, 200,000, 250,000, 500,000, 750,000, 1,000,000, 5,000,000, 10,000,000, 50,000,000, or about 100,000,000 or more.

The variables $R^1$, $R^2$, and $R^3$ can each be independently a substituted or unsubstituted $(C_1-C_{50})$hydrocarbyl optionally interrupted or terminated by the A end of at least one -AZP— group. The variables $R^1$, $R^2$, and $R^3$ can each be independently a substituted or unsubstituted $(C_{10}-C_{50})$hydrocarbyl optionally interrupted or terminated by at least one -AZP— group. The variables $R^1$, $R^2$, and $R^3$ can each be independently a substituted or unsubstituted $(C_1-C_{50})$alkane optionally interrupted or terminated with at least one of the -AZP— groups. The variables $R^1$, $R^2$, and $R^3$ can each be independently a $(C_1-C_{50})$alkane optionally interrupted or terminated with at least one of the -AZP— groups, substituted with 0, 1, 2, 3, 4, or 5 epoxy groups, and otherwise unsubstituted. The variables $R^1$, $R^2$, and $R^3$ can each be independently an unsubstituted $(C_1-C_{50})$alkane optionally interrupted or terminated with at least one of the -AZP— groups.

The variable $L^1$ can be independently a substituted or unsubstituted $(C_2-C_{50})$hydrocarbyl interrupted or terminated with 0, 1, 2, or 3 groups independently chosen from —O—, —S—, and substituted or unsubstituted —NH—. At each occurrence, $L^1$ can be independently an unsubstituted $(C_2-C_{50})$alkanylene. At each occurrence, $L^1$ can be independently an unsubstituted $(C_2-C_{10})$alkanylene. At each occurrence, $L^1$ can be independently an unsubstituted $(C_2-C_{10})$alkanylene.

The variables $R^4$, $R^5$, $R^6$, and $R^7$ can be independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—. At each occurrence, $R^4$, $R^5$, $R^6$, and $R^7$ are independently chosen from —H and unsubstituted $(C_1-C_{10})$hydrocarbyl. At each occurrence, $R^5$, $R^6$, and $R^7$ can be —H. At each occurrence, $R^5$, $R^6$, and $R^7$ can be —H, and $R^4$ can be unsubstituted $(C_1-C_{10})$hydrocarbyl. At each occurrence, $R^5$, $R^6$, and $R^7$ can be —H, and $R^4$ can be unsubstituted $(C_1-C_5)$alkyl. At each occurrence, $R^5$, $R^6$, and $R^7$ can be —H, and $R^4$ can be methyl.

The triglyceride I can include at least one of the -AZP— groups. The triglyceride I can include one of the -AZP— groups (e.g., derived from a monoaziridinated triglyceride). The triglyceride I can include two or more of the -AZP— groups (e.g., derived from a multiaziridinated triglyceride). The at least one -AZP— group can interrupt or terminate (e.g., begin, such as -AZP— $R^1$, or end, such as —$R^1$-AZP—H) $R^1$, $R^2$, or $R^3$. The triglyceride I can include any suitable number of the -AZP— groups interrupting or terminating $R^1$, $R^2$, or $R^3$, such as about 1, 2, 3, 4, 5, 6, 7, 8, 9, or about 10 or more. In some embodiments, one or more of $R^1$, $R^2$, and $R^3$ have two or more -AZP— groups. In some embodiments, none of $R^1$, $R^2$, or $R^3$ have more than one -AZP— group each.

In various embodiments, -AZP— has the structure:

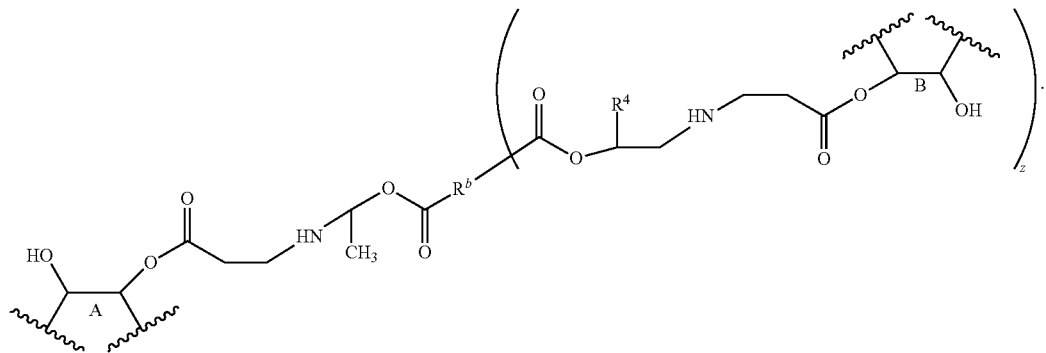

The polymer can be derived from a triglyceride (e.g., an oil), such as any triglyceride starting material described herein. The triglyceride starting material can be epoxidized, treated with a substituted or unsubstituted $(C_3-C_{50})$carboxylic acid including at least one aliphatic unsaturated carbon-carbon bond, and treated with an aziridine, as described herein, to provide an aziridinated triglyceride which can be crosslinked to form the polymer.

In some embodiments, the triglyceride I has the structure:

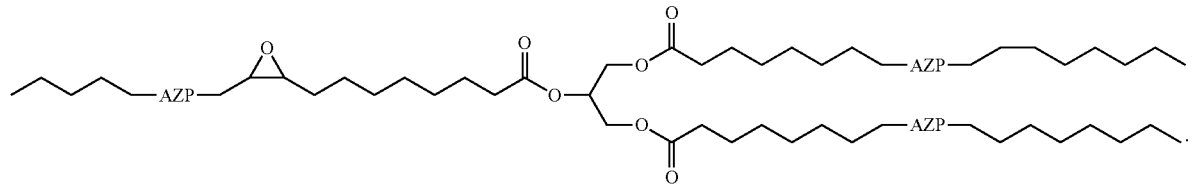

The —O—C(O)—R$^b$(—C(O)—O)$_z$— portion of triglyceride I can correspond to a polycarboxylic acid that has reacted with z+1 aziridine groups, wherein the polycarboxylic acid prior to reaction with the aziridine groups has the structure H—O—C(O)—R$^b$(—C(O)—O)$_z$—H (e.g., R$^b$ can correspond to R$^a$ described herein). The polycarboxylic acid can be any suitable polycarboxylic acid. In some embodiments, the polycarboxylic acid is at least one of a HOC(O)—R$^a$—C(O)OH wherein R$^a$ is a substituted or unsubstituted (C$_1$-C$_{50}$)hydrocarbylene interrupted or terminated by 0, 1, 2, or 3 groups independently chosen from —O—, —S—, substituted or unsubstituted —NH—, and —(O—(C$_2$-C$_3$)alkylene)$_n$- wherein n is about 1 to about 10,000 (e.g., about 1, 2, 3, 4, 5, 6, 7, 8, 9, 10, 11, 12, 14, 16, 18, 20, 25, 30, 35, 40, 45, 50, 60, 70, 80, 90, 100, 200, 500, 1,000, 2.000, 5.000, or about 10,000 or more) and wherein the (C$_2$-C$_3$)alkylene is substituted or unsubstituted (e.g., poly(ethyleneoxide) or poly(propyleneoxide), oxalic acid, maleic acid, succinic acid, methylsuccinic acid, malonic acid, adipic acid, glutaric acid, fumaric acid, dihydroxyfumaric acid, malic acid, mesaconic acid, itaconic acid, phthalic acid, isophthalic acid, terephthalic acid, 1,2-, 1,3-, or 1,4-cyclohexane dicarboxylic acid, 1,2,3-cyclohexane tricarboxylic acid, 1,2,4-cyclohexane tricarboxylic acid, 1,3,5-cyclohexane tricarboxylic acid, 1.2- or 1,3-cyclopentane dicarboxylic acid, citric acid, tartaric acid, dihydroxyterephthalic acid, 1,2,3-, 1,2,4-, or 1,2,5-benzene tricarboxylic acid, tricarballylic acid, 1,2,4,5-benzene tetracarboxylic acid, norbornene tetracarboxylic acid, 3,3',4,4'-benzophenone tetracarboxylic acid, 1,2,3,4,5,6-benzene hexacarboxylic acid, aspartic acid, polyacrylic acid, and glutamic acid. In various embodiments, the polycarboxylic acid is succinic acid, citric acid, an isosorbide-based diacid, or a combination thereof.

In some embodiments, the polycarboxylic acid has the structure:

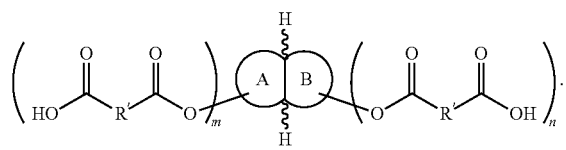

Fused rings A and B can be each independently chosen from substituted or unsubstituted (C$_5$-C$_{10}$)cycloalkyl and (C$_2$-C$_{10}$)heterocyclyl. The variables m and n can each be independently about 1 to about 8. At each occurrence R' can be independently chosen from substituted or unsubstituted (C$_2$-C$_{10}$)hydrocarbylene.

At each occurrence R' can be independently chosen from substituted or unsubstituted (C$_2$-C$_{10}$)hydrocarbylene. At each occurrence R' can be independently unsubstituted. At each occurrence R' can be independently chosen from (C$_1$-C$_5$)alkylene. (C$_5$-C$_{10}$)aryl, and (C$_2$-C$_5$)alkenylene. At each occurrence R' can be independently chosen from —CH$_2$—CH$_2$—, —CH$_2$—CH$_2$—CH$_2$—, o-phenylene, and —CH=CH—.

The variables m and n can each be independently about 1 to about 8, such as about 1, 2, 3, 4, 5, 6, 7, or about 8. In some embodiments, m can have the same value as n. The variables m and n can both be 1.

Fused rings A and B can be each independently chosen from substituted or unsubstituted (C$_5$-C$_{10}$)cycloalkyl and (C$_2$-C$_{10}$)heterocyclyl. Rings A and B are unsubstituted with the exception of the one or more ester substituents —OC(O)—R'—C(O)OH. The variables m and n can each be 1, and one of the ester substituents including R' can be alpha to at least one carbon atom shared by rings A and B. Rings A and B can be the same size. Rings A and B can be 5-membered rings. At least one of rings A and B can include at least one oxygen atom. Each of rings A and B can be a tetrahydrofuran ring, wherein each carbon atom shared by rings A and B has an oxygen atom alpha thereto. In some embodiments, each of the ester substituents —OC(O)—R'—C(O)OH are alpha to a different carbon atom shared by each of rings A and B. Rings A and B can form a ring system chosen from isosorbide, isomannide, and isoidide. Rings A and B can be unsubstituted, other than the ester substituents, —OC(O)—R'—C(O)OH.

In various embodiments, the polycarboxylic acid can have the structure:

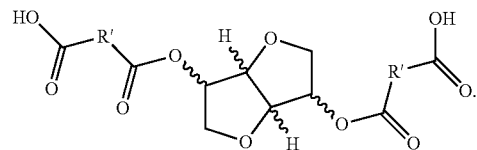

In various embodiments, the polycarboxylic acid is chosen from:

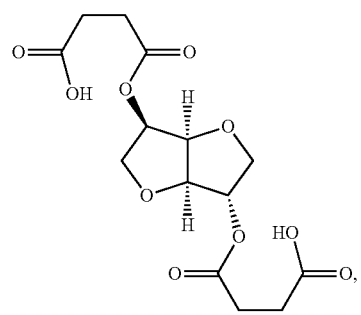

27
-continued
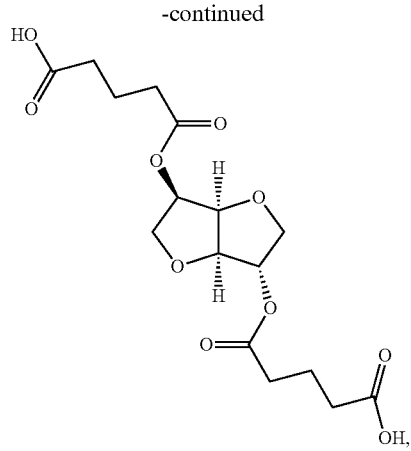
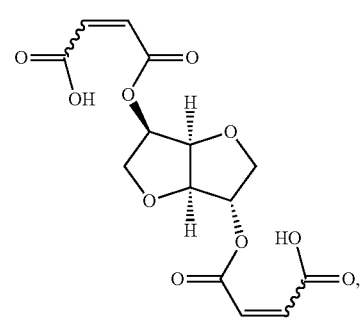
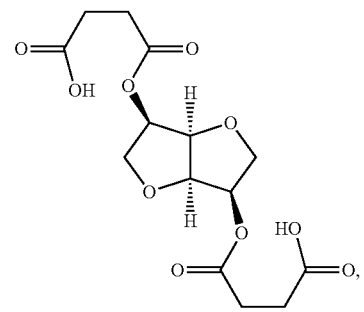
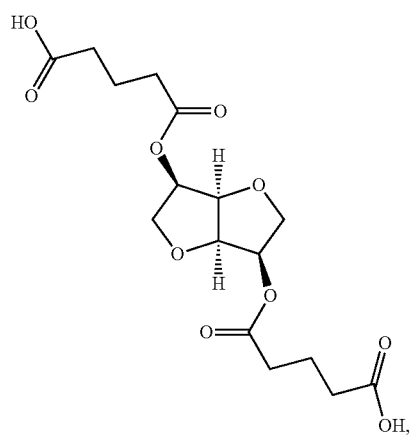
28
-continued
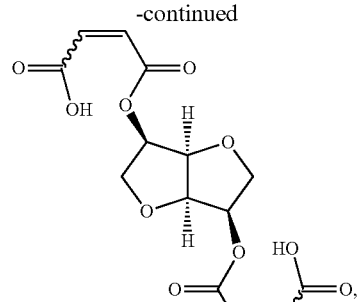
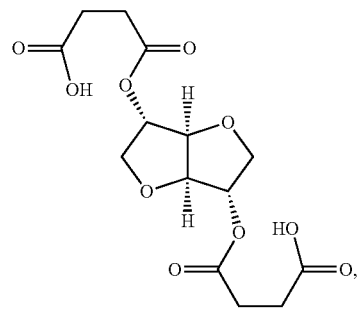
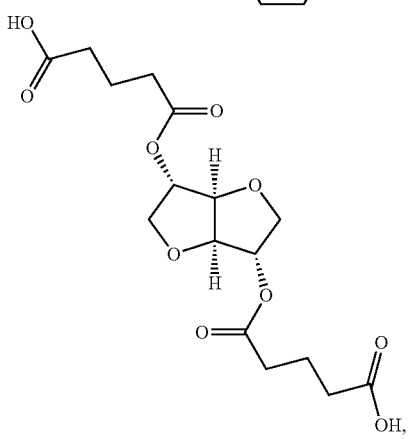
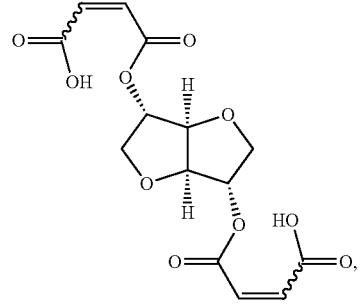
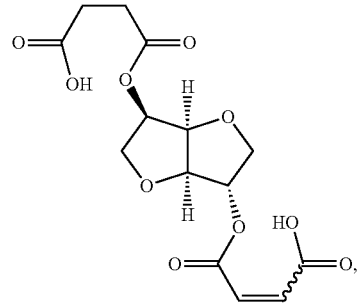

-continued
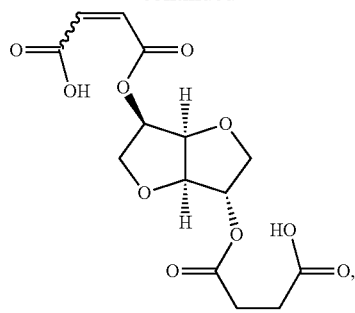
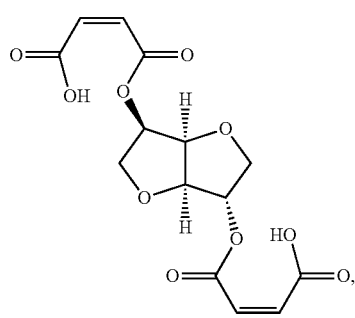
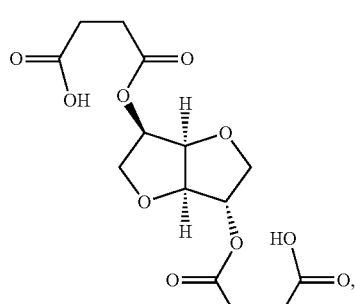
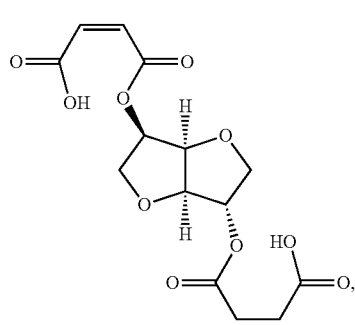
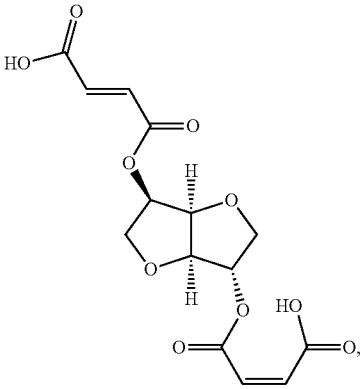
-continued
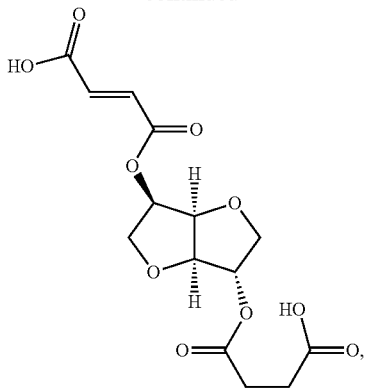
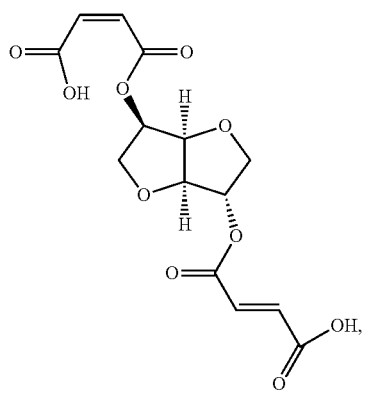
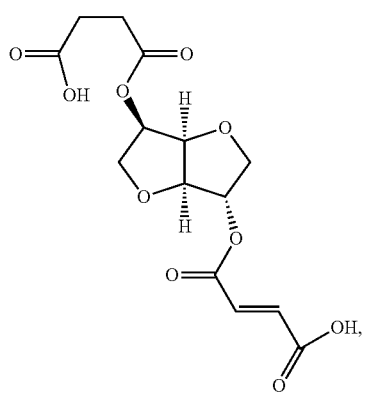
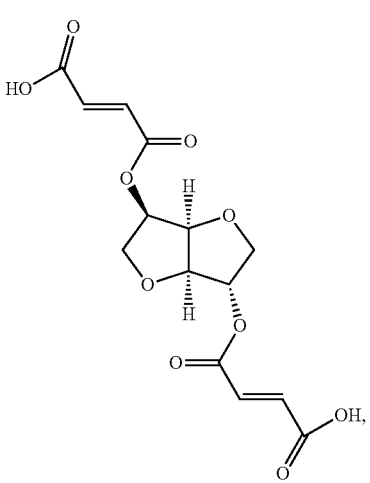

31
-continued
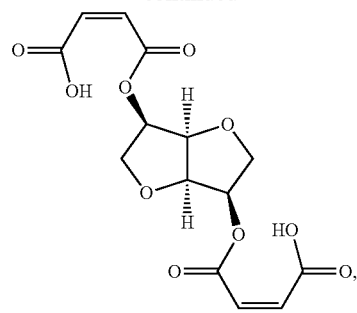
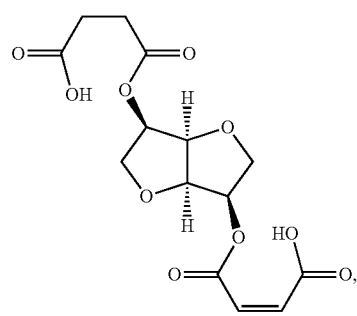
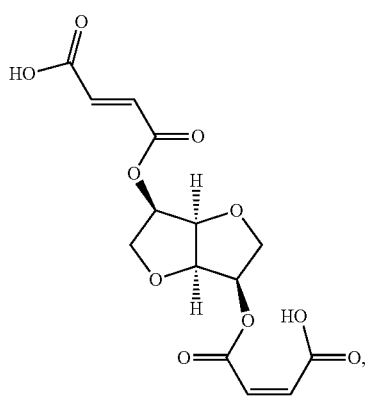
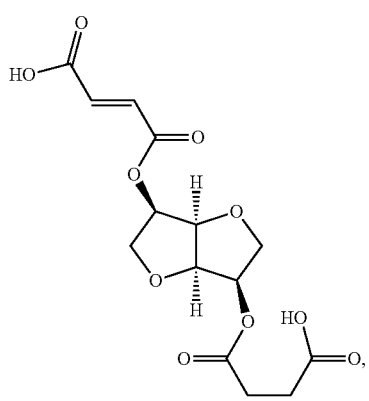
32
-continued
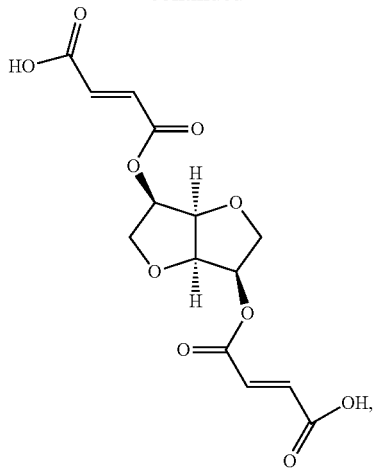
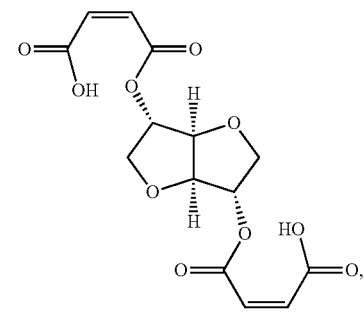
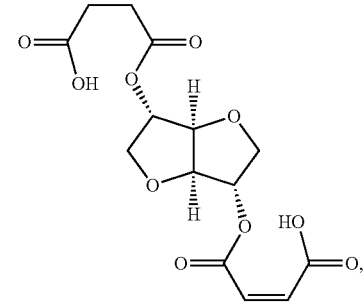
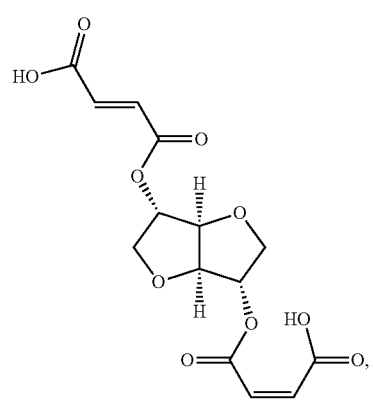

-continued

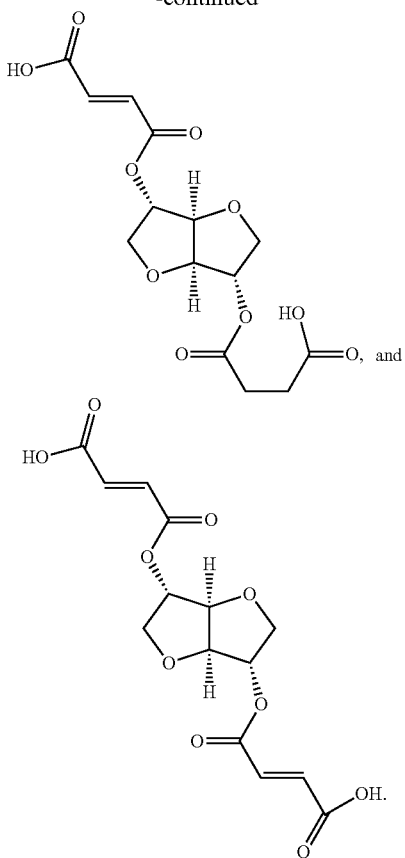

Triglyceride with at Least One Pendent Unsaturated Group.

In various embodiments, the present invention provides a triglyceride with at least one pendent unsaturated group. The pendent unsaturated group can be an α,β-unsaturated aliphatic double bond conjugated with a carbonyl group, such that the double bond is a suitable Michael-acceptor for subsequent reaction with an aziridine. The triglyceride can have the structure:

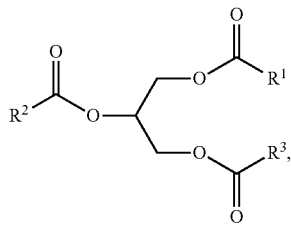

The variables $R^1$, $R^2$, and $R^3$ correspond to $R^1$, $R^2$, and $R^3$ in the aziridinated triglyceride described herein, but are interrupted or terminated with -A- instead of -AZ—. The variables $R^1$, $R^2$, and $R^3$ are each independently a substituted or unsubstituted ($C_1$-$C_{50}$)hydrocarbyl optionally interrupted or terminated by at least one -A- group having the structure:

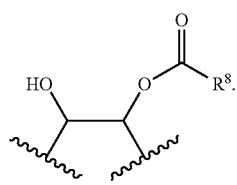

At each occurrence, $R^8$ can be independently a substituted or unsubstituted ($C_2$-$C_{50}$)hydrocarbyl including at least one aliphatic carbon-carbon unsaturated bond and is interrupted or terminated with 0, 1, 2, or 3 groups independently chosen from —O—, —S—, and substituted or unsubstituted —NH—. The variable $R^8$ can be independently an unsubstituted ($C_2$-$C_{20}$)hydrocarbyl including at least one aliphatic carbon-carbon unsaturated bond. The aliphatic carbon-carbon unsaturated bond can be an α,β-unsaturated aliphatic double bond conjugated with a carbonyl group, such that the double bond is a suitable Michael-acceptor for subsequent reaction with an aziridine. The variable $R^8$ can be —CH=$CH_2$. The triglyceride can include at least one of the -A- groups in at least one of $R^1$, $R^2$, and $R^2$. The triglyceride can have any number of -A- groups, such as 1, 2, 3, 4, 5, 6, 7, 8, 9, or 10 or more.

Method of Making Triglyceride with at Least One Pendent Unsaturated Group.

In various embodiments, the present invention provides a method of making the triglyceride having at least one pendent unsaturated group, such as any triglyceride having at least one pendent unsaturated group described herein. The method can be any suitable method of making the triglyceride having the at least one pendent unsaturated group. The method can include combining an epoxidized triglyceride with a substituted or unsubstituted ($C_3$-$C_{50}$)carboxylic acid including at least one aliphatic unsaturated carbon-carbon bond to give the triglyceride having at least one pendent unsaturated group.

EXAMPLES

Various embodiments of the present invention can be better understood by reference to the following Examples which are offered by way of illustration. The present invention is not limited to the Examples given herein.

Materials. Acrylated epoxidized soybean oil (AESO) containing 4000 ppm monomethyl ether hydroquinone as inhibitor, dichloromethane ($CH_2Cl_2$), N,N-dimethylformamide (DMF), succinic acid, citric acid, 2-methylaziridine, 0.1 N perchloric acid concentrate ($HClO_4$), tetrabutylammonium iodide, 0.5% crystal violet solution, chloroform ($CHCl_3$), and tetrahydrofuran (THF) were purchased from Sigma-Aldrich (Milwaukee, Wis.). Ethanol was purchased from Decon Laboratories Inc., King of Prussia, Pa. All materials were used as received without further purification.

Example 1

Preparation of Aziridinated Acrylated Epoxidized Soybean Oil (AESO-AZ)

AESO (20 g) was dissolved in 30 mL dichloromethane and placed in a round-bottom flask. Dichloromethane solution (15 mL) of 2-methylaziridine (5 g) was added drop wise (1 drop/s) through an addition funnel in an ice bath. The reaction mixture was kept at ambient temperature for 18 h after addition. Dichloromethane and excess 2-methylaziridine were removed by roto-evaporation at 68° C. under reduced pressure. The obtained AESO-AZ was oven-dried overnight. The resulting AESO-AZ was a brown, viscous liquid at room temperature. The reaction is shown in Scheme 1.

Scheme 1. Synthesis of AESO-AZ.

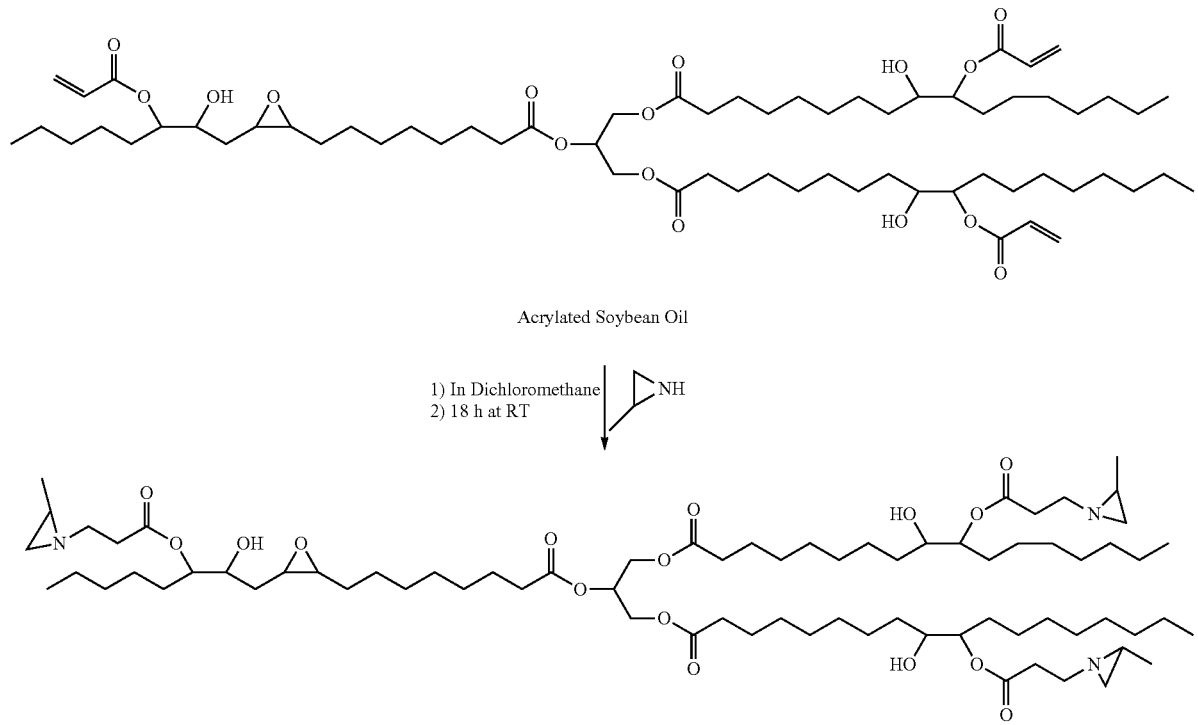

Acrylated Soybean Oil

Example 2

Polymerization of AESO-AZ with Polyacids

Succinic acid, citric acid, and an isosorbide-based diacid, having the structures shown below, were used to polymerize AESO-AZ.

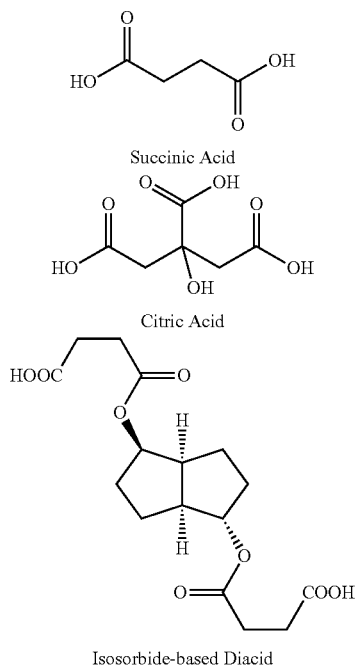

The isosorbide-based diacid was synthesized according to the protocol published in Zenner M D, Xia Y, Chen J S, Kessler M R: Polyurethanes from Isosorbide-Based Diisocyanates, *Chemsuschem* 2013, 6(7): 1182-1185: it was derived from the double esterification of isosorbide by succinic anhydride under solvent-free conditions. DMF solution of AESO-AZ (20%) and a corresponding DMF solution of polyacid (20%) were mixed in vials for 10 min. The mixture was then poured into a Teflon mold (5 in×5 in) and dried at ambient temperature. The mold was placed in an oven at 60° C. for 24 h. The obtained films were transparent, indicating the amorphous nature of the polymer network. The reaction is shown in Scheme 2.

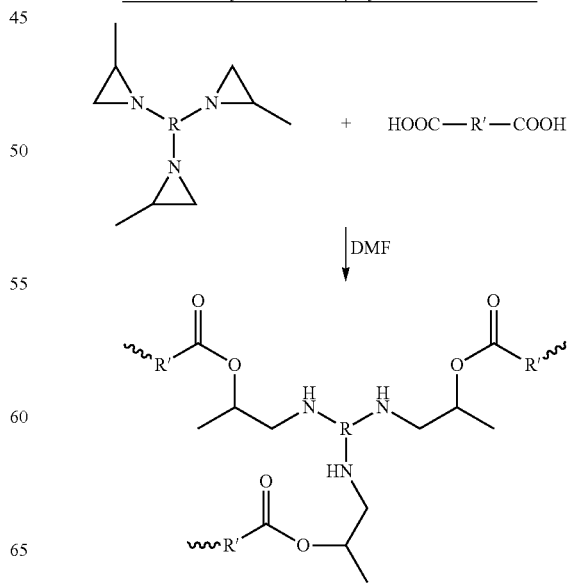

Example 3

Characterization

The aziridine content of AESO-AZ was determined according to the titration method published by Jay R R: Direct Titration of Epoxy Compounds+Aziridines, *Anal Chem* 1964, 36(3):667. Approximately 0.5 g (precisely weighed) of the sample was dissolved in 15 mL chloroform, then 15.00 mL 10% chloroform solution of tetrabutylammonium iodide together with 2 to 3 drops of crystal violet indicator were added. The mixture was titrated with 0.1 N $HClO_4$. A blank sample was used to eliminate background effects. This titration method is also applicable to epoxy groups; therefore, AESO was titrated as well since it contains some residual epoxy groups resulting from the manufacturing process (acrylation of epoxidized soybean oil). $^1H$ NMR spectra of AESO and AESO-AZ were recorded on a Varian spectrometer (Palo Alto, Calif.) at 300 MHz in chloroform-d. The average molecular weight of AESO and AESO-AZ were determined by a Thermo Scientific Dionex Ultimate 3000 GPC (Sunnyvale, Calif.) equipped with a Shodex Refractive Index (RI) at room temperature. Tetrahydrofuran (THF) was used as eluent solvent and the delivery speed was 1.0 mlJmin. The viscosity of AESO-AZ was measured by varying the shear rate from $10\ s^{-1}$ to $1000\ s^{-1}$ on an AR2000 Rheometer (TA Instrument).

The gel content was measured via Soxhlet extraction. A known weight ($W_0$) of pre-conditioned sample was placed in the Soxhlet extractor with continuous THF extraction for 1 d. The remaining sample was dried and weighed as $W_1$. Three tests were performed for each sample. The gel content % was calculated as $(W_1/W_0) \times 100\%$.

Differential scanning calorimetry (DSC) was performed on a TA Instrument Q20. Samples were heated to 100° C. in the first ramp in order to eliminate their heat history. The samples were then cooled down to −50° C. and heated to 100° C., at a rate of 10° C./min. The heat profile of the second heating ramp was recorded and the glass transition temperature was determined using the midpoint inflection method.

A DMA Q800 (TA Instruments) was implemented to record the dynamic thermal mechanical behavior of the samples. Film-tension mode of 1 Hz was used for testing rectangular samples with a dimension of 15 mm×10 mm. The samples were kept isothermally for 3 min at −80° C. followed by a temperature rise to 120° C., at a programmed rate of 3° C./min. Tan δ was calculated as the loss modulus divided by the storage modulus and the glass transition temperatures ($T_g$s) were determined by the peaks of the tan δ curves.

Thermogravimetric analysis (TGA) of the films was conducted on a TA Instrument Q50 (New Castle, Del.). At a constant air flow rate of 60 mL/min. the samples were heated from ambient temperature to 650° C., at a rate of 20° C./min. The decomposition profile was recorded as a function of temperature.

The tensile profiles of the samples were determined using an Instron universal testing machine (model 4502). Rectangular samples of 50 mm×10 mm were subjected to tension at a crosshead speed of 100 mm/min. The tests were replicated at least three times for each sample and the average of the reported values was determined. Toughness was calculated by integrating the area beneath the stress-strain curve.

Example 4

Results and Discussion

Preparation and Properties of AESO-AZ

Michael addition of 2-methylaziridine to acrylic groups on AESO was used to prepare AESO-AZ. An excess amount of 2-methylaziridine was added and the unreacted residual was removed via roto-evaporation, an approach possible because of the low boiling point of 2-methylaziridine (b.p. 66-67 OC). FTIR spectra of AESO and ASEO-AZ are shown in FIG. 1. The disappearance of the peak at 1635 $cm^{-1}$ (blue box) indicated the complete conjugate addition to the acrylic groups. The peak at 3053 $cm^{-1}$ was attributed to the C—H stretching on the aziridine ring. The peaks at 2930 cm-1 and 2850 $cm^{-1}$ (C—H stretching in fatty acid chains) and at 1750 $cm^{-1}$ (C═O stretching of ester groups) remained unchanged after the reaction, indicating that the triglyceride structure of AESO was preserved.

Figure 2:
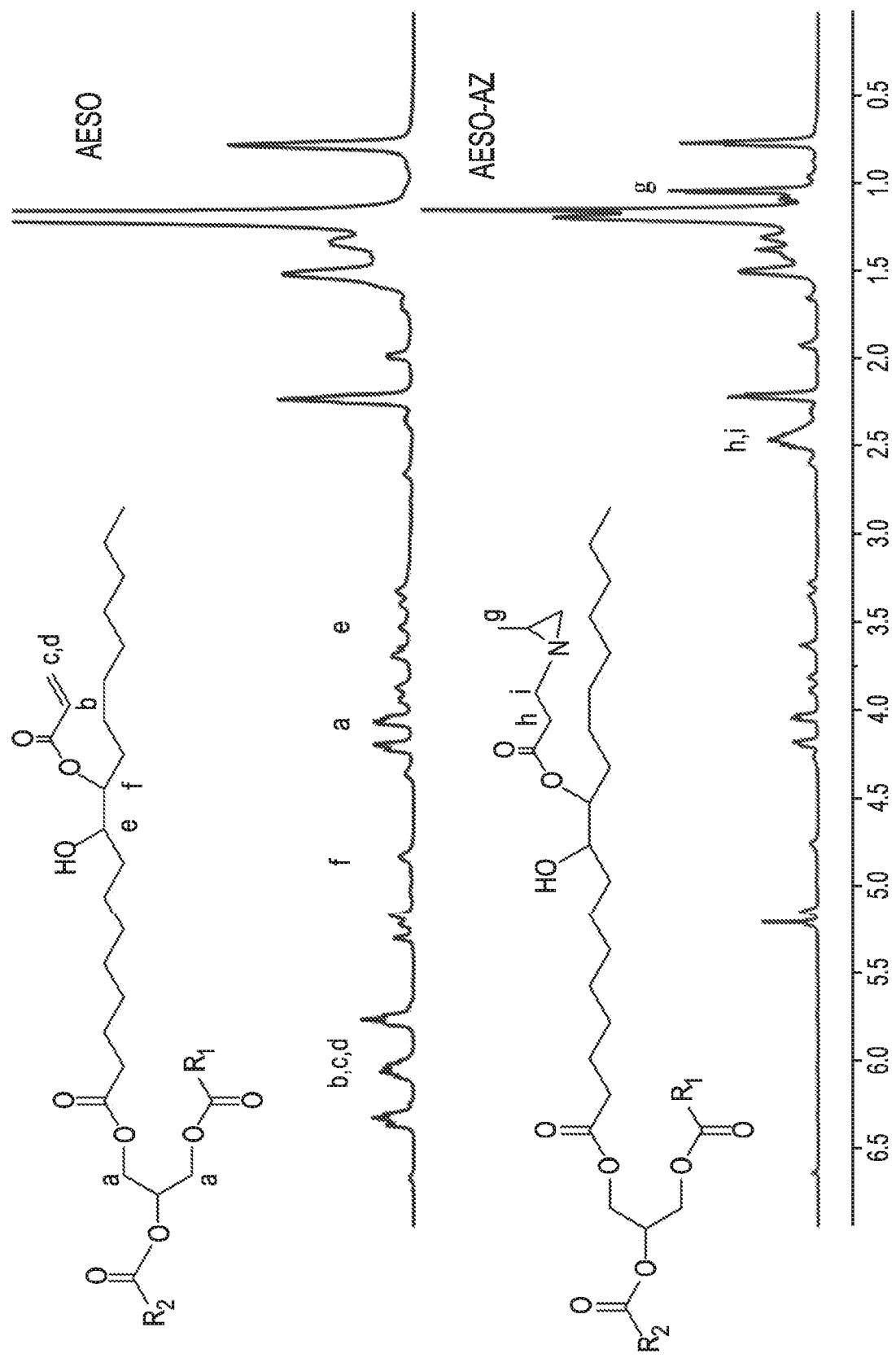
FIG. 2 illustrates $^1$H-NMR spectra of AESO and AESO-AZ, in accordance with various embodiments.

The $^1$H-NMR spectra in FIG. 2 also confirmed the completion of this reaction. Peaks d, e, f, corresponding to the hydrogen atoms on the acrylic group, disappeared after the reaction, which indicated the occurrence of a Michael addition. Peaks g and h in AESO-AZ were attributed to methylene protons that established that the acrylics were saturated after Michael addition. The three hydrogen atoms on the aziridine ring structure could not be clearly observed, but peak i, corresponding to the methyl group of 2-methylaziridine, established that 2-methylaziridine was the nucleophile in the Michael reaction. That the aziridine ring remained intact during the reaction was hard to prove by NMR, but the success of the subsequent polymerization with polyacids provided strong evidence that the aziridine ring was indeed intact. Peaks a, b, and c, associated with the hydrogen atoms labeled on the embedded structure, remained throughout the reaction, further confirming the preservation of the basic structure of AESO.

Figure 3:
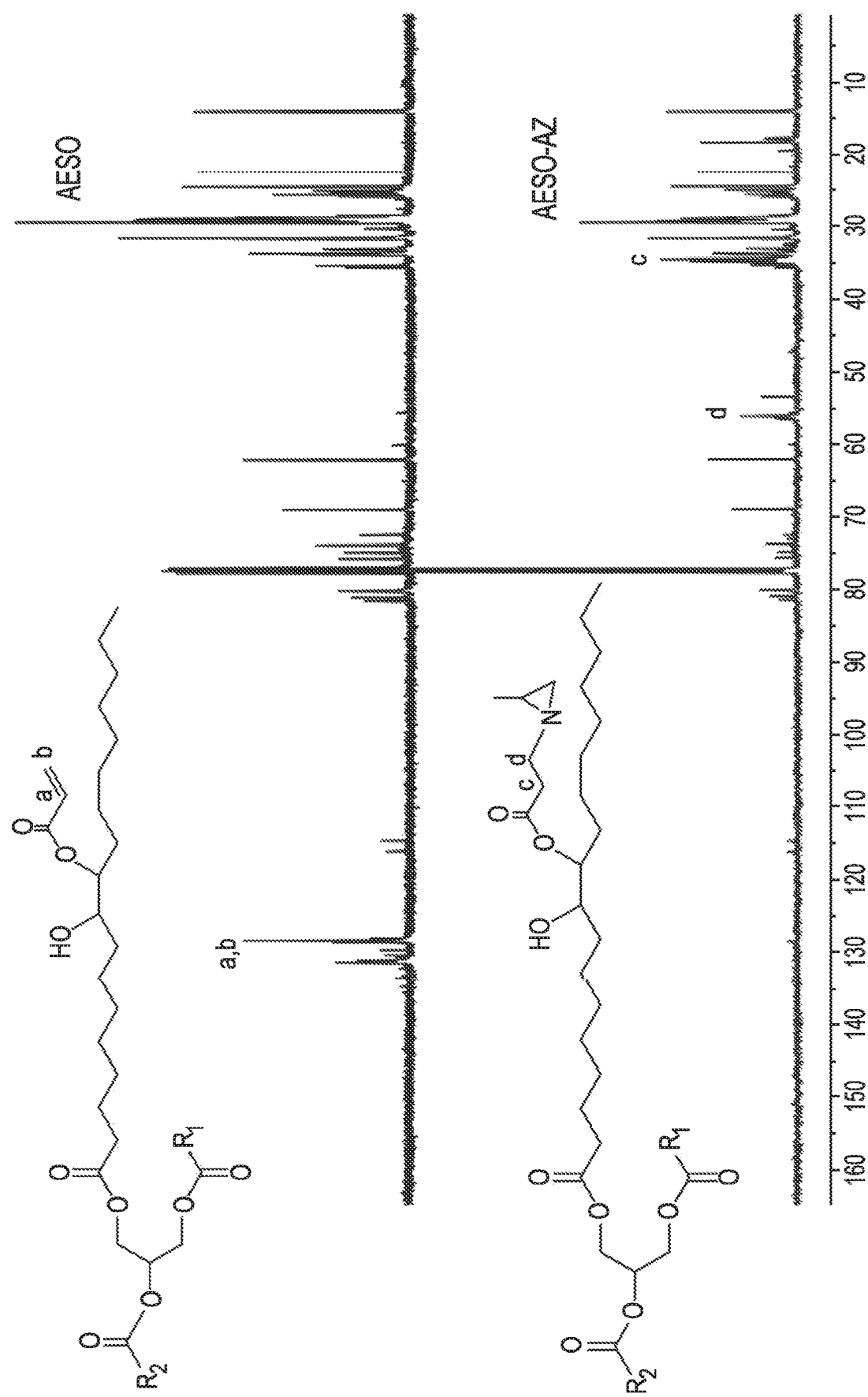
FIG. 3 illustrates $^{13}$C-NMR spectra of AESO and AESO-AZ, in accordance with various embodiments.

$^{13}$C-NMR spectra were obtained for AESO and AESO-AZ. In FIG. 3, the disappearance of peaks a and b and the appearance of peaks c and d illustrated the fact that the acrylic groups of AESO underwent Michael addition with the —NH-bridges of the 2-methylaziridine.

The viscosities of AESO and AESO-AZ at room temperature and the molecular weights $M_n$ and $M_w$ are summarized in Table 1. There was no distinct difference in viscosity between the two specimens, indicating that the intermolecular interactions were not remarkably changed after the reaction. The molecular weight of AESO-AZ was slightly higher than that of AESO because of the addition of 2-methylaziridine.

TABLE 1

Properties of AESO and AESO-AZ.

| | Viscosity (Pa · s) at | $M_n$ | $M_w$ | PDI |
|---|---|---|---|---|
| AESO | 27.3 | 1967 | 2165 | 1.10 |
| AESO-AZ | 29.9 | 2492 | 2665 | 1.07 |

Titration of the aziridine content was critical in order to determine the amount of polyacids required for the polymerization step, because the molar ratio of aziridine and carboxylic acid has to be 1:1. This titration method is also applicable to epoxy. Upon titration. AESO had an epoxy content of $5.55 \times 10^{-5}$ mol/g. Assuming that there was no change in epoxy content after Michael addition, the epoxy content was subtracted from AESO-AZ to get a net content of aziridine. AESO-AZ had an aziridine content of 0.00413 mol/g.

Example 5

Results and Discussion

Polymer Properties

Figure 4:
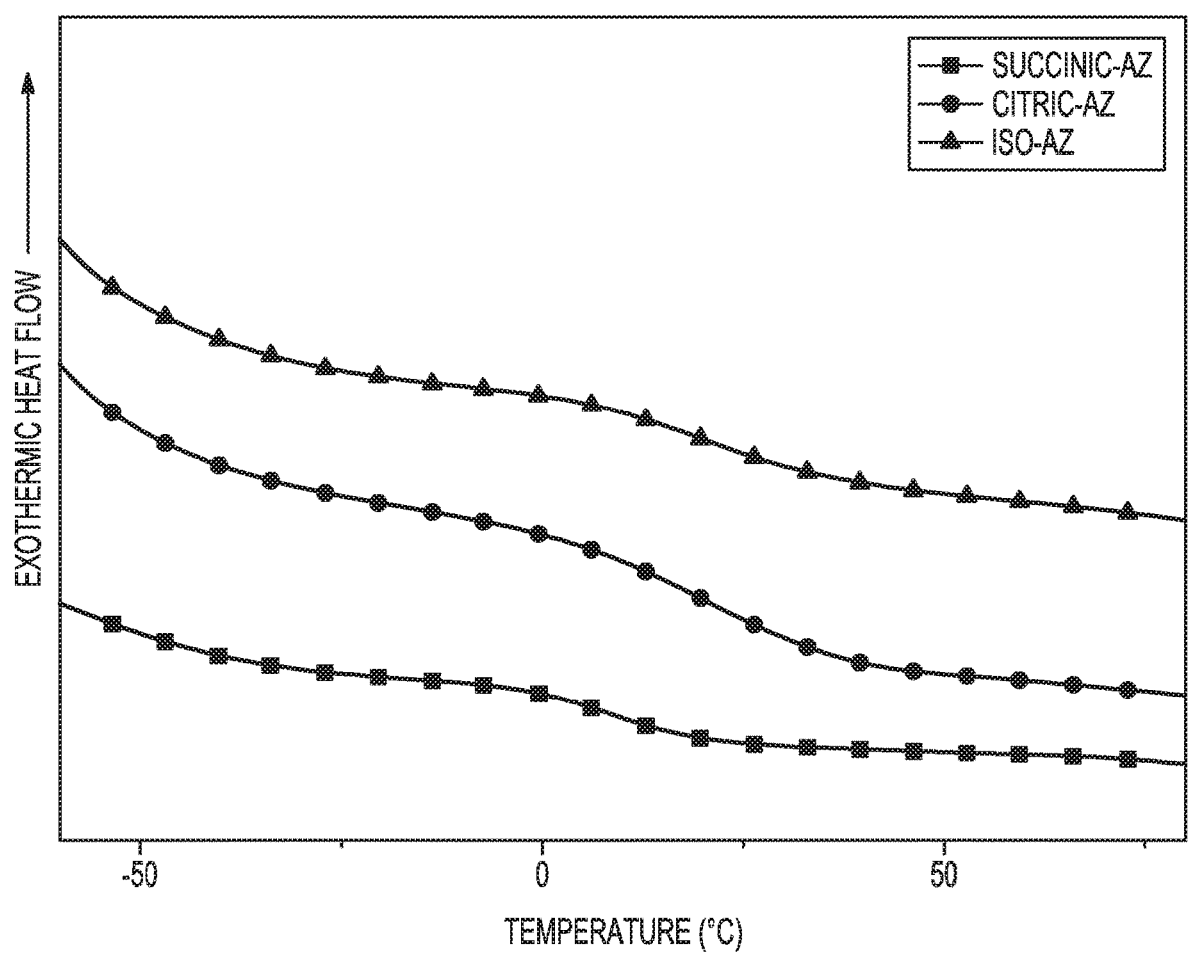
FIG. 4 illustrates DSC curves of succinic acid-crosslinked AESO-AZ (succinic-AZ), citric acid-crosslinked AESO-AZ (citric-AZ), and isosorbide-based diacid-crosslinked AESO-AZ (iso-AZ), in accordance with various embodiments.

Differential scanning calorimetry (DSC) was used to determine the thermal transitions of the polymeric materials and the DSC thermograms of the samples are shown in FIG. 4. Each sample exhibited only one $T_g$, indicating a homogenous structure. In addition, no melting was observed, so all samples were determined to be amorphous. Notice that the polymer derived from succinic acid and AESO-AZ (succinic-AZ) exhibited the lowest $T_g$ at 12.0° C. When succinic acid was replaced by citric acid (citric-AZ) or the isosorbide-based diacid (iso-AZ), the $T_g$ of the respective polymer increased to 20.3° C., and 20.8° C. The increase in $T_g$ of citric-AZ was attributed to a higher crosslinking density. Because citric acid had a functionality of 3, while the functionality of succinic acid was 2, the formation of more crosslinking sites in citric-AZ was expected, resulting in a higher crosslinking density. For iso-AZ, the presence of hard segments contributed to the increased $T_g$. The rigid ring structure introduced by isosorbide remained during polymerization and may have restricted the motion of the polymer chains. The increase in functionality of the citric acid monomer in citric-AZ and the addition of hard segments in iso-AZ had similar effects on $T_g$.

Figure 5:
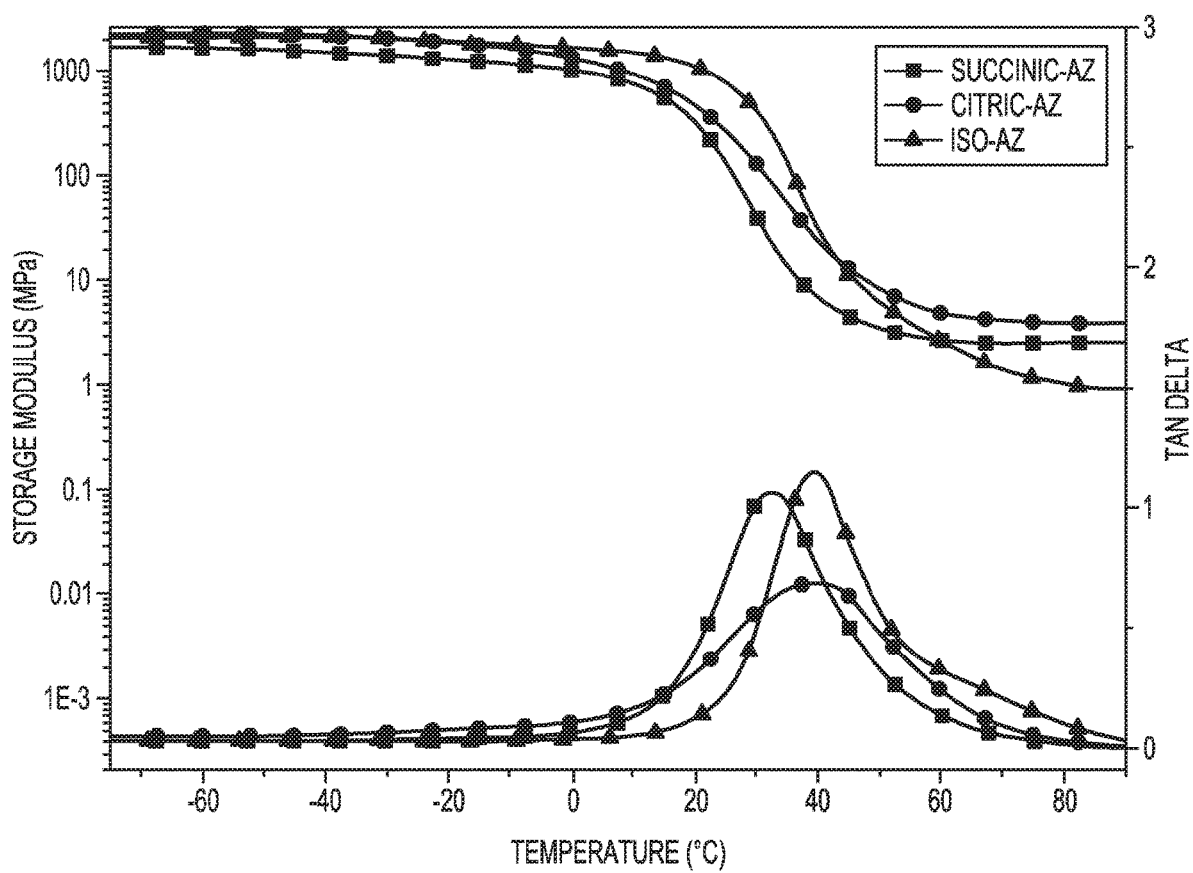
FIG. 5 illustrates the storage modulus and loss factor of succinic-AZ, citric-AZ and iso-AZ as functions of temperature, in accordance with various embodiments.

FIG. 5 shows the storage modulus (E') and the loss factor (tan δ) as functions of temperature. In the low temperature regime, all samples were in a glassy state so that the storage modulus was relatively high because of the low mobility of the polymer chains. In addition. E' dropped slightly before the temperature reached the material's glass transition point at which point the polymer chains were activated. The $T_g$s obtained by DMA were defined by the peak of tan δ. Only one tan δ was observed for each material, indicating the homogeneity of all investigated samples. The $T_g$s of succinic-AZ, citric-AZ, iso-AZ were 32.6° C., 39.7° C., and 38.9° C. respectively. It is worth mentioning that the discrepancy between $T_g$ values obtained by DSC and by DMA is a commonly observed phenomenon caused by the different measuring mechanisms. While DSC measures the heat capacity change from frozen to unfrozen chains, DMA measures the change in mechanical response of the polymer chains to heating. As the temperatures passed the glass transition point, all samples entered into the rubbery state and E' exhibited less dependence on temperature. A rubbery plateau was observed, strongly indicating the presence of a crosslinked network. The value of E' at $T_g+50°$ C., can be used to determine the crosslinking density ($v_e$), where E' $3v_e RT$, where R is the universal gas constant, and T is the absolute temperature. The calculated crosslinking density for succinic-AZ, citric-AZ, iso-AZ were 287.4 mol/m³, 468.5 mol/m³, and 107.4 mol/m³, respectively, see Table 2. In addition, the height of tan δ decreased with increasing crosslinking density, matching the calculated results. The difference in crosslinking density between citric-AZ and succinic-AZ was caused by the difference in functionality (3 vs. 2). The higher functionality created more crosslinking sites, creating a denser network. Although isosorbide-based diacid has the same functionality as succinic acid, iso-AZ exhibited a lower crosslinking density than succinic-AZ, which was attributed to the presence of the rigid isosorbide ring interrupting the crosslinking network. In addition, the rigid ring in isosorbide-based diacid may have restricted the compactness of the network.

The gel content of all samples was close to or higher than 90% (see Table 2), indicating the presence of a highly crosslinked polymer network in each sample. The thermosetting behavior of the samples also confirmed successful polymerization.

Figure 6:
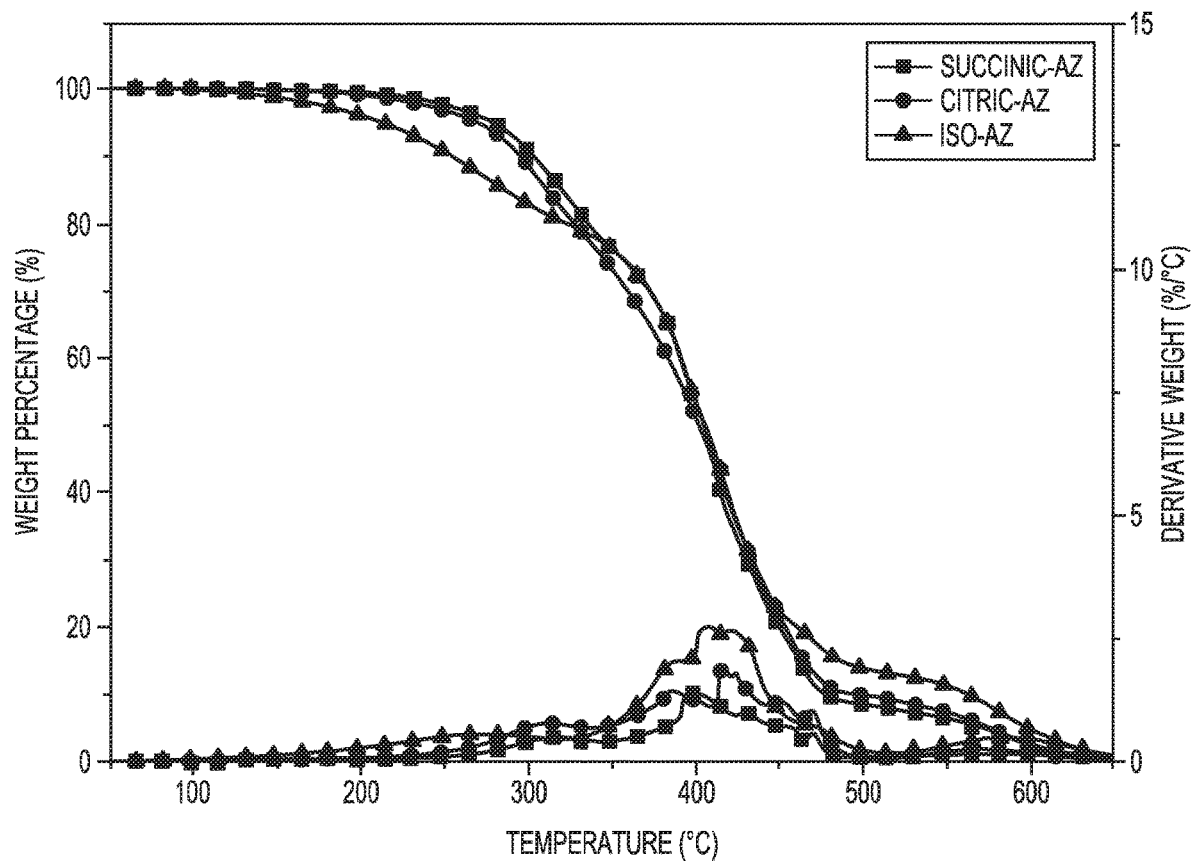
FIG. 6 illustrates thermogravimetric analysis (TGA) curves their derivative curves for succinic-AZ, citric-AZ and iso-AZ, in accordance with various embodiments.

The thermal resistance of the samples was investigated by TGA, see FIG. 6. All samples underwent three stages of thermal decomposition in air atmosphere. The first weight loss occurred between 100 and 350° C., and was assigned to the dissociation of labile bonds, such as ester groups and secondary amine groups. Succinic-AZ and citric-AZ exhibited similar decomposition profiles, because they were derived from similar, small aliphatic polyacids and differed only in functionality. Decomposition onset of iso-AZ occurred at lower temperatures and was attributed to the instability of isosorbide-based diacid, which underwent ester group dissociation at temperatures above 100° C. The second thermal degradation stage between 350 and 450° C., was attributed to chain scission in the soybean oil structure. The last stage, above 450° C., was caused by further thermo-oxidation of the samples due to the presence of oxygen in air atmosphere. The temperatures of 10% and 50% weight loss. $T_{10}$ and $T_{50}$ respectively, are summarized in Table 2. Iso-AZ exhibited the lowest $T_{10}$ because of the low thermal resistance of the ester bond attached to the isosorbide ring. The $T_{50}$s for all samples were similar as these temperatures reached the regime of chain scission for the triglyceride structures.

TABLE 2

Summary of physical and thermal properties.

| | Gel Content | $T_g$ (° C.) | $T_g$ (° C.) | $v_e$ (mol/m³) | $T_{10}$ (° C.) | $T_{50}$ (° C.) |
|---|---|---|---|---|---|---|
| Succinic-AZ | 94.3 | 12.0 | 32.6 | 287.4 | 301.8 | 402.9 |
| Citric-AZ | 93.8 | 20.3 | 39.7 | 468.5 | 293.1 | 400.6 |
| Iso-AZ | 90.9 | 20.8 | 38.9 | 107.4 | 253.3 | 405.6 |

Figure 7:
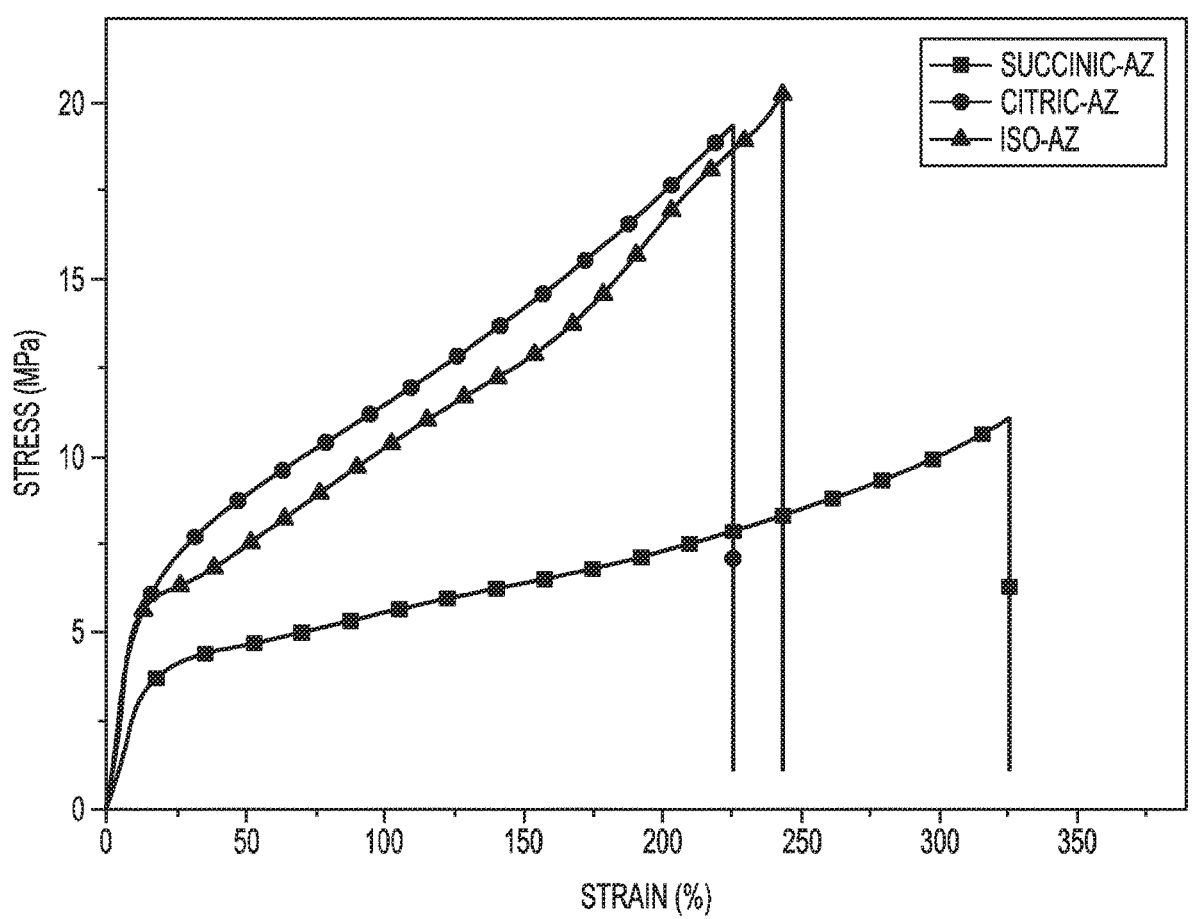
FIG. 7 illustrates stress-strain curves for succinic-AZ, citric-AZ and iso-AZ, in accordance with various embodiments.

Tensile profiles for all samples are plotted in FIG. 7. Young's moduli, tensile strength at break, elongation at break, and toughness are summarized in Table 3. Citric-AZ and iso-AZ were stiffer and stronger compared to succinic-AZ. The relatively higher crosslinking density of citric-AZ provided better resistance to deformation and thus resulted in higher Young's modulus than succinic-AZ. The low crosslinking density of iso-AZ was compensated by the presence of the rigid ring. Succinic-AZ exhibited the highest ductility of all samples, following a common rule that weaker materials exhibit higher ductility. All samples showed comparable toughness.

TABLE 3

Summary of mechanical properties.

| | E | $\sigma_b$ (MPa) | $\varepsilon_b$ (%) | Toughness |
|---|---|---|---|---|
| Succinic-AZ | 35.6 | 11.0 | 327.3 | 22.2 |
| Citric-AZ | 61.0 | 19.4 | 225.9 | 27.2 |
| Iso-AZ | 84.4 | 20.3 | 244.3 | 28.6 |

Example 6

Results and Discussion

Conclusions

Successful Michael addition under mild reaction conditions resulted in the grafting of 2-methyl aziridine onto acrylated epoxidized soybean oil, and the azidirine content was titrated as 0.00413 mol/g. The clean and complete incorporation of 2-methylaziridine into the product was confirmed by FTIR, $^1$H-NMR and $^{13}$C-NMR. Multiaziridine-containing acrylated epoxidized soybean oil (AESO-AZ) was then subjected to rapid room-temperature polymerization with succinic acid, citric acid, and an isosorbide-based diacid, respectively. The polyacids were added to AESO-AZ at stoichiometric ratios. Polymeric materials were successfully obtained. The process took place rapidly and films were obtained by evaporation of the solvents. Differential scanning calorimetry (DSC), dynamic mechanical analysis (DMA), thermogravimetric analysis (TGA), and tensile stress-strain tests were performed. Generally, the glass transition temperatures of citric-AZ and iso-AZ were higher than that of succinic-AZ, which was attributed to a difference in functionality of the respective acids. Citric acid has a functionality of 3, while succinic acid has a functionality of 2. High functionality results in higher crosslinking density, which contributes to the higher $T_g$. Though isosorbide-based diacid has the same functionality as succinic acid, the presence of a rigid ring derived from isosorbide increased the $T_g$. The higher Young's moduli and higher tensile strength of citric-AZ and iso-AZ were attributed to the same effect. Succinic-AZ was the most ductile polymeric material, resulting from the highest mobility of its polymer chains. The glass transition temperatures ($T_g$) of the samples suggested that increased functionality of the carboxylic acid groups in the polyacids may have effectively increased $T_g$, while the rigid rings in isosorbide did not have significant impact on $T_g$.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides an aziridinated triglyceride having the structure:

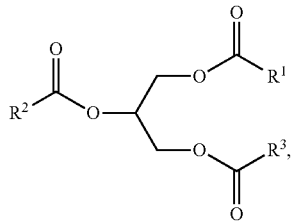

wherein $R^1$, $R^2$, and $R^3$ are each independently a substituted or unsubstituted $(C_1-C_{50})$hydrocarbyl optionally interrupted or terminated by at least one -AZ— group having the structure:

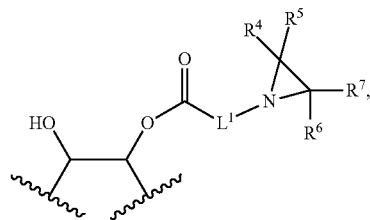

at each occurrence, $L^1$ is independently a substituted or unsubstituted $(C_2-C_{50})$hydrocarbyl interrupted or terminated with 0, 1, 2, or 3 groups independently chosen from —O—, —S—, and substituted or unsubstituted —NH—, at each occurrence, $R^4$, $R^5$, $R^6$, and $R^7$ are independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—, and the aziridinated triglyceride comprises at least one of the -AZ— groups.

Embodiment 2 provides the aziridinated triglyceride of Embodiment 1, wherein at least one of $R^1$, $R^2$, and $R^3$ is interrupted or terminated with at least one of the -AZ— groups.

Embodiment 3 provides the aziridinated triglyceride of any one of Embodiments 1-2, wherein the aziridinated triglyceride comprises at least two of the -AZ— groups.

Embodiment 4 provides the aziridinated triglyceride of any one of Embodiments 1-3, wherein $R^1$, $R^2$, and $R^3$ are each independently a substituted or unsubstituted $(C_{10}-C_{50})$ hydrocarbyl optionally interrupted or terminated by at least one -AZ— group.

Embodiment 5 provides the aziridinated triglyceride of any one of Embodiments 1-4, wherein $R^1$, $R^2$, and $R^3$ are each independently a substituted or unsubstituted $(C_1-C_{50})$ alkane optionally interrupted or terminated with at least one of the -AZ— groups.

Embodiment 6 provides the aziridinated triglyceride of any one of Embodiments 1-5, wherein $R^1$, $R^2$, and $R^3$ are each independently a $(C_1-C_{50})$alkane optionally interrupted or terminated with at least one of the -AZ— groups, substituted with 0, 1, 2, 3, 4, or 5 epoxy groups, and otherwise unsubstituted.

Embodiment 7 provides the aziridinated triglyceride of any one of Embodiments 1-6, wherein $R^1$, $R^2$, and $R^3$ are each independently an unsubstituted $(C_1-C_{50})$alkane optionally interrupted or terminated with at least one of the -AZ— groups.

Embodiment 8 provides the aziridinated triglyceride of any one of Embodiments 1-7, wherein at each occurrence, $L^1$ is independently an unsubstituted $(C_2-C_{50})$alkanylene.

Embodiment 9 provides the aziridinated triglyceride of any one of Embodiments 1-8, wherein at each occurrence, $L^1$ is independently an unsubstituted $(C_2-C_{10})$alkanylene.

Embodiment 10 provides the aziridinated triglyceride of any one of Embodiments 1-9, wherein at each occurrence, $L^1$ is independently an unsubstituted $(C_2-C_{10})$alkanylene.

Embodiment 11 provides the aziridinated triglyceride of any one of Embodiments 1-10, wherein at each occurrence, $R^4$, $R^5$, $R^6$, and $R^7$ are independently chosen from —H and unsubstituted $(C_1-C_{10})$hydrocarbyl.

Embodiment 12 provides the aziridinated triglyceride of any one of Embodiments 1-11, wherein at each occurrence, $R^5$, $R^6$, and $R^7$ are —H.

Embodiment 13 provides the aziridinated triglyceride of any one of Embodiments 1-12, wherein at each occurrence, $R^5$, $R^6$, and $R^7$ are —H, and $R^4$ is unsubstituted $(C_1-C_{10})$hydrocarbyl.

Embodiment 14 provides the aziridinated triglyceride of any one of Embodiments 1-13, wherein at each occurrence, $R^5$, $R^6$, and $R^7$ are —H, and $R^4$ is unsubstituted $(C_1-C_5)$alkyl.

Embodiment 15 provides the aziridinated triglyceride of any one of Embodiments 1-14, wherein at each occurrence, $R^5$, $R^6$, and $R^7$ are —H, and $R^4$ is methyl.

Embodiment 16 provides the aziridinated triglyceride of any one of Embodiments 1-15, wherein -AZ— has the structure:

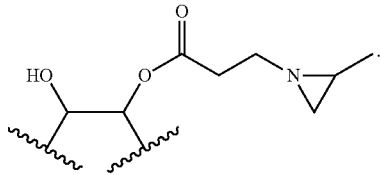 [SMILES: *C(O)C(*)OC(=O)CCN1CC1C]

Embodiment 17 provides the aziridinated triglyceride of any one of Embodiments 1-16, wherein the aziridinated triglyceride is derived from açaí oil, almond oil, amaranth oil, apple seed oil, apricot oil, argan oil, avocado oil, babassu oil, beech nut oil, ben oil, bitter gourd oil, black seed oil, blackcurrant seed oil, borage seed oil, borneo tallow nut oil, bottle gourd oil, buffalo gourd oil, butternut squash seed oil, camelina *sativa* oil, cape chestnut oil, carob pod oil, cashew oil, cocklebur oil, cocoa butter, coconut oil, cohune oil, coriander seed oil, corn oil, cottonseed oil, date seed oil, dika oil, egusi seed oil, evening primrose oil, flaxseed oil, grape seed oil, grapefruit seed oil, hazelnut oil, hemp oil, kapok seed oil, kenaf seed oil, *lallemantia* oil, linseed oil, macadamia oil, mafura oil, marula oil, meadowfoam seed oil, mongongo nut oil, mustard oil, niger seed oil, okra seed oil, olive oil, orange oil, palm oil, *papaya* seed oil, peanut oil, pecan oil, pequi oil, *perilla* seed oil, persimmon seed oil, pili nut oil, pistachio oil, pomegranate seed oil, poppyseed oil, prune kernel oil, pumpkin seed oil, *quinoa* oil, ramtil oil, rapeseed oil, rice bran oil, royle oil, safflower oil, sapote oil, seje oil, sesame oil, shea butter, soybean oil, sunflower oil, taramira oil, tea seed oil, thistle oil, tigernut oil, tobacco seed oil, tomato seed oil, walnut oil, watermelon seed oil, wheat germ oil, agarwood oil, allspice oil, almond oil, anise oil, basil oil, bay leaf oil, benzoin oil, bergamot oil, buchu oil, camphor oil, *cannabis* oil, *cassia* oil, cedar oil, celery oil, chamomile oil, cinnamon oil, clary sage oil, clove oil, copaiba oil, cumin oil, *eucalyptus* oil, frankincense oil, galangal oil, geranium oil, ginger oil, grapefruit oil, guava oil, hops oil, hyssop oil, jasmine oil, juniper oil, lavender oil, lemon grass oil, lemon oil, lemongrass oil, lime oil, manuka oil, mandarin orange, marjoram oil, *melaleuca* oil, myrrh oil, nutmeg oil, orange oil, oregano oil, patchouli oil, peppermint oil, pine oil, rose oil, rosehip oil, rosemary oil, rosewood oil, sage oil, sandalwood oil, *sassafras* oil, spearmint oil, tangerine oil, tea tree oil, thyme oil, *tsuga* oil, valerian oil, vanilla oil, wintergreen oil, ylang-ylang oil, one or more fractions thereof, or a combination thereof.

Embodiment 18 provides the aziridnated triglyceride of Embodiment 17, wherein the aziridinated triglyceride is derived from the oil by a method comprising epoxidizing the oil treating the epoxidized product with a substituted or unsubstituted $(C_3-C_{50})$carboxylic acid including at least one aliphatic unsaturated carbon-carbon bond, and treating the $(C_3-C_{50})$carboxylic acid-treated product with an aziridine having the structure:

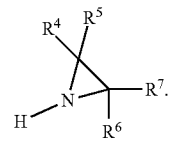

Embodiment 19 provides the aziridinated triglyceride of any one of Embodiments 1-18, wherein the aziridinated triglyceride is derived from soybean oil.

Embodiment 20 provides the aziridinated triglyceride of any one of Embodiments 1-19 having the structure:

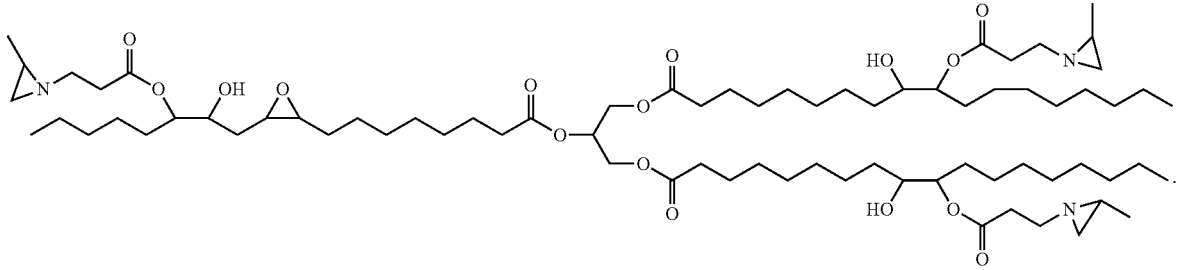 [SMILES: CCCCCCCCC(OC(=O)CCN1CC1C)C(O)CCCCCCCC(=O)OCC(COC(=O)CCCCCCCC(O)C(CCCCCCCC)OC(=O)CCN1CC1C)OC(=O)CCCCCCCC1OC1CC(O)C(CCCCC)OC(=O)CCN1CC1C]

Embodiment 21 provides a method of crosslinking the aziridinated triglyceride of any one of Embodiments 1-20, the method comprising:

contacting the aziridinated triglyceride with a crosslinker, to form a crosslinked triglyceride.

Embodiment 22 provides the method of Embodiment 21, wherein the crosslinker is a polycarboxylic acid.

Embodiment 23 provides the method of Embodiment 22, wherein the polycarboxylic acid is at least one of a HOC(O)—$R^a$—C(O)OH wherein $R^a$ is a substituted or unsubstituted $(C_1-C_{50})$hydrocarbylene interrupted or terminated by 0, 1, 2, or 3 groups independently chosen from —O—, —S—, substituted or unsubstituted —NH—, and —(O—$(C_2-C_3)$alkylene)$_n$- wherein n is about 1 to about 10,000 and wherein the $(C_2-C_3)$alkylene is substituted or unsubstituted, oxalic acid, maleic acid, succinic acid, methylsuccinic acid, malonic acid, adipic acid, glutaric acid, fumaric acid, dihydroxyfumaric acid, malic acid, mesaconic acid, itaconic acid, phthalic acid, isophthalic acid, terephthalic acid, 1,2-, 1,3-, or 1,4-cyclohexane dicarboxylic acid, 1,2,3-cyclohexane tricarboxylic acid, 1,2,4-cyclohexane tricarboxylic acid, 1,3,5-cyclohexane tricarboxylic acid, 1,2- or 1,3-cyclopentane dicarboxylic acid, citric acid, tartaric acid, dihydroxyterephthalic acid, 1,2,3-, 1,2,4-, or 1,2,5-benzene tricarboxylic acid, tricarballylic acid, 1,2,4,5-benzene tetracarboxylic acid, norbornene tetracarboxylic acid, 3,3', 4,4'-benzophenone tetracarboxylic acid, 1,2,3,4,5,6-benzene hexacarboxylic acid, aspartic acid, polyacrylic acid, and glutamic acid.

Embodiment 24 provides the method of Embodiment 22, wherein the polycarboxylic acid has the structure:

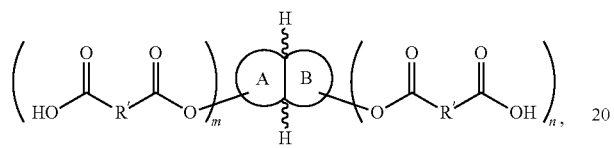

wherein
fused rings A and B are each independently chosen from substituted or unsubstituted ($C_5$-$C_{10}$)cycloalkyl and ($C_2$-$C_{10}$)heterocyclyl.
m and n are each independently 1-8, and
at each occurrence R' is independently chosen from substituted or unsubstituted ($C_2$-$C_{10}$)hydrocarbylene.

Embodiment 25 provides the method of Embodiment 24, wherein at each occurrence R' is independently unsubstituted.

Embodiment 26 provides the method of any one of Embodiments 24-25, wherein at each occurrence R' is independently chosen from ($C_1$-$C_5$)alkylene. ($C_5$-$C_{10}$)aryl, and ($C_2$-$C_5$)alkenylene.

Embodiment 27 provides the method of any one of Embodiments 24-26, wherein at each occurrence R' is independently chosen from —$CH_2$—$CH_2$—, —$CH_2$—$CH_2$—$CH_2$—, o-phenylene, and —CH═CH—.

Embodiment 28 provides the method of any one of Embodiments 24-27, wherein rings A and B are unsubstituted with the exception of the one or more ester substituents —OC(O)—R'—C(O)OH.

Embodiment 29 provides the method of any one of Embodiments 24-28, wherein m=n=1, and one of the ester substituents including R' is alpha to at least one carbon atom shared by rings A and B.

Embodiment 30 provides the method of any one of Embodiments 24-29, wherein rings A and B are the same size.

Embodiment 31 provides the method of any one of Embodiments 24-30, wherein rings A and B are 5-membered rings.

Embodiment 32 provides the method of any one of Embodiments 24-31, wherein at least one of rings A and B include at least one oxygen atom.

Embodiment 33 provides the method of any one of Embodiments 24-32, wherein each of rings A and B is a tetrahydrofuran ring, wherein each carbon atom shared by rings A and B has an oxygen atom alpha thereto.

Embodiment 34 provides the method of any one of Embodiments 24-33, wherein m=n.

Embodiment 35 provides the method of any one of Embodiments 24-34, wherein m=n=1.

Embodiment 36 provides the method of any one of Embodiments 24-35, wherein each of the ester substituents —OC(O)—R'—C(O)OH are alpha to a different carbon atom shared by each of rings A and B.

Embodiment 37 provides the method of any one of Embodiments 24-36, wherein rings A and B form a ring system chosen from isosorbide, isomannide, and isoidide.

Embodiment 38 provides the method of any one of Embodiments 24-37, wherein rings A and B are unsubstituted.

Embodiment 39 provides the method of any one of Embodiments 24-38, wherein the polycarboxylic acid has the structure:

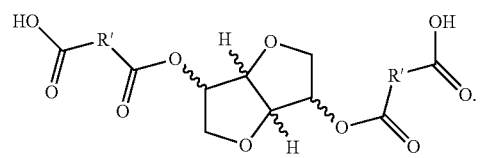

Embodiment 40 provides the method of any one of Embodiments 24-39, wherein the polycarboxylic acid is chosen from

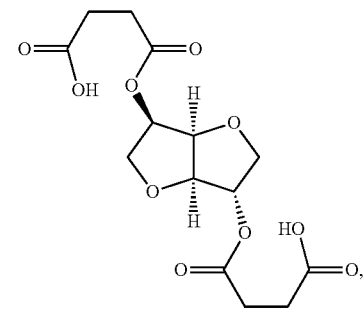

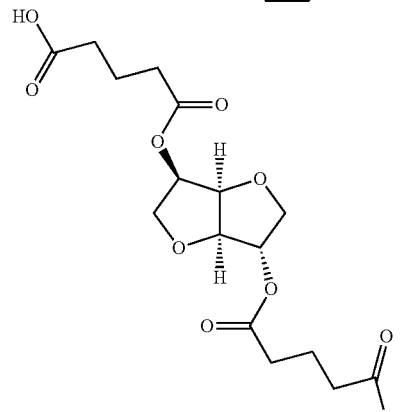

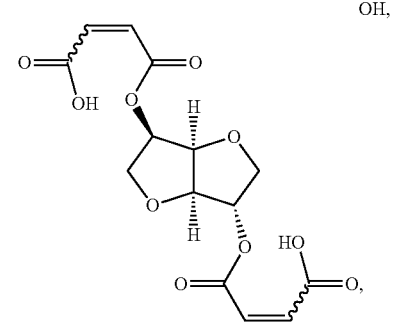

47
-continued
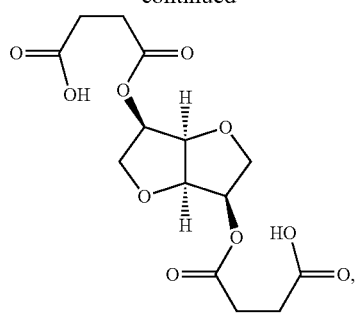
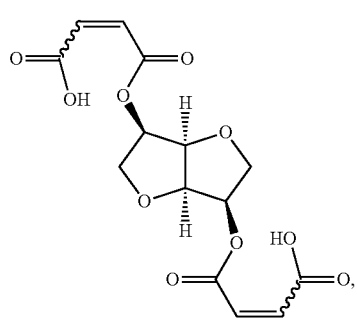
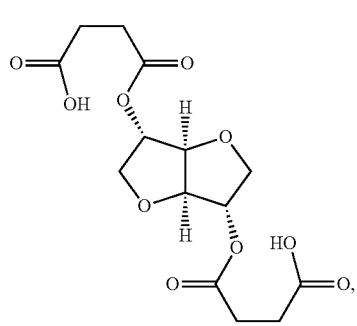
48
-continued
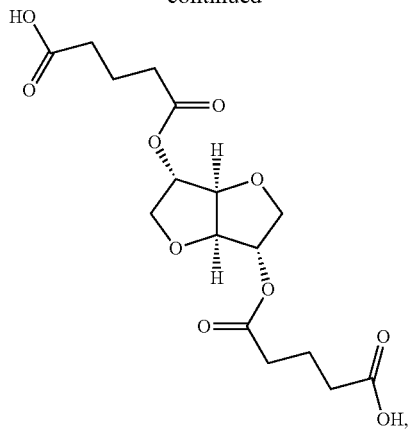

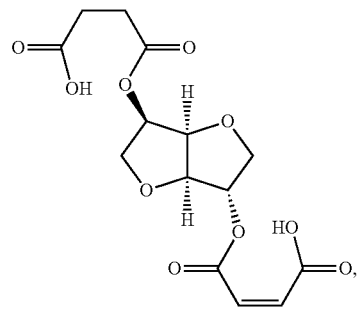
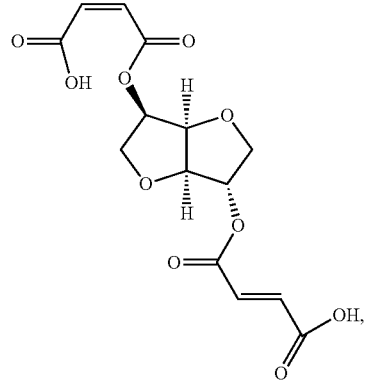
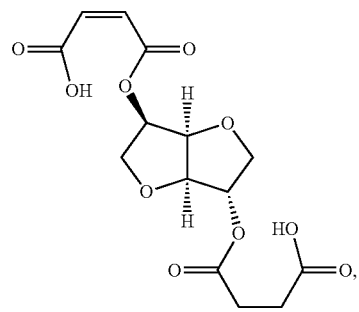
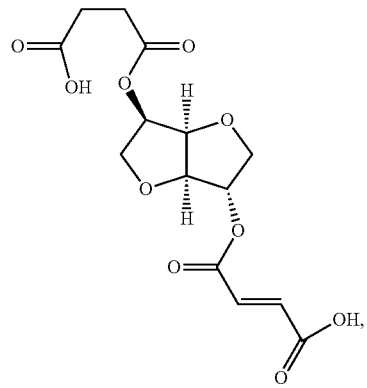
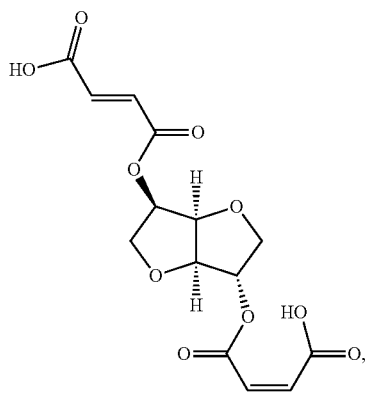
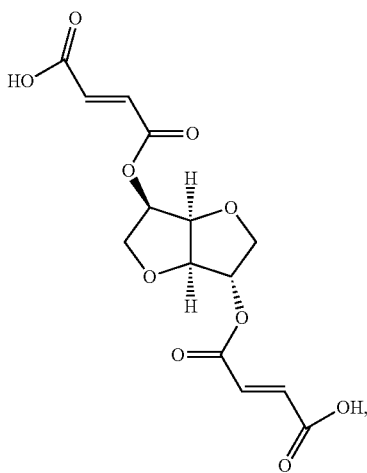
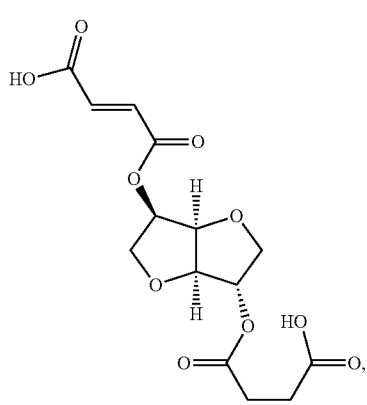
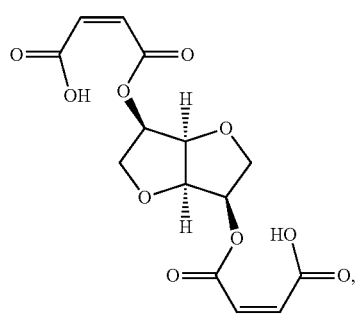

51
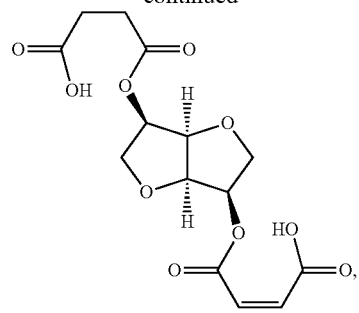
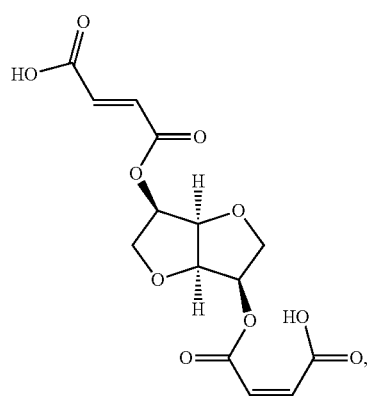
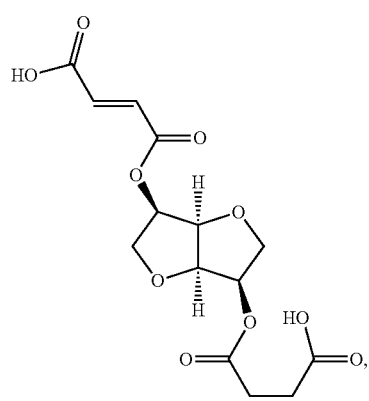
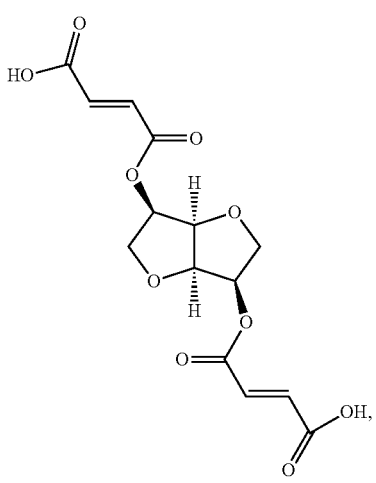
52
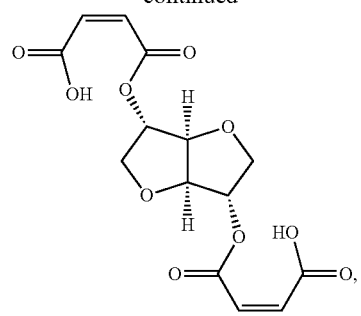
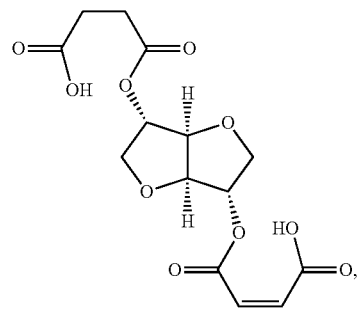
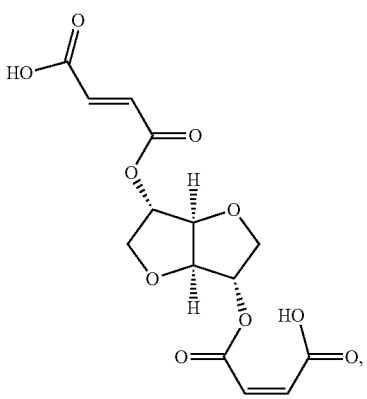
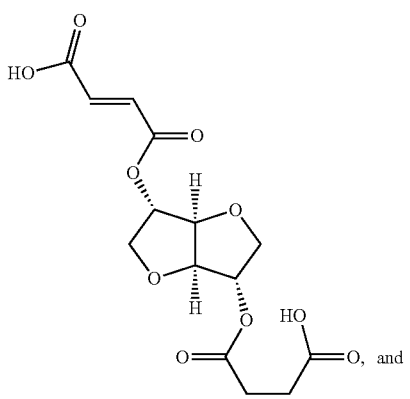

53

-continued

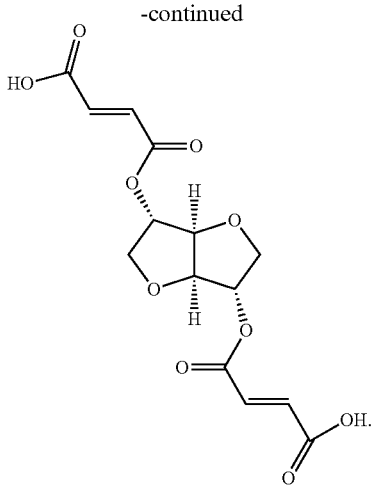

Embodiment 41 provides the method of any one of Embodiments 22-40, wherein the polycarboxylic acid is succinic acid, citric acid, an isosorbide-based diacid, or a combination thereof.

Embodiment 42 provides a polymer formed from reaction of the aziridinated triglyceride of any one of Embodiments 1-20 and a polycarboxylic acid.

Embodiment 43 provides a method of making the aziridinated triglyceride of any one of Embodiments 1-20, the method comprising:

combining an epoxidized triglyceride with a substituted or unsubstituted $(C_3-C_{50})$carboxylic acid including at least one aliphatic unsaturated carbon-carbon bond, and

54 treating the $(C_3-C_{50})$carboxylic acid-treated product with an aziridine having the structure:

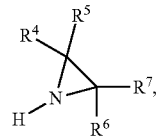

to give the aziridinated triglyceride of any one of Embodiments 1-20.

Embodiment 44 provides a polymer having the structure:

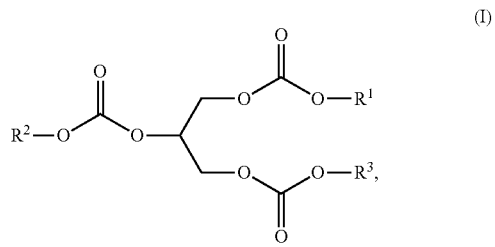

(I)

wherein $R^1$, $R^2$, and $R^3$ are each independently a substituted or unsubstituted $(C_1-C_{50})$hydrocarbyl optionally interrupted or terminated by the A end of at least one -AZP— group having the structure:

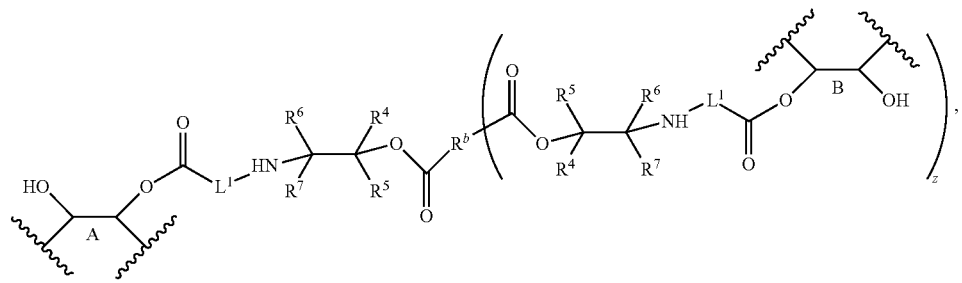

at each occurrence, $L^1$ is independently a substituted or unsubstituted $(C_2-C_{50})$hydrocarbyl interrupted or terminated with 0, 1, 2, or 3 groups independently chosen from —O—, —S—, and substituted or unsubstituted —NH—, at each occurrence, $R^4$, $R^5$, $R^6$, and $R^7$ are independently chosen from —H and substituted or unsubstituted $(C_1-C_{10})$hydrocarbyl interrupted or terminated with 0, 1, 2, or 3 groups independently chosen from —O—, —S—, and substituted or unsubstituted —NH—, $R^b$ is a substituted or unsubstituted $(C_1-C_5)$hydrocarbyl having a valence of z+1, wherein $R^b$ is interrupted or terminated by 0, 1, 2, or 3 groups independently chosen from —O—, —S—, substituted or unsubstituted —NH—, and —(O—$(C_2-C_3)$alkylene)$_n$- wherein n is about 1 to about 10,000 and wherein the $(C_2-C_3)$alkylene is substituted or unsubstituted.

z is about 1 to about 1,000.

the triglyceride I comprises at least one of the -AZP— groups, and each B end of the -AZP— group is independently interrupting or terminating R¹, R², or R³ of the same or different triglyceride I, wherein at least one B end of at least one -AZP— group in the triglyceride I interrupts or terminates R¹, R², or R³ of a different triglyceride I.

Embodiment 45 provides the polymer of Embodiment 44, wherein the polymer has about 2 to about 100,000,000 triglycerides of structure I.

Embodiment 46 provides the polymer of any one of Embodiments 44-45, wherein at least one of R¹, R², and R³ is interrupted or terminated with at least one of the -AZP— groups.

Embodiment 47 provides the polymer of any one of Embodiments 44-46, wherein the aziridinated triglyceride comprises at least two of the -AZP— groups.

Embodiment 48 provides the polymer of any one of Embodiments 44-47, wherein R¹, R², and R³ are each independently a substituted or unsubstituted $(C_{10}-C_{50})$hydrocarbyl optionally interrupted or terminated by at least one -AZP— group.

Embodiment 49 provides the polymer of any one of Embodiments 44-48, wherein R¹, R², and R³ are each independently a substituted or unsubstituted $(C_1-C_{50})$alkane optionally interrupted or terminated with at least one of the -AZP— groups.

Embodiment 50 provides the polymer of any one of Embodiments 44-49, wherein R¹, R², and R³ are each independently a $(C_1-C_{50})$alkane optionally interrupted or terminated with at least one of the -AZP— groups, substituted with 0, 1, 2, 3, 4, or 5 epoxy groups, and otherwise unsubstituted.

Embodiment 51 provides the polymer of any one of Embodiments 44-50, wherein R¹, R², and R³ are each independently an unsubstituted $(C_1-C_{50})$alkane optionally interrupted or terminated with at least one of the -AZP— groups.

Embodiment 52 provides the polymer of any one of Embodiments 44-51, wherein at each occurrence, L¹ is independently an unsubstituted $(C_2-C_{50})$alkanylene.

Embodiment 53 provides the polymer of any one of Embodiments 44-52, wherein at each occurrence, L¹ is independently an unsubstituted $(C_2-C_{10})$alkanylene.

Embodiment 54 provides the polymer of any one of Embodiments 44-53, wherein at each occurrence. L¹ is independently an unsubstituted $(C_2-C_{10})$alkanylene.

Embodiment 55 provides the polymer of any one of Embodiments 44-54, wherein at each occurrence, R⁴, R, R⁶, and R⁷ are independently chosen from —H and unsubstituted $(C_1-C_{10})$hydrocarbyl.

Embodiment 56 provides the polymer of any one of Embodiments 44-55, wherein at each occurrence, R⁵, R⁶, and R⁷ are —H.

Embodiment 57 provides the polymer of any one of Embodiments 44-56, wherein at each occurrence, R⁵, R⁶, and R⁷ are —H, and R⁴ is unsubstituted $(C_1-C_{10})$hydrocarbyl.

Embodiment 58 provides the polymer of any one of Embodiments 44-57, wherein at each occurrence, R⁵, R⁶, and R⁷ are —H, and R⁴ is unsubstituted $(C_1-C_5)$alkyl.

Embodiment 59 provides the polymer of any one of Embodiments 44-58, wherein at each occurrence, R⁵, R⁶, and R⁷ are —H, and R⁴ is methyl.

Embodiment 60 provides the polymer of any one of Embodiments 44-59, wherein -AZP— has the structure:

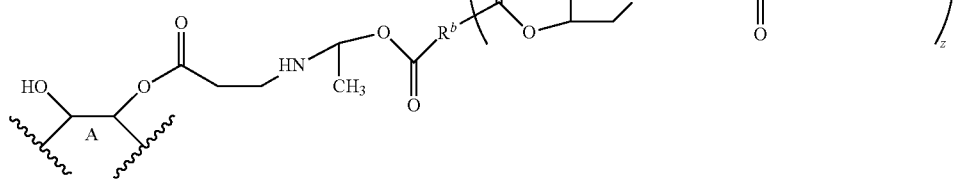

Embodiment 61 provides the polymer of any one of Embodiments 44-60, wherein the triglyceride I is derived from açaí oil, almond oil, amaranth oil, apple seed oil, apricot oil, argan oil, avocado oil, babassu oil beech nut oil, ben oil, bitter gourd oil, black seed oil, blackcurrant seed oil, borage seed oil, borneo tallow nut oil bottle gourd oil, buffalo gourd oil, butternut squash seed oil, *camelina sativa* oil, cape chestnut oil, carob pod oil, cashew oil, cocklebur oil, cocoa butter, coconut oil, cohune oil, coriander seed oil, corn oil, cottonseed oil, date seed oil, dika oil, egusi seed oil, evening primrose oil, flaxseed oil, grape seed oil, grapefruit seed oil, hazelnut oil, hemp oil, kapok seed oil, kenaf seed oil, *lallemantia* oil, linseed oil, macadamia oil, mafura oil, marula oil, meadowfoam seed oil, mongongo nut oil, mustard oil, niger seed oil, okra seed oil, olive oil, orange oil, palm oil, *papaya* seed oil, peanut oil, pecan oil, pequi oil, *perilla* seed oil, persimmon seed oil, pili nut oil, pistachio oil, pomegranate oil, poppyseed oil, prune kernel oil, pumpkin seed oil, *quinoa* oil, ramtil oil rapeseed oil, rice bran oil, royle oil, safflower oil, sapote oil, seje oil, sesame oil, shea butter, soybean oil, sunflower oil, taramira oil, tea seed oil, thistle oil, tigernut oil, tobacco seed oil, tomato seed oil, walnut oil, watermelon seed oil, wheat germ oil, agarwood oil, allspice oil, almond oil, anise oil, basil oil, bay leaf oil, benzoin oil, bergamot oil, buchu oil, camphor oil, *cannabis* oil, *cassia* oil, cedar oil, celery oil, chamomile oil, cinnamon oil, clary sage oil, clove oil, copaiba oil, cumin oil. *eucalyptus* oil, frankincense oil, galangal oil, geranium oil, ginger oil, grapefruit oil, guava oil, hops oil, hyssop oil, jasmine oil, juniper oil, lavender oil, lemon grass oil, lemon oil, lemongrass oil, lime oil, manuka oil, mandarin orange, marjoram oil, *melaleuca* oil, myrrh oil, nutmeg oil, orange oil, oregano oil, patchouli oil, peppermint oil, pine oil, rose oil, rosehip oil, rosemary oil, rosewood oil, sage oil, sandalwood oil, *sassafras* oil, spearmint oil, tangerine oil, tea tree oil, thyme oil, *tsuga* oil, valerian oil, vanilla oil, wintergreen oil, ylang-ylang oil, one or more fractions thereof, or a combination thereof.

Embodiment 62 provides the polymer of any one of Embodiments 44-61, wherein the triglyceride I is derived from soybean oil.

Embodiment 63 provides the polymer of any one of Embodiments 44-62, wherein triglyceride I has the structure:

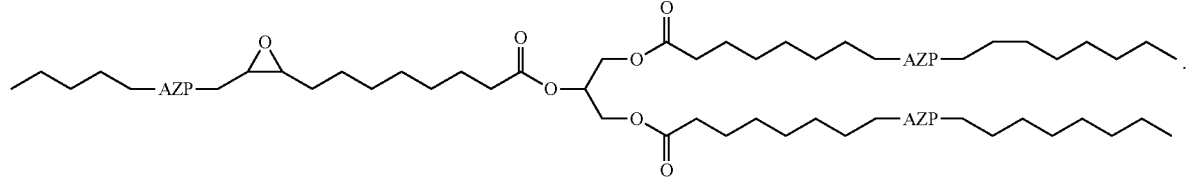

Embodiment 64 provides the polymer of any one of Embodiments 44-63, wherein the —O—C(O)—$R^b$(—C(O)—O)$_z$— portion of triglyceride I corresponds to a polycarboxylic acid that has reacted with z+1 aziridine groups.

Embodiment 65 provides the polymer of any one of Embodiments 44-64, wherein the polycarboxylic acid is at least one of a HOC(O)—$R^a$—C(O)OH wherein $R^a$ is a substituted or unsubstituted ($C_1$-$C_{50}$)hydrocarbylene interrupted or terminated by 0, 1, 2, or 3 groups independently chosen from —O—, —S—, substituted or unsubstituted —NH—, and —(O—($C_2$-$C_3$)alkylene)$_n$- wherein n is about 1 to about 10,000 and wherein the ($C_2$-$C_3$)alkylene is substituted or unsubstituted, oxalic acid, maleic acid, succinic acid, methylsuccinic acid, malonic acid, adipic acid, glutaric acid, fumaric acid, dihydroxyfumaric acid, malic acid, mesaconic acid, itaconic acid, phthalic acid, isophthalic acid, terephthalic acid, 1.2-, 1.3-, or 1,4-cyclohexane dicarboxylic acid, 1,2,3-cyclohexane tricarboxylic acid, 1,2,4-cyclohexane tricarboxylic acid, 1,3,5-cyclohexane tricarboxylic acid, 1.2- or 1,3-cyclopentane dicarboxylic acid, citric acid, tartaric acid, dihydroxyterephthalic acid, 1,2,3-, 1,2,4-, or 1,2,5-benzene tricarboxylic acid, tricarballylic acid, 1,2,4,5-benzene tetracarboxylic acid, norbornene tetracarboxylic acid, 3,3',4,4'-benzophenone tetracarboxylic acid, 1,2,3,4,5,6-benzene hexacarboxylic acid, aspartic acid, polyacrylic acid, and glutamic acid.

Embodiment 66 provides the polymer of any one of Embodiments 44-65, wherein the polycarboxylic acid has the structure:

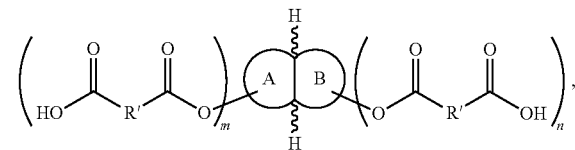

wherein
fused rings A and B are each independently chosen from substituted or unsubstituted ($C_5$-$C_{10}$)cycloalkyl and ($C_2$-$C_{10}$)heterocyclyl.
m and n are each independently 1-8, and
at each occurrence R' is independently chosen from substituted or unsubstituted ($C_2$-$C_{10}$)hydrocarbylene.

Embodiment 67 provides the polymer of Embodiment 66, wherein at each occurrence R' is independently unsubstituted.

Embodiment 68 provides the polymer of any one of Embodiments 66-67, wherein at each occurrence R' is independently chosen from ($C_1$-$C_5$)alkylene. ($C_5$-$C_{10}$)aryl, and ($C_2$-$C_5$)alkenylene.

Embodiment 69 provides the polymer of any one of Embodiments 66-68, wherein at each occurrence R' is independently chosen from —$CH_2$—$CH_2$—, —$CH_2$—$CH_2$—$CH_2$—, o-phenylene, and —CH—CH—.

Embodiment 70 provides the polymer of any one of Embodiments 66-69, wherein rings A and B are unsubstituted with the exception of the one or more ester substituents —OC(O)—R'—C(O)OH.

Embodiment 71 provides the polymer of any one of Embodiments 66-70, wherein m=n=1, and one of the ester substituents including R' is alpha to at least one carbon atom shared by rings A and B.

Embodiment 72 provides the polymer of any one of Embodiments 66-71, wherein rings A and B are the same size.

Embodiment 73 provides the polymer of any one of Embodiments 66-72, wherein rings A and B are 5-membered rings.

Embodiment 74 provides the polymer of any one of Embodiments 66-73, wherein at least one of rings A and B include at least one oxygen atom.

Embodiment 75 provides the polymer of any one of Embodiments 66-74, wherein each of rings A and B is a tetrahydrofuran ring, wherein each carbon atom shared by rings A and B has an oxygen atom alpha thereto.

Embodiment 76 provides the polymer of any one of Embodiments 66-75, wherein m=n.

Embodiment 77 provides the polymer of any one of Embodiments 66-76, wherein m=n=1.

Embodiment 78 provides the polymer of any one of Embodiments 66-77, wherein each of the ester substituents —OC(O)—R'—C(O)OH are alpha to a different carbon atom shared by each of rings A and B.

Embodiment 79 provides the polymer of any one of Embodiments 66-78, wherein rings A and B form a ring system chosen from isosorbide, isomannide, and isoidide.

Embodiment 80 provides the polymer of any one of Embodiments 66-79, wherein rings A and B are unsubstituted.

Embodiment 81 provides the polymer of any one of Embodiments 66-80, wherein the polycarboxylic acid has the structure:

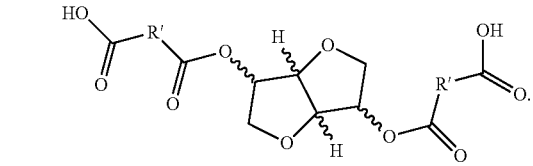

Embodiment 82 provides the polymer of any one of Embodiments 66-81, wherein the polycarboxylic acid is chosen from 59
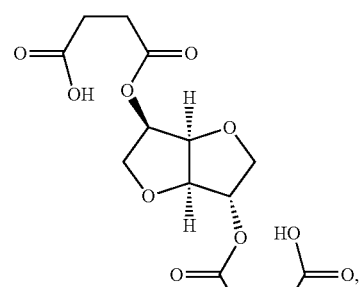
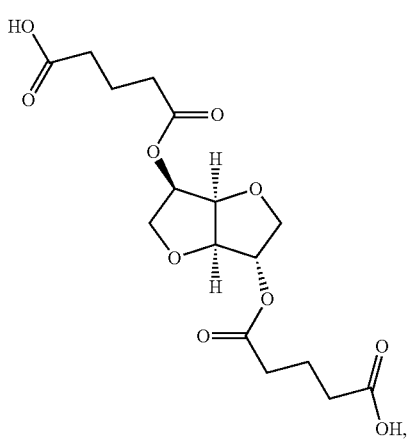
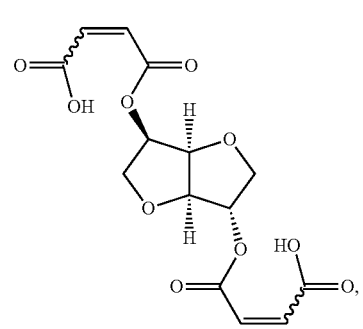
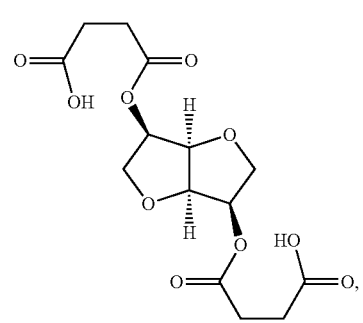
60
-continued
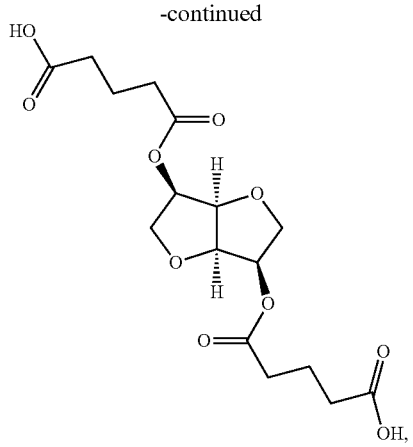
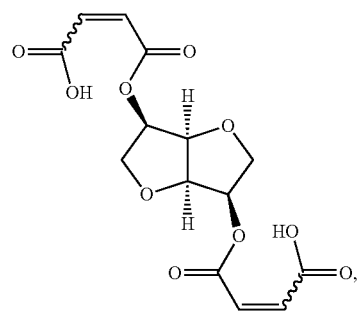
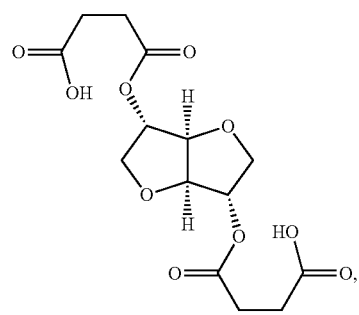
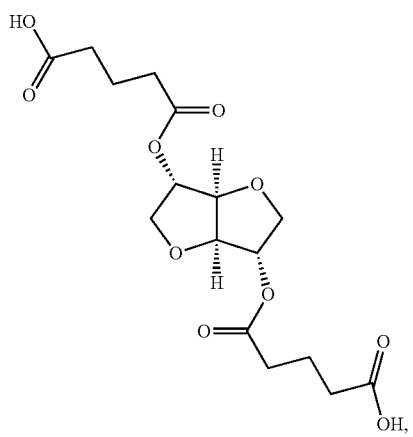

61
-continued
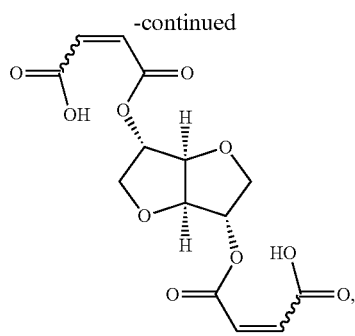
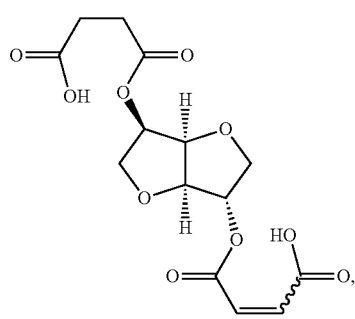
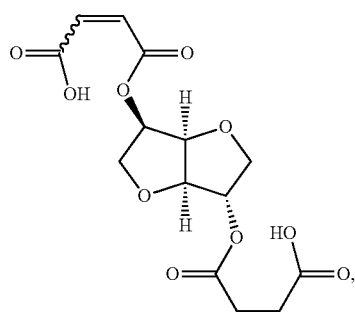
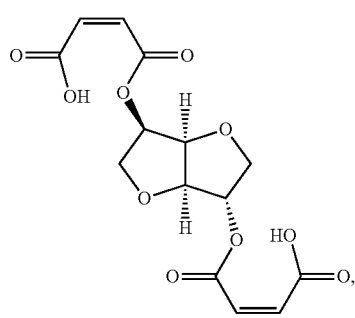
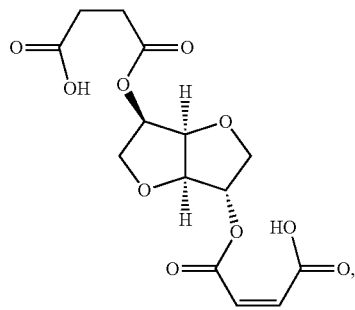
62
-continued
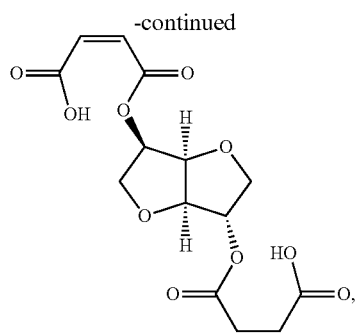
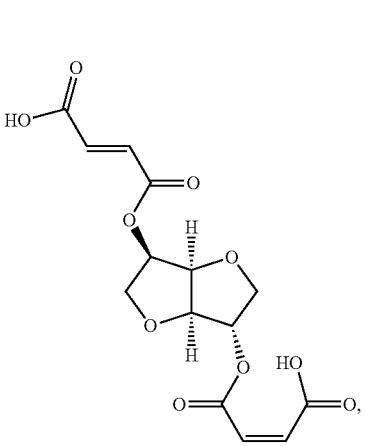
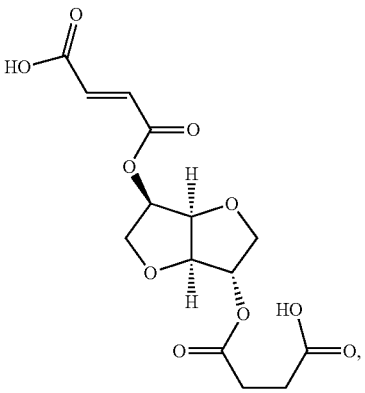
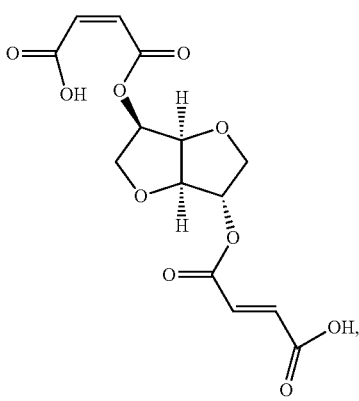

63
-continued
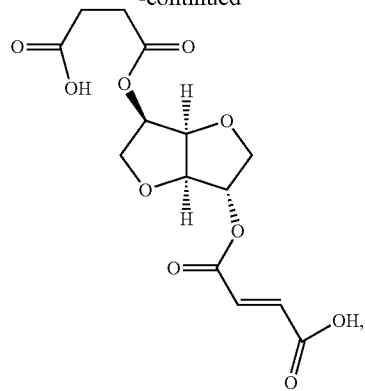
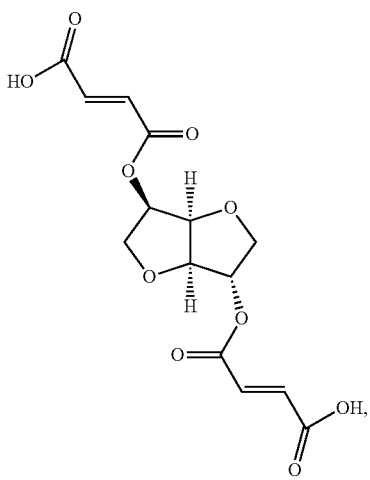
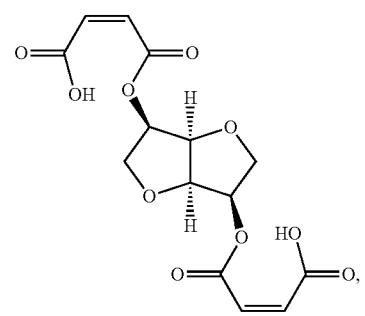
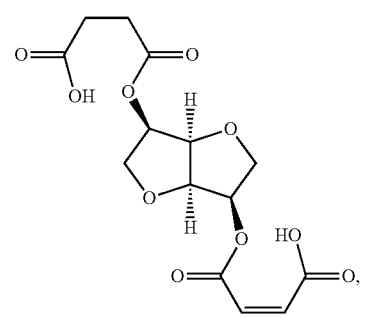
64
-continued
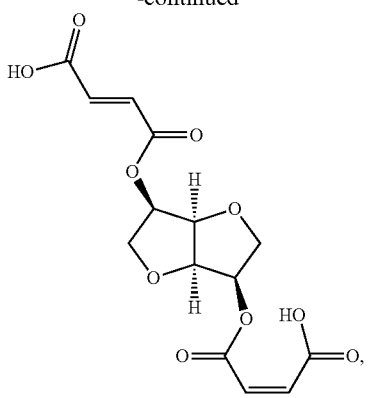
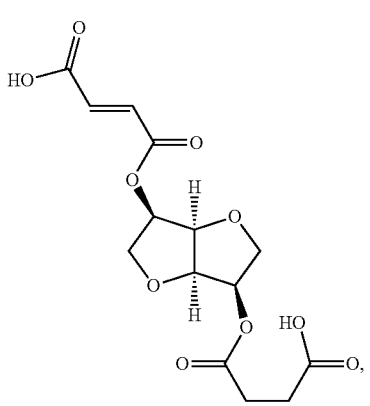
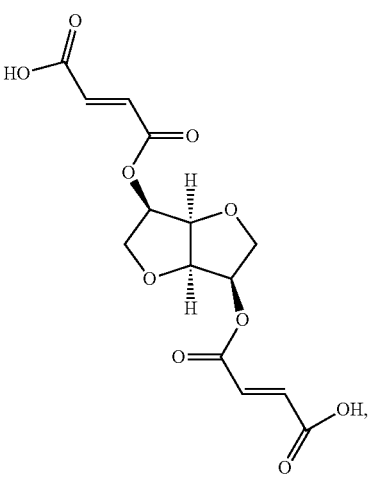
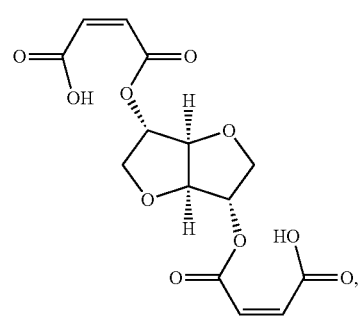

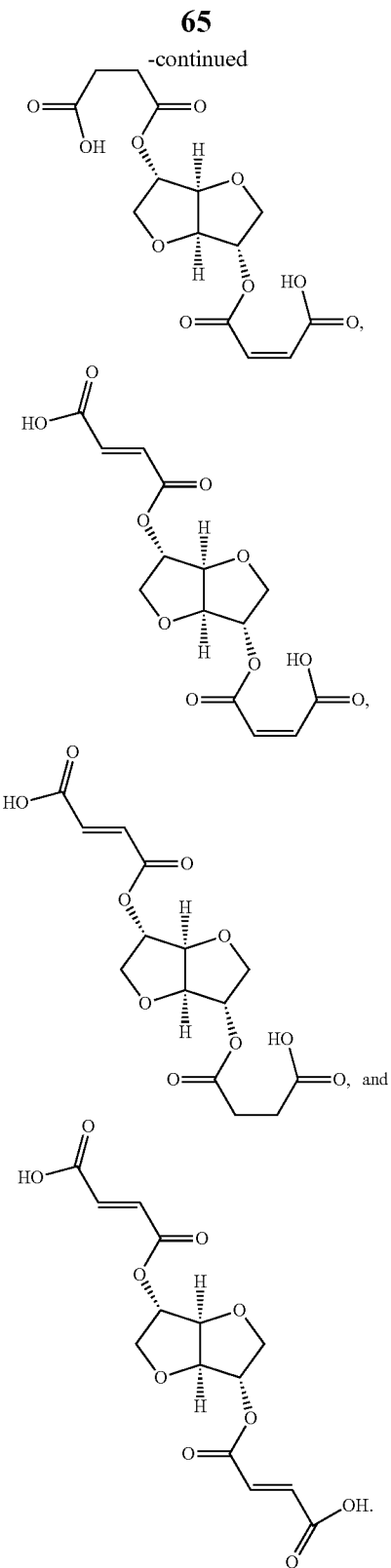

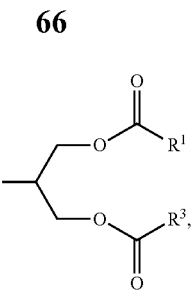

wherein
R¹, R², and R³ are each independently a substituted or unsubstituted $(C_1-C_{50})$hydrocarbyl optionally interrupted or terminated by at least one -A- group having the structure:

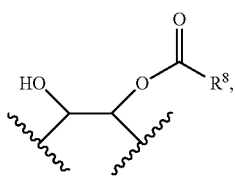

at each occurrence, R⁸ is independently a substituted or unsubstituted $(C_2-C_{50})$hydrocarbyl comprising at least one aliphatic carbon-carbon unsaturated bond and is interrupted or terminated with 0, 1, 2, or 3 groups independently chosen from —O—, —S—, and substituted or unsubstituted —NH—, and
the triglyceride comprises at least one of the -A- groups.

Embodiment 85 provides the triglyceride of Embodiment 84, wherein R⁸ is independently an unsubstituted $(C_2-C_{20})$ hydrocarbyl comprising at least one aliphatic carbon-carbon unsaturated bond.

Embodiment 86 provides the triglyceride of any one of Embodiments 84-85, wherein R⁸ is —CH=CH₂.

Embodiment 87 provides a method of making the triglyceride of any one of Embodiments 84-86, the method comprising:
combining an epoxidized triglyceride with a substituted or unsubstituted $(C_3-C_{50})$carboxylic acid including at least one aliphatic unsaturated carbon-carbon bond to give the triglyceride of any one of Embodiments 84-86.

Embodiment 88 provides the aziridinated triglyceride or method of any one or any combination of Embodiments 1-87 optionally configured such that all elements or options recited are available to use or select from.

What is claimed is:
1. A polymer comprising a plurality of units of Formula (I):

Formula (I)

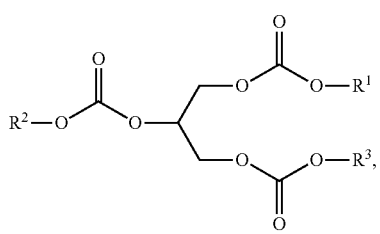

wherein
R¹, R², and R³ are each independently a substituted or unsubstituted $(C_1-C_{50})$hydrocarbyl and at least one of Embodiment 83 provides the polymer of any one of Embodiments 44-82, wherein the polycarboxylic acid is succinic acid, citric acid, an isosorbide-based diacid, or a combination thereof.

Embodiment 84 provides a triglyceride having the structure:

R¹, R², and R³ is interrupted or terminated by the A end of at least one -AZP— group having the structure:

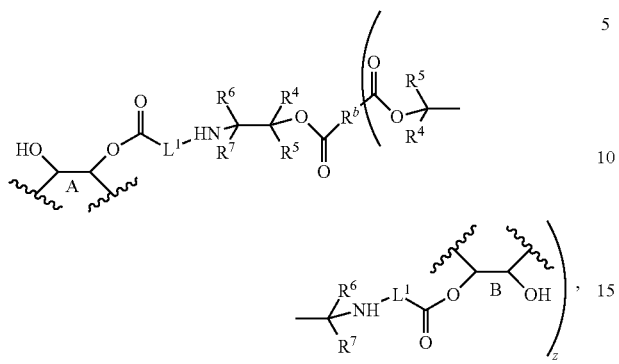

at each occurrence, L¹ is independently a substituted or unsubstituted (C₂-C₅₀)hydrocarbyl interrupted or terminated with 0, 1, 2, or 3 groups independently chosen from —O—, —S—, and substituted or unsubstituted —NH—, at each occurrence, R⁴, R⁵, R⁶, and R⁷ are independently chosen from —H and substituted or unsubstituted (C₁-C₁₀)hydrocarbyl interrupted or terminated with 0, 1, 2, or 3 groups independently chosen from —O—, —S—, and substituted or unsubstituted —NH—, at each occurrence, R$^b$ is independently a substituted or unsubstituted (C₁-C₅₀)hydrocarbyl having a valence of z+1, wherein R$^b$ is interrupted or terminated by 0, 1, 2, or 3 groups independently chosen from —O—, —S—, substituted or unsubstituted —NH—, and —(O—(C₂-C₃)alkylene)$_n$—, wherein n is about 1 to about 10,000 and wherein the (C₂-C₃)alkylene is substituted or unsubstituted, z is about 1 to about 1,000, and each B end of the -AZP— group independently interrupts or terminates R¹, R², or R³ of the same unit of Formula (I) or of one or more separate units of Formula (I), and at least one -AZP— group links two or more separate units of Formula (I).

2. The polymer of claim 1, wherein the polymer has about 2 to about 100,000,000 units of Formula (I).

3. The polymer of claim 1, wherein -AZP— has the structure:

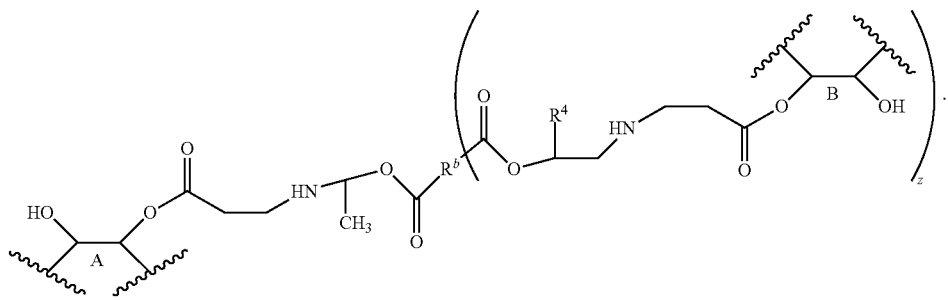

4. The polymer of claim 1, wherein triglyceride I has the structure:

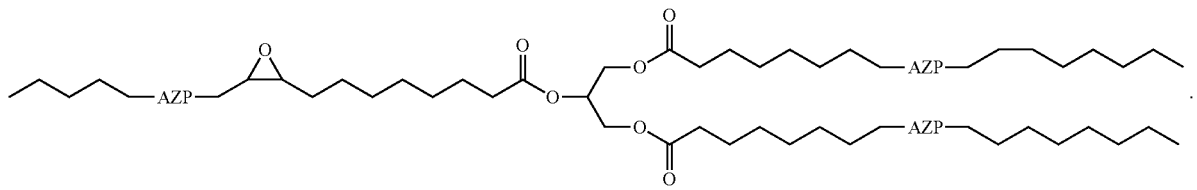

5. The polymer of claim 1, wherein the unit of Formula (I) comprises two or more -AZP— groups.

6. The polymer of claim 1, wherein each of R¹, R², and R³ have no more than one -AZP— group.

7. The polymer of claim 1, wherein at least one of R¹, R², and R³ is interrupted or terminated by at least two -AZP— groups.

8. The polymer of claim 1, wherein R¹, R², and R³ are each independently a substituted or unsubstituted (C₁₀-C₅₀) hydrocarbyl and each of R¹, R², and R³ is interrupted or terminated by at least one -AZP—group.

9. The polymer of claim 1, wherein R¹, R², and R³ are each independently unsubstituted (C₁-C₅₀)alkane; unsubstituted (C₁-C₅₀)alkane interrupted or terminated with at least one -AZP— group, or unsubstituted (C₁-C₅₀)alkane substituted with 0, 1, 2, 3, 4, or 5 epoxy groups.

10. The polymer of claim 1, wherein $R^1$, $R^2$, and $R^3$ are each independently an unsubstituted $(C_1\text{-}C_{50})$alkane or unsubstituted $(C_1\text{-}C_{50})$alkane interrupted or terminated with at least one -AZP— group.

11. The polymer of claim 1, wherein at each occurrence, $L^1$ is independently an unsubstituted $(C_2\text{-}C_{10})$alkanylene.

12. The polymer of claim 1, wherein at each occurrence, $R^4$, $R^5$, $R^6$, and $R^7$ are —H or unsubstituted $(C_1\text{-}C_{10})$hydrocarbyl.

13. The polymer of claim 1, wherein at each occurrence, $R^5$, $R^6$, and $R^7$ are —H.

14. The polymer of claim 1, wherein at each occurrence, $R^5$, $R^6$, and $R^7$ are —H, and $R^4$ is unsubstituted $(C_1\text{-}C_{10})$hydrocarbyl.

15. The polymer of claim 1, wherein at each occurrence, $R^5$, $R^6$, and $R^7$ are —H, and $R^4$ is unsubstituted $(C_1\text{-}C_5)$alkyl.

16. The polymer of claim 1, wherein $R_b$ taken together with the carboxylates to which it is attached corresponds to an oxalic acid, maleic acid, succinic acid, methylsuccinic acid, malonic acid, adipic acid, glutaric acid, fumaric acid, dihydroxyfumaric acid, malic acid, mesaconic acid, itaconic acid, phthalic acid, isophthalic acid, terephthalic acid, 1,2, 1,3-, or 1,4-cyclohexane dicarboxylic acid, 1,2,3-cyclohexane tricarboxylic acid, 1,2,4-cyclohexane tricarboxylic acid, 1,3,5-cyclohexane tricarboxylic acid, 1,2-or 1,3-cyclopentane dicarboxylic acid, citric acid, tartaric acid, dihydroxyterephthalic acid, 1,2,3, 1,2,4, or 1,2,5-benzene tricarboxylic acid, tricarballylic acid, 1,2,4,5-benzene tetracarboxylic acid, norbornene tetracarboxylic acid, 3,3', 4,4'-benzophenone tetracarboxylic acid, 1,2,3,4,5,6-benzene hexacarboxylic acid, aspartic acid, polyacrylic acid, glutamic acid, or an isosorbide-based diacid linker.

17. The polymer of claim 1, wherein $R_b$ taken together with the carboxylates to which it is attached, corresponds to a linker derived from

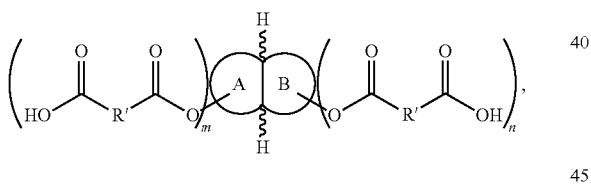

wherein
fused rings A and B are each independently chosen from substituted or unsubstituted $(C_5\text{-}C_{10})$cycloalkyl and $(C_2\text{-}C_{10})$heterocyclyl,
m and n are each independently 1-8, and
at each occurrence R' is independently chosen from substituted or unsubstituted $(C_2\text{-}C_{10})$hydrocarbylene.

18. The polymer of claim 1, wherein $R_b$ taken together with the carboxylates to which it is attached, corresponds to a linker derived from:

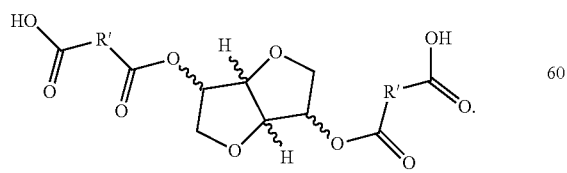

19. The polymer of claim 1, wherein $R_b$ taken together with the carboxylates to which it is attached, corresponds to a linker derived from:

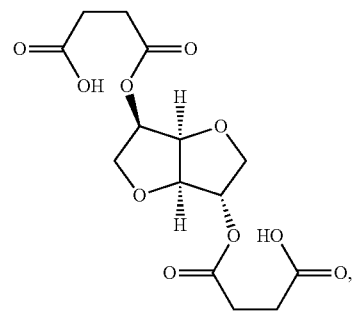

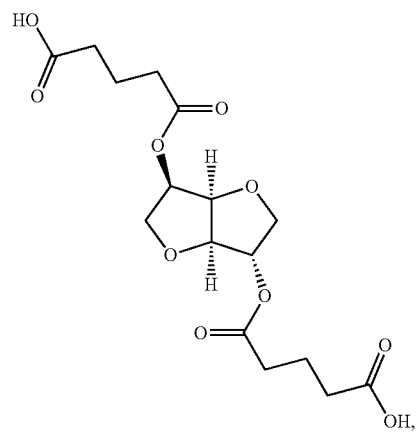

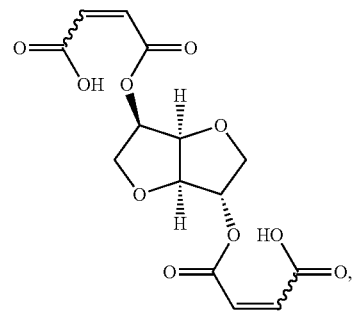

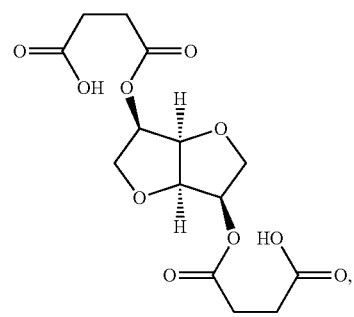

71
-continued
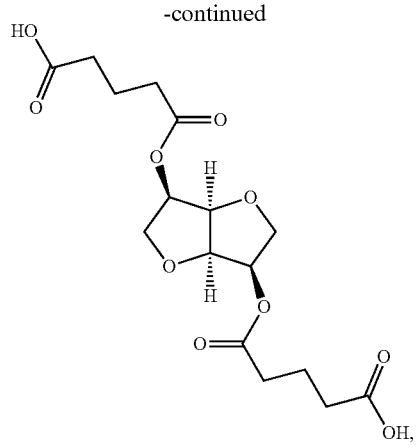
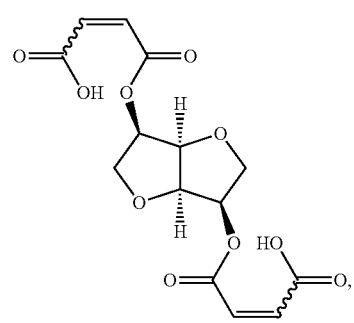
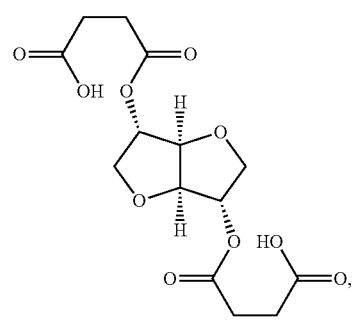
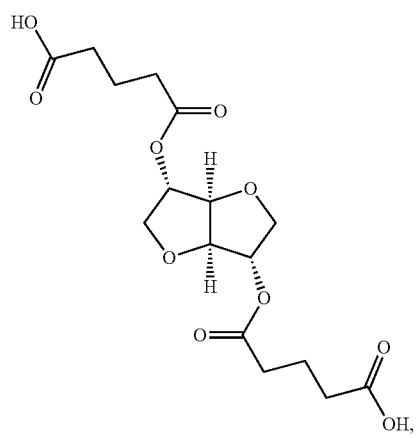
72
-continued
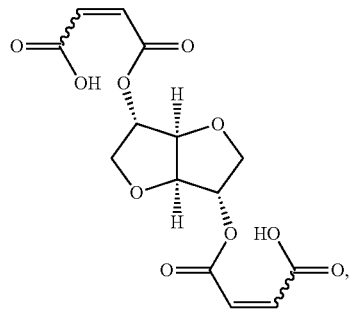
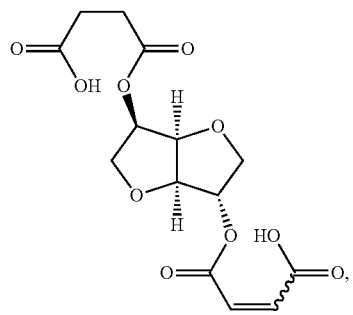
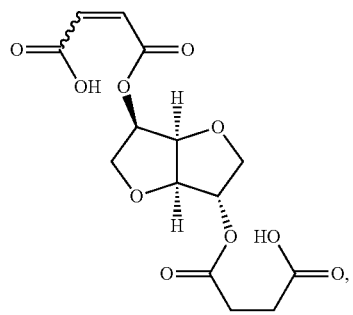
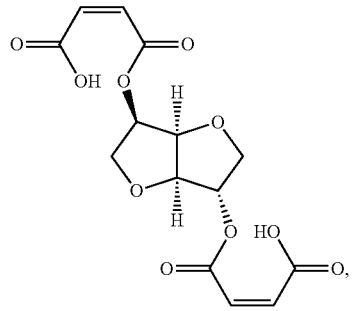
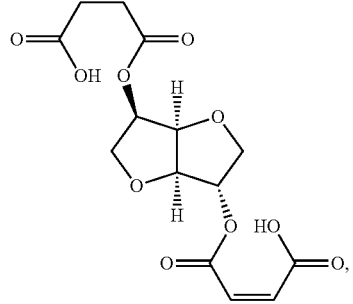

73
-continued
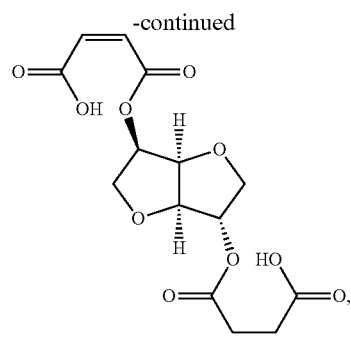
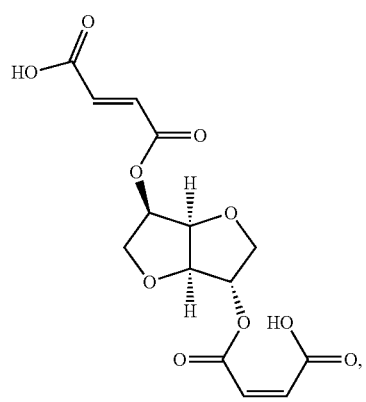
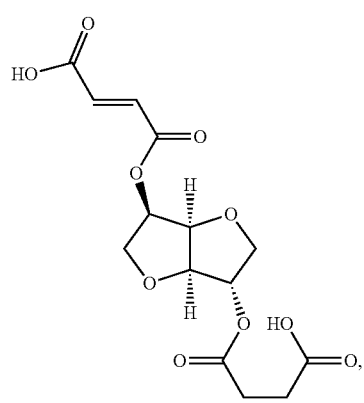
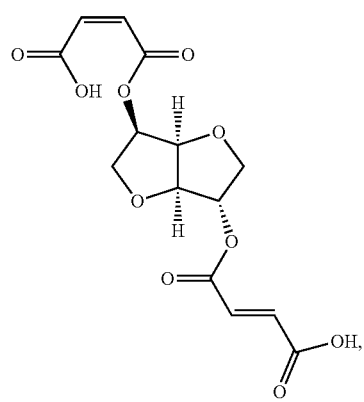
74
-continued
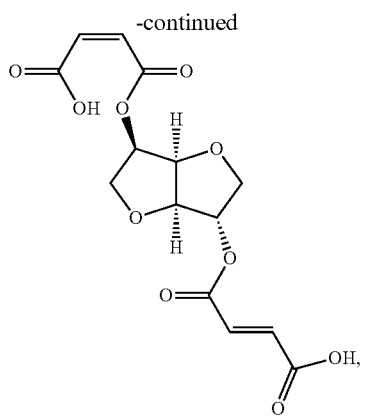
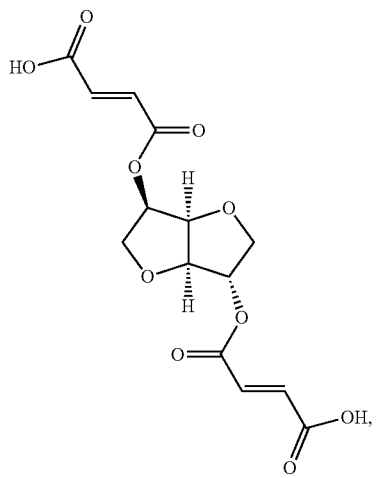
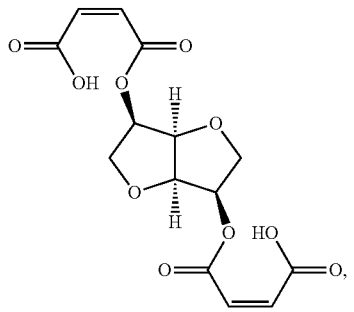
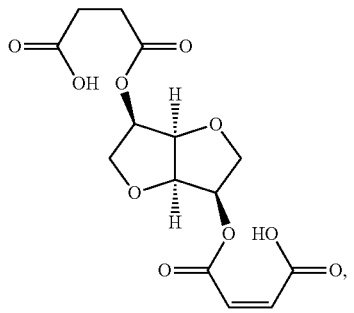

75
-continued
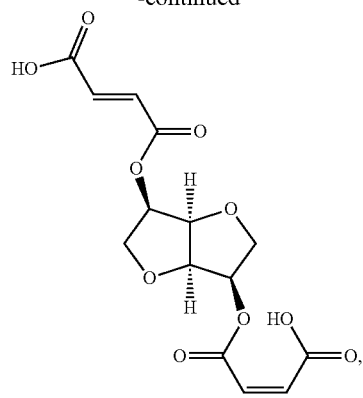
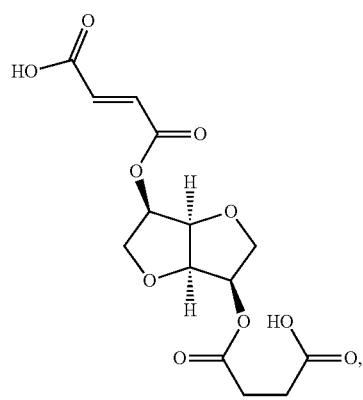
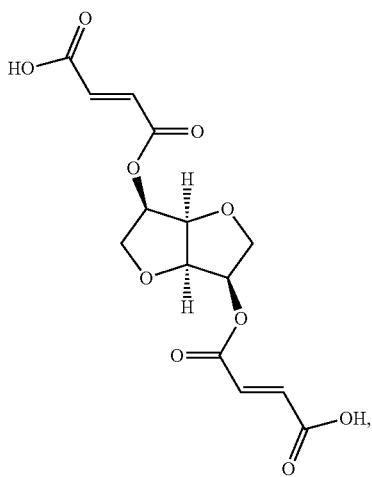
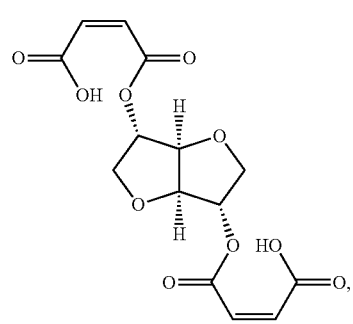
76
-continued
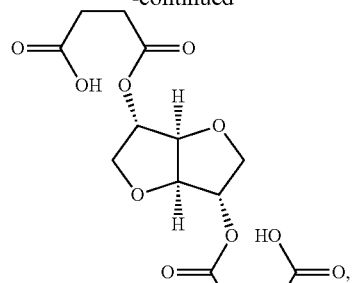
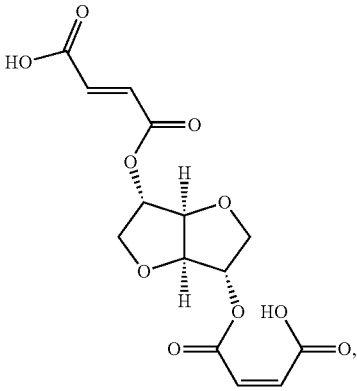
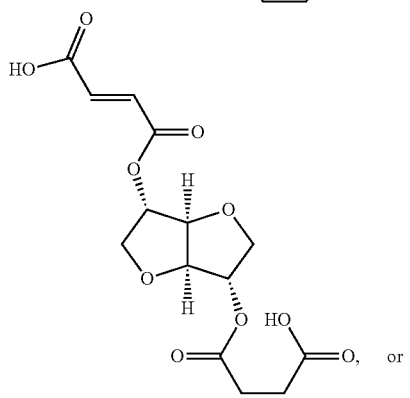
, or
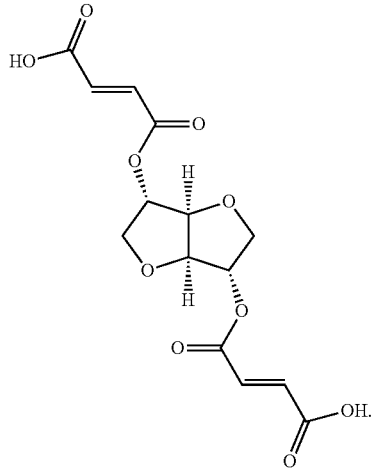
20. The polymer of claim 1, wherein the unit of Formula (I) is derived from açaí oil, almond oil, amaranth oil, apple seed oil, apricot oil, argan oil, avocado oil, babassu oil, beech nut oil, ben oil, bitter gourd oil, black seed oil, blackcurrant seed oil, borage seed oil, borneo tallow nut oil, bottle gourd oil, buffalo gourd oil, butternut squash seed oil, camelina sativa oil, cape chestnut oil, carob pod oil, cashew oil, cocklebur oil, cocoa butter, coconut oil, cohune oil, coriander seed oil, corn oil, cottonseed oil, date seed oil, dika oil, egusi seed oil, evening primrose oil, flaxseed oil, grape seed oil, grapefruit seed oil, hazelnut oil, hemp oil, kapok seed oil, kenaf seed oil, lallemantia oil, linseed oil, macadamia oil, mafura oil, marula oil, meadowfoam seed oil, mongongo nut oil, mustard oil, niger seed oil, okra seed oil, olive oil, orange oil, palm oil, papaya seed oil, peanut oil, pecan oil, pequi oil, perilla seed oil, persimmon seed oil, pili nut oil, pistachio oil, pomegranate seed oil, poppyseed oil, prune kernel oil, pumpkin seed oil, quinoa oil, ramtil oil, rapeseed oil, rice bran oil, royle oil, safflower oil, sapote oil, seje oil, sesame oil, shea butter, soybean oil, sunflower oil, taramira oil, tea seed oil, thistle oil, tigernut oil, tobacco seed oil, tomato seed oil, walnut oil, watermelon seed oil, wheat germ oil, agarwood oil, allspice oil, almond oil, anise oil, basil oil, bay leaf oil, benzoin oil, bergamot oil, buchu oil, camphor oil, cannabis oil, cassia oil, cedar oil, celery oil, chamomile oil, cinnamon oil, clary sage oil, clove oil, copaiba oil, cumin oil, eucalyptus oil, frankincense oil, galangal oil, geranium oil, ginger oil, grapefruit oil, guava oil, hops oil, hyssop oil, jasmine oil, juniper oil, lavender oil, lemon grass oil, lemon oil, lemongrass oil, lime oil, manuka oil, mandarin orange, marjoram oil, melaleuca oil, myrrh oil, nutmeg oil, orange oil, oregano oil, patchouli oil, peppermint oil, pine oil, rose oil, rosehip oil, rosemary oil, rosewood oil, sage oil, sandalwood oil, sassafras oil, spearmint oil, tangerine oil, tea tree oil, thyme oil, tsuga oil, valerian oil, vanilla oil, wintergreen oil, ylang-ylang oil, one or more fractions thereof, or a combination thereof.

\* \* \* \* \*

UNITED STATES PATENT AND TRADEMARK OFFICE
CERTIFICATE OF CORRECTION

PATENT NO. : 10,501,448 B2
APPLICATION NO. : 16/042565
DATED : December 10, 2019
INVENTOR(S) : Chen et al.

It is certified that error appears in the above-identified patent and that said Letters Patent is hereby corrected as shown below:

On the Title Page

In Column 2, under "Other Publications", Line 23, delete "filedJan. 29," and insert --filed Jan. 29,-- therefor On page 2, in Column 1, under "Other Publications", Line 17, delete "dials" and insert --diols-- therefor On page 2, in Column 1, under "Other Publications", Lines 17-18, delete "MAIDI-TOF" and insert --MALDI-TOF-- therefor In the Specification In Column 2, Line 28, delete "of the of the" and insert --of the-- therefor In Column 3, Line 1, delete "occurrence." and insert --occurrence,-- therefor In Column 5, Line 53, delete "ethylenedioxy." and insert --ethylenedioxy,-- therefor In Column 6, Line 19, delete "C(O)." and insert --C(O),-- therefor In Column 6, Line 19, delete "ethylenedioxy. N(R)$_2$." and insert --ethylenedioxy, N(R)$_2$,-- therefor In Column 6, Lines 22-23, delete "(CH$_2$)$_{0-2}$N(R)N(R)$_2$." and insert --(CH$_2$)$_{0-2}$N(R)N(R)$_2$,-- therefor In Column 6, Line 40, delete "n-hexyl" and insert --n-hexyl,-- therefor In Column 6, Line 58, delete "-C(CH$_2$CH$_3$)-CH$_2$," and insert -- -C(CH$_2$CH$_3$)=CH$_2$,-- therefor In Column 6, Lines 66-67, after "heterocyclylalkyl", insert --,--

Signed and Sealed this
Seventeenth Day of November, 2020

Andrei Iancu
*Director of the United States Patent and Trademark Office*

CERTIFICATE OF CORRECTION (continued)
U.S. Pat. No. 10,501,448 B2

In Column 7, Line 29, delete "2,4-2,5-" and insert --2,4-, 2,5- -- therefor

In Column 9, Line 9, delete "CL" and insert --Cl,-- therefor

In Column 11, Line 10, delete "-R'-AZ- H)" and insert -- -R$^1$-AZ-H)-- therefor In Column 12, Lines 32-33, after "okra seed oil", insert --,--

In Column 12, Line 48, after "cannabis oil", insert --,--

In Column 12, Line 48, after "cedar oil", insert --,--

In Column 13, Line 64, delete "5.000," and insert --5,000,-- therefor

In Column 25, Line 28, delete "2.000, 5.000," and insert --2,000, 5,000,-- therefor In Columns 25-26, Line 67 and Line 13, delete "(C$_1$-C$_5$)alkylene." and insert --(C$_1$-C$_5$)alkylene,-- therefor In Column 33, Lines 42-52, delete " 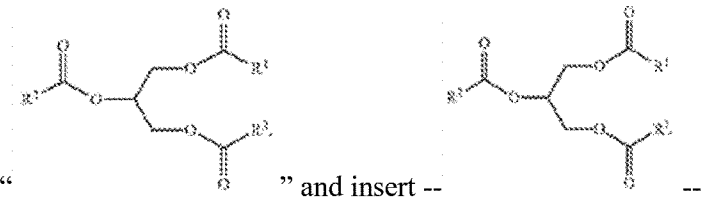 " and insert -- -- therefor In Column 33, Line 55, delete "R$^1$." and insert --R$^1$,-- therefor In Column 35, Line 67, delete "Polyurcthanes" and insert --Polyurethanes-- therefor In Columns 35-36, Line 67 and Line 32, delete "Diisocyanates," and insert --Diisocyanates.-- therefor In Column 37, Line 7, delete "Compounds+Aziridines," and insert --Compounds + Aziridines.-- therefor In Column 37, Line 26, delete "mlJmin." and insert --mL/min.-- therefor In Column 38, Line 15, delete "cm-1" and insert --cm$^{-1}$-- therefor In Column 38, Line 62, delete "titration." and insert --titration,-- therefor In Column 39, Line 33, delete "addition." and insert --addition,-- therefor In Column 39, Lines 51-52, delete "E' 3$v_e$RT," and insert --$E' = 3v_eRT$,-- therefor In Column 40, Line 22, delete "loss." and insert --loss,-- therefor

CERTIFICATE OF CORRECTION (continued)
U.S. Pat. No. 10,501,448 B2

In Column 42, Line 56, delete "occurrence." and insert --occurrence,-- therefor

In Column 42, Line 62, delete "occurrence." and insert --occurrence,-- therefor

In Column 44, Line 17, after "oil", insert --,--

In Column 45, Line 4, delete "1.2-" and insert --1,2- -- therefor

In Column 45, Line 26, delete "$(C_2-C_{10})$heterocyclyl." and insert --$(C_2-C_{10})$heterocyclyl,-- therefor In Column 45, Line 37, delete "$(C_1-C_5)$alkylene." and insert --$(C_1-C_5)$alkylene,-- therefor In Column 54, Line 60, delete "$(C_1-C_5)$hydrocarbyl" and insert --$(C_1-C_{50})$hydrocarbyl-- therefor In Column 54, Line 66, delete "unsubstituted." and insert --unsubstituted,-- therefor In Column 54, Line 67, delete "1,000." and insert --1,000,-- therefor In Column 55, Line 62, delete "occurrence." and insert --occurrence,-- therefor In Column 55, Line 65, delete "R," and insert --$R^5$,-- therefor In Column 56, Line 38, after "babassu oil", insert --,--

In Column 56, Line 40, after "nut oil", insert --,--

In Column 56, Line 53, after "ramtil oil", insert --,--

In Column 56, Line 62, delete "oil." and insert --oil,-- therefor

In Column 57, Line 37, delete "1.2-, 1.3-," and insert --1,2-, 1,3-,-- therefor

In Column 57, Line 40, delete "1.2-" and insert --1,2- -- therefor

In Column 58, Line 3, delete "$(C_1-C_5)$alkylene." and insert --$(C_1-C_5)$alkylene,-- therefor In Column 58, Line 8, delete "-CH-CH-." and insert -- -CH=CH-.-- therefor In the Claims In Column 67, Line 19, in Claim 1, delete "$L^l$" and insert --$L^1$-- therefor In Column 69, Line 6, in Claim 11, delete "$L^l$" and insert --$L^1$-- therefor In Column 69, Line 23, in Claim 16, delete "1,2," and insert --1,2-,-- therefor

CERTIFICATE OF CORRECTION (continued)
U.S. Pat. No. 10,501,448 B2

In Column 69, Line 26, in Claim 16, delete "1,2-or" and insert --1,2- or-- therefor In Column 69, Line 28, in Claim 16, delete "1,2,3, 1,2,4," and insert --1,2,3-, 1,2,4-,-- therefor